US008148696B2

(12) United States Patent
Widener et al.

(10) Patent No.: US 8,148,696 B2
(45) Date of Patent: Apr. 3, 2012

(54) SINGLE-USE EXTERNAL DOSIMETERS FOR USE IN RADIATION THERAPIES AND RELATED DEVICES AND COMPUTER PROGRAM PRODUCTS

(75) Inventors: Steven R. Widener, Wake Forest, NC (US); John Carroll, Wake Forest, NC (US)

(73) Assignee: SNC Holdings Corp., Morrisville, NC (US)

( * ) Notice: Subject to any disclaimer, the term of this patent is extended or adjusted under 35 U.S.C. 154(b) by 0 days.

(21) Appl. No.: 12/359,660

(22) Filed: Jan. 26, 2009

(65) Prior Publication Data

US 2009/0127469 A1    May 21, 2009

Related U.S. Application Data

(60) Division of application No. 10/865,615, filed on Jun. 10, 2004, now Pat. No. 7,495,224, which is a continuation-in-part of application No. 10/303,591, filed on Nov. 25, 2002, now Pat. No. 7,557,353.

(60) Provisional application No. 60/334,580, filed on Nov. 30, 2001.

(51) Int. Cl.
*G01T 1/02* (2006.01)
(52) U.S. Cl. ................................. 250/370.07
(58) Field of Classification Search .......... 250/370, 250/336.1; 702/116
See application file for complete search history.

(56) References Cited

U.S. PATENT DOCUMENTS

| 3,229,684 | A | 1/1966 | Nagumo at al. ........... 600/302 |
| 3,638,640 | A | 2/1972 | Shaw ........................ 128/2 R |
| 3,972,320 | A | 8/1976 | Kalman ..................... 128/2.1 A |
| 4,055,762 | A | 10/1977 | Durkin |
| 4,142,383 | A | 3/1979 | Eberhart |
| 4,163,380 | A | 8/1979 | Masoner ........................ 72/342 |
| 4,265,635 | A | 5/1981 | Kring |
| 4,326,535 | A | 4/1982 | Steffel et al. .................. 128/631 |
| 4,361,153 | A | 11/1982 | Slocum et al. ............. 128/419 P |
| 4,397,313 | A | 8/1983 | Vaguine ........................ 128/399 |
| 4,397,314 | A | 8/1983 | Vaguine ........................ 128/399 |
| 4,416,283 | A | 11/1983 | Slocum .................. 128/419 PG |
| 4,431,004 | A | 2/1984 | Bessman et al. ............. 128/635 |
| 4,475,401 | A | 10/1984 | Punia et al. |
| 4,480,189 | A | 10/1984 | Miyake et al. |
| 4,484,076 | A | 11/1984 | Thomson .................. 250/370.07 |
| 4,494,545 | A | 1/1985 | Slocum et al. ................. 128/1.5 |

(Continued)

FOREIGN PATENT DOCUMENTS

DE    3219558 A1    1/1983

(Continued)

OTHER PUBLICATIONS

European Search Report for Application No. 02784637.7; date of mailing Sep. 15, 2006.

(Continued)

*Primary Examiner* — David Porta
*Assistant Examiner* — Marcus Taningco
(74) *Attorney, Agent, or Firm* — Sara C. Kanos; Nexsen Pruet, LLC

(57) ABSTRACT

Methods, systems, devices, and computer program products include positioning disposable single-use radiation sensor patches that have adhesive means onto the skin of a patient to evaluate the radiation dose delivered during a treatment session. The sensor patches are configured to be minimally obtrusive and operate without the use of externally extending power chords or lead wires.

12 Claims, 31 Drawing Sheets

U.S. PATENT DOCUMENTS

| | | |
|---|---|---|
| 4,519,401 A | 5/1985 | Ko et al. ................... 118/748 |
| 4,523,279 A | 6/1985 | Sperinde et al. ............ 364/416 |
| 4,541,901 A | 9/1985 | Parker et al. |
| 4,543,953 A | 10/1985 | Slocum et al. .......... 128/419 PT |
| 4,554,639 A | 11/1985 | Baker et al. |
| 4,556,063 A | 12/1985 | Thompson et al. ...... 128/419 PT |
| 4,571,292 A | 2/1986 | Liu et al. ................... 204/412 |
| 4,571,589 A | 2/1986 | Slocum et al. .......... 128/419 PG |
| 4,575,676 A | 3/1986 | Palkuti ...................... 324/158 D |
| 4,625,733 A | 12/1986 | Säynäjäkangas ............. 128/687 |
| 4,638,436 A | 1/1987 | Badger et al. ................. 364/414 |
| RE32,361 E | 2/1987 | Duggan ........................ 128/696 |
| 4,642,463 A | 2/1987 | Thoms |
| 4,651,741 A | 3/1987 | Passafaro ..................... 128/633 |
| 4,655,880 A | 4/1987 | Liu ................................ 204/1 T |
| 4,678,916 A | 7/1987 | Thomson .................... 250/370 |
| 4,681,111 A | 7/1987 | Silvian ..................... 128/419 PT |
| 4,703,756 A | 11/1987 | Gough et al. ................. 128/635 |
| 4,719,919 A | 1/1988 | Marchosky et al. .......... 128/401 |
| 4,750,495 A | 6/1988 | Moore et al. ............ 128/419 PG |
| 4,769,547 A | 9/1988 | Uber, III ...................... 250/374 |
| 4,793,825 A | 12/1988 | Benjamin et al. ............. 128/419 |
| 4,796,641 A | 1/1989 | Mills et al. ................... 128/748 |
| 4,804,847 A | 2/1989 | Uber, III .................... 250/370 F |
| 4,846,191 A | 7/1989 | Brockway et al. ............ 128/748 |
| 4,847,617 A | 7/1989 | Silvian ..................... 340/970.16 |
| 4,900,422 A | 2/1990 | Bryan et al. .................. 204/401 |
| 4,913,153 A | 4/1990 | Hagmann et al. |
| 4,919,141 A | 4/1990 | Zier et al. ..................... 128/635 |
| 4,935,345 A | 6/1990 | Guilbeau et al. ................ 435/14 |
| 4,944,299 A | 7/1990 | Silvian ..................... 128/419 PG |
| 4,958,645 A | 9/1990 | Cadell et al. ................. 128/903 |
| 4,961,422 A | 10/1990 | Marchosky et al. .......... 128/399 |
| 4,970,391 A | 11/1990 | Uber, III ...................... 250/374 |
| 4,976,266 A | 12/1990 | Huffman et al. ............. 128/659 |
| 4,989,601 A | 2/1991 | Marchosky et al. .......... 128/399 |
| 5,008,546 A | 4/1991 | Mazziotta et al. ........... 250/366 |
| 5,012,411 A | 4/1991 | Policastro et al. ........ 364/413.06 |
| 5,074,318 A | 12/1991 | Campbell et al. |
| 5,083,031 A | 1/1992 | Hoelsher et al. |
| 5,098,547 A | 3/1992 | Bryan et al. .................. 204/401 |
| 5,109,850 A | 5/1992 | Blanco et al. ................ 128/635 |
| 5,117,113 A | 5/1992 | Thomson et al. ........ 250/370.07 |
| 5,117,824 A | 6/1992 | Keimel et al. ........... 128/419 PG |
| 5,121,748 A | 6/1992 | Ditz et al. |
| 5,126,937 A | 6/1992 | Yamaguchi et al. ..... 364/413.11 |
| 5,127,404 A | 7/1992 | Wyborny et al. .......... 128/419 P |
| 5,137,022 A | 8/1992 | Henry ..................... 128/419 PT |
| 5,148,404 A | 9/1992 | Hilferink et al. |
| 5,159,262 A | 10/1992 | Rumbaugh et al. ........... 324/765 |
| 5,163,380 A | 11/1992 | Duffy et al. ..................... 119/15 |
| 5,166,073 A | 11/1992 | Lefkowitz et al. .............. 436/57 |
| 5,179,281 A | 1/1993 | Tawil et al. |
| 5,186,172 A | 2/1993 | Fiddian-Green ............. 128/632 |
| 5,193,538 A | 3/1993 | Ekwall ..................... 128/419 PT |
| 5,197,466 A | 3/1993 | Marchosky et al. .......... 128/399 |
| 5,205,294 A | 4/1993 | Flach et al. ................... 128/696 |
| 5,215,887 A | 6/1993 | Saito ................................ 435/14 |
| 5,231,878 A | 8/1993 | Zanini-Fisher et al. |
| 5,264,843 A | 11/1993 | Silvian .......................... 340/870 |
| 5,309,085 A | 5/1994 | Sohn ............................ 324/71.5 |
| 5,314,450 A | 5/1994 | Thompson ..................... 607/32 |
| 5,318,023 A | 6/1994 | Vari et al. ..................... 128/633 |
| 5,324,315 A | 6/1994 | Grevious ........................ 607/60 |
| 5,330,634 A | 7/1994 | Wong et al. .................. 204/409 |
| 5,354,314 A | 10/1994 | Hardy et al. .................. 128/653 |
| 5,354,319 A | 10/1994 | Wyborny et al. ............... 607/32 |
| 5,355,880 A | 10/1994 | Thomas et al. ............... 128/633 |
| 5,372,133 A | 12/1994 | Hogen et al. ................. 128/631 |
| 5,377,676 A | 1/1995 | Vari et al. ..................... 128/634 |
| 5,383,909 A | 1/1995 | Keimel ............................. 607/5 |
| 5,400,382 A | 3/1995 | Welt et al. |
| 5,425,361 A | 6/1995 | Fenzlein et al. .............. 128/635 |
| 5,431,171 A | 7/1995 | Harrison et al. .............. 128/698 |
| 5,444,254 A | 8/1995 | Thomson |
| 5,466,246 A | 11/1995 | Silvian ........................... 607/32 |
| 5,470,345 A | 11/1995 | Hassler et al. .................. 607/36 |
| 5,476,488 A | 12/1995 | Morgan et al. ................. 607/30 |
| 5,476,634 A | 12/1995 | Bridges et al. |
| 5,477,050 A | 12/1995 | Kronenberg et al. |
| 5,480,415 A | 1/1996 | Cox et al. ........................ 607/32 |
| 5,481,262 A | 1/1996 | Urbas et al. ............... 340/870.17 |
| 5,497,772 A | 3/1996 | Schulman et al. ............ 128/635 |
| 5,505,828 A | 4/1996 | Wong et al. ................. 205/777.5 |
| 5,507,786 A | 4/1996 | Morgan et al. ................. 607/27 |
| 5,517,313 A | 5/1996 | Colvin, Jr. .................... 356/417 |
| 5,527,349 A | 6/1996 | Landry et al. |
| 5,535,752 A | 7/1996 | Halperin et al. .............. 128/670 |
| 5,538,005 A | 7/1996 | Harrison et al. .............. 128/698 |
| 5,543,111 A | 8/1996 | Bridges et al. |
| 5,545,187 A | 8/1996 | Bergstrom et al. ............. 607/31 |
| 5,549,113 A | 8/1996 | Halleck et al. ................ 128/633 |
| 5,549,654 A | 8/1996 | Powell ............................ 607/25 |
| 5,556,421 A | 9/1996 | Prutchi et al. ................... 607/36 |
| 5,557,702 A | 9/1996 | Yoshikawa et al. ........... 385/143 |
| 5,562,713 A | 10/1996 | Silvian ........................... 607/32 |
| 5,564,434 A | 10/1996 | Halperin et al. .............. 128/675 |
| 5,571,148 A | 11/1996 | Loeb et al. |
| 5,572,027 A | 11/1996 | Tawil et al. |
| 5,572,996 A | 11/1996 | Doiron et al. ................. 128/633 |
| 5,591,217 A | 1/1997 | Barreras ............................ 607/5 |
| 5,593,430 A | 1/1997 | Renger ............................. 607/9 |
| 5,596,199 A | 1/1997 | McNulty et al. ........ 250/370.07 |
| 5,606,163 A | 2/1997 | Huston et al. ................. 250/337 |
| 5,609,820 A | 3/1997 | Bridges et al. |
| 5,620,472 A | 4/1997 | Rahbari .......................... 128/903 |
| 5,620,475 A | 4/1997 | Magnusson .................... 607/30 |
| 5,620,479 A | 4/1997 | Diederich ....................... 607/97 |
| 5,626,630 A | 5/1997 | Markowitz et al. ............ 607/60 |
| 5,626,862 A | 5/1997 | Brem et al. ................... 424/426 |
| 5,628,324 A | 5/1997 | Sarbach ......................... 128/670 |
| 5,630,413 A | 5/1997 | Thomas et al. ............... 128/633 |
| 5,637,876 A | 6/1997 | Donahue et al. |
| 5,656,815 A | 8/1997 | Justus et al. ................... 250/337 |
| 5,656,998 A | 8/1997 | Fujiuchi et al. |
| 5,681,611 A | 10/1997 | Yoshikawa et al. ........ 427/163.2 |
| 5,682,888 A | 11/1997 | Olson et al. ................ 128/653.1 |
| 5,720,771 A | 2/1998 | Snell ................................ 607/60 |
| 5,731,957 A | 3/1998 | Brennan |
| 5,732,704 A | 3/1998 | Thurston et al. .............. 128/659 |
| 5,744,094 A | 4/1998 | Castberg et al. |
| 5,744,804 A | 4/1998 | Meijer et al. .................. 250/369 |
| 5,744,805 A | 4/1998 | Raylman et al. .......... 250/370.01 |
| 5,759,199 A | 6/1998 | Snell et al. ....................... 607/60 |
| 5,787,144 A | 7/1998 | Findlay |
| 5,791,344 A | 8/1998 | Schulman et al. ............ 128/635 |
| 5,811,814 A | 9/1998 | Leone et al. .................. 250/368 |
| 5,814,089 A | 9/1998 | Stokes et al. ................... 607/32 |
| 5,833,603 A | 11/1998 | Kovacs et al. ................. 600/317 |
| 5,840,148 A | 11/1998 | Campbell et al. ........... 156/275.5 |
| 5,847,391 A | 12/1998 | Sephton |
| 5,855,203 A | 1/1999 | Matter |
| 5,857,463 A | 1/1999 | Thurston et al. .............. 128/659 |
| 5,879,375 A | 3/1999 | Larson et al. ................... 607/30 |
| 5,891,179 A | 4/1999 | Er et al. .......................... 607/27 |
| 5,916,167 A | 6/1999 | Kramer et al. ................ 600/436 |
| 5,918,110 A | 6/1999 | Abraham-Fuchs et al. .... 438/48 |
| 5,928,150 A | 7/1999 | Call ............................... 600/436 |
| 5,932,879 A | 8/1999 | Raylman et al. ......... 250/370.06 |
| 5,939,453 A | 8/1999 | Heller et al. ................... 514/452 |
| 5,949,075 A | 9/1999 | Kishi |
| 5,987,350 A | 11/1999 | Thurston ...................... 600/436 |
| 6,001,067 A | 12/1999 | Shults et al. |
| 6,015,390 A | 1/2000 | Krag ............................. 600/549 |
| 6,025,137 A | 2/2000 | Shyjan .............................. 435/6 |
| 6,031,454 A | 2/2000 | Lovejoy et al. |
| D423,377 S | 4/2000 | Atterbury et al. .............. D10/47 |
| 6,047,214 A | 4/2000 | Mueller et al. .................. 607/61 |
| D424,453 S | 5/2000 | Atterbury et al. .............. D10/47 |
| 6,070,096 A | 5/2000 | Hayashi ........................ 600/477 |
| 6,076,009 A | 6/2000 | Raylman et al. .............. 600/436 |
| 6,087,666 A | 7/2000 | Huston et al. ................. 250/484.5 |
| 6,093,381 A | 7/2000 | Triozzi et al. ................. 424/1.49 |
| 6,099,821 A | 8/2000 | Rich et al. .................... 424/1.61 |
| 6,119,697 A | 9/2000 | Engel et al. |
| 6,132,681 A | 10/2000 | Faran et al. |
| 6,172,368 B1 | 1/2001 | Tarr et al. ................. 250/370.07 |

| | | | |
|---|---|---|---|
| 6,219,573 B1 | 4/2001 | Pompei | |
| 6,239,724 B1 | 5/2001 | Doron et al. | 340/870.28 |
| 6,240,312 B1 | 5/2001 | Alfano et al. | 600/478 |
| 6,242,741 B1 | 6/2001 | Miller et al. | 250/363.02 |
| 6,259,095 B1 | 7/2001 | Bouton et al. | 250/336.1 |
| 6,272,373 B1 | 8/2001 | Bouton | 600/436 |
| 6,274,159 B1 | 8/2001 | Marotta et al. | 424/426 |
| 6,295,680 B1 | 10/2001 | Wahl et al. | 14/1 |
| 6,304,766 B1 | 10/2001 | Colvin, Jr. | 600/317 |
| 6,363,940 B1 | 4/2002 | Krag | 128/899 |
| 6,398,710 B1 | 6/2002 | Ishikawa et al. | |
| 6,402,689 B1 | 6/2002 | Scarantino et al. | |
| 6,444,475 B1 | 9/2002 | Anderson, Jr. et al. | 436/161 |
| 6,614,025 B2 | 9/2003 | Thomson et al. | |
| 6,650,930 B2 | 11/2003 | Ding | 600/436 |
| 6,746,465 B2 | 6/2004 | Diederich et al. | |
| 7,010,340 B2 | 3/2006 | Scarantino et al. | |
| 2002/0008307 A1 | 1/2002 | Dickey | |
| 2002/0020689 A1 | 2/2002 | Leung | |
| 2004/0109789 A1 | 6/2004 | Faran et al. | |

FOREIGN PATENT DOCUMENTS

| | | |
|---|---|---|
| DE | 3332075 | 3/1984 |
| DE | 4341903 A1 | 6/1995 |
| EP | 0364045 A1 | 4/1990 |
| EP | 0420177 A1 | 3/1991 |
| EP | 0471957 A2 | 2/1992 |
| EP | 0537761 A2 | 4/1993 |
| EP | 0245073 B1 | 12/1993 |
| EP | 0386218 B1 | 10/1996 |
| GB | 2263196 A | 7/1993 |
| JP | 02147882 A | 6/1990 |
| JP | 07306269 | 11/1995 |
| JP | 63221278 | 9/1998 |
| SU | 414900 | 7/1976 |
| SU | 1603314 A1 | 10/1990 |
| WO | WO95/17809 | 6/1995 |
| WO | WO97/33513 | 9/1997 |
| WO | WO98/02209 A2 | 1/1998 |
| WO | WO 98-05965 | 2/1998 |
| WO | WO98/43701 | 8/1998 |
| WO | WO98/58250 | 12/1998 |
| WO | WO99/48419 | 9/1999 |
| WO | WO99/58065 | 11/1999 |
| WO | WO99/63881 | 12/1999 |
| WO | WO00/29096 | 5/2000 |
| WO | WO00/18294 | 6/2000 |
| WO | WO00/33065 | 6/2000 |
| WO | WO00/40299 | 7/2000 |
| WO | WO 01-22874 A1 | 4/2001 |
| WO | WO02/09775 | 2/2002 |
| WO | WO02/39917 | 5/2002 |
| WO | WO02/39918 | 5/2002 |
| WO | WO 02-086449 A2 | 10/2002 |
| WO | WO02/100485 | 12/2002 |
| WO | WO 03-047694 A2 | 6/2003 |

OTHER PUBLICATIONS

Akabani, Gamal, *Absorbed Dose Calculations in Haversian Canals for Several Beta-Emitting Radionuclides*, Journal of Nuclear Medicine; 34:1361-1366, (1993).
Almond et al., *AAPM's TG-51 protocol for clinical reference dosimetry of high-energy photon and electron beams*, Med. Phys. 26 (9), pp. 1847-1870, (Sep. 1999).
Van Den Bergh, H., *On the Evolution of Some Endoscopic Light Delivery Systems for Photodynamic Therapy*, Endoscopy, May 1998, pp. 392-407.
Demidecki et al., *Considerations on the calibration of small thermoluminescent dosimeters used for measurement of beta particle absorbed doses in liquid environments*, Med. Phys. 20 (4), pp. 1079-1087, (Jul.-Aug. 1993).
Gladstone et al., *A miniature MOSFET radiation dosimeter probe*, Med. Phys. 21 (11), pp. 1721-1728, (Nov. 1994).
Gladstone et al., *Real-Time, In Vivo Measurement of Radiation Dose during Radioimmunotherapy in Mice Using a Miniature MOSFET Dosimeter Probe*, Radiation Research 141, pp. 330-335 (1995).
Gratz et al., *Smart card for detection of alpha radiation sensors and actuators*, Sensors and Actuators, vol. 61 pp. 431-435 (1997).
Kolbert et al. *Implementation and Evaluation of Patient-Specific Three-Dimensional Internal Dosimetry*, Journal of Nuclear Medicine, vol. 38, No. 2, pp. 301-307, (Feb. 7, 1996).
Leichner et al., *Patient-Specific Dosimetry of Indium-III- and Yttrium-90-Labeled Monoclonal antibody CC49*, Journal of Nuclear Medicine, vol. 38, No. 4, pp. 5122-516, (Apr. 1997).
Liu et al., *A Radionuclide Therapy Treatment Planning and Dose Estimation System*, The Journal of Nuclear Medicine, vol. 40, No. 7, pp. 1151-1153, (Jul. 1999).
Loeb et al., *Injectable microstimulator for functional electrical stimulation*, Med. & Biol. Eng. & Comput., vol. 29, pp. NS13-NS19, (1991).
Ma et al., in *Ionizing Radiation Effects in MOS Devices and Circuits*, John Wiley & Sons, pp. 35-46 (1989).
Mackay et al. *Gamma-Ray Dose Mapping in Operational Candu Reactor Containment Areas Using MOS Dosimeters*, pp. 441-446, Reactor Dosimetry, ASTM, 1994.
Messenger et al., *The Effects of Radiation on Electronic systems*, Van Nostrand Reinhold, pp. 332-349 (1992).
Nardin et al., *A multichannel neuromuscular microstimulator with bidirectional telemetry*, Proc. Int. Conf. on Solid-State Sensors and Actuators, Stockholm, Sweden, vol. 1, pp. 59-62 (Jun. 1995).
Peet, D.J. et al., *Evaluation of a MOSFET radiation sensor for the measurement of entrance surface dose in diagnostic radiology*, The British Journal of Radiology, 72, Jun. 1999, pp. 562-568.
Shani, Gad, *Radiation Dosimetry instrumentation and Methods*, CRC Press, Boca Raton, Florida, 5 sheets including Table of Contents (1991).
Siegal et al., *MIRD Pamphlet No. 16: Techniques for Quantitative Radiopharmaceutical Biodistribution Data Acquisition and Analysis for Use in Human Radiation Dose Estimates*. Journal of Nuclear Medicine, 40:27S-61S (1999).
Siegal et al., *The Importance of Patient-Specific Radiation dose Calculations for the Administration of Radionuclides in Therapy*, Cellular and Molecular Biology 48(5), pp. 451-459 (Mar. 1, 2002).
Stabin, M. G., *Internal Radiation Dosimetry*, Nuclear Medicine, Part Two, The Scientific Basis of Nuclear Medicine, pp. 316-333 (1996).
Stenson et al., *Effects of implantable biomaterials on radiation dosimetry*, Head Neck, vol. 19, No. 5 pp. 384-390 (Aug. 1997).
Halvorsen, H., *Dosimetric evaluation of a new design MOSFET in vivo dosimeter*, Med. Phys. 32 (1), Jan. 2005; pp. 110-117.
http://www.thomson-elec.com/lineararray.htm, *Linear Array, Linear 5ive MOSFET Array*, Thomson/Nielsen Monitoring radiation in this world and beyond . . . , Dated Feb. 16, 2005, 5 sheets.
http://wvvw.thomson-elec.com/buildupcaps.htm, *Build-up Caps, Hemispherical Build-up Caps*, Thomas/Nielsen Monitoring radiation in this world and beyond . . . , Dated Feb. 16, 2005, 1 sheet.
http://www.cirsinc.com/products/model_plasticwater.html, *Plastic Water™, Calibrate photon and electron beams with 0.5% of true water dose*, Computerized Imaging Reference Systems, Inc., Dated Feb. 16, 2005, 1 sheet.
Akin et al., *RF Telemetry Powering and Control of Hermetically Sealed Integrated Sensors and Actuators*, Proc. Solid-State Sensors & Actuators Workshop, Hilton Head, SC, pp. 145-148 (1990).
Akin, T., K. Najafi, R.M. Bradley, *An Implantable Multichannel Digital Neural Recording System for a Micromachined Sieve Electrode*, Proc. Int. Conf. on Solid-State Sensors and Actuators, Stockholm, Sweden, vol. 1, pp. 51-54 (Jun. 1995).
Alecu et al., *Dose Perturbations Due to In Vivo Dosimetry With Diodes*, Radiotherapy and Oncology, pp. 289-291, vol. 42, (1997).
Barber et al., *Comparison of NaI(Tl), CdTe, and HgI2 Surgical Probes: Physical Characterization*, Med. Phys., 18(3):373-381 (May-Jun. 1991).
Barthe, Jean, *Electronic Dosimeters Based on Solid State Detectors*, Nuclear. Instruments. and Methods in Physics Research Sec. B vol. 184, pp. 158-189 (2001).
Berthold et al., *Method for In-Situ Detection of Tritium in Water*, McDermott Technology Inc./RDTPA 99-03, pp. 1-9 (Sep. 19-22, 1999).

Biotelemetrics, Inc., 6520 Contempo Lane, Boca Raton, Florida 33433, Tel: 407-394-0315. Biotelemetry Page, http://www.biotelemetrics.com/telemetry.html May 2004.

Blackstock et al., *Tumor Retention of 5-Fluorouracil Following Irradiation Observed Using 19F Nuclear Magnetic Resonance Spectroscopy*, Init J Radiat Oncol Biol Phys, 36(3):641-648 (Oct. 1, 1996).

Bojsen et al., *A Portable External Two-Channel Radiotelemetrical GM-Detector Unit, for Measurements of Radionuclide-Tracers In Vivo*, Int J Appl Radiat Isot, 25(4):161-166 (Apr. 1974).

Bojsen et al., *A Radiotelemetrical Measuring Device, Implantable on Animals, for Long Term Mersurements of Radionuclide Tracers*, Int J Appl Radiat Isot, 23(11):505-511 (Nov. 1972).

Braichotte et al., *Clinical Pharmacokinetic Studies of Photofrin by Fluorescence Spectroscopy in the Oral Cavity, the Esophagus, and the Bronchi*, Cancer, vol. 75, No. 11, Jun. 1, 1995, pp. 2768-2778.

Brochure, *Be as Smart as You Can be With BMDS and Smart Alec™ Your Partners in Intelligence*, Bio Medic Data Systems, Inc. (© 1999).

Brochure, *Come Along for the Incredible Journey in the Development of the IPTT-200*, Bio Medic Data Systems, Inc. (© 2000).

Butson, Martin J. et al, *A New Radiotherapy Surface Dose Detector: The MOSFET*, Medical Physics, American Institute of Physics, vol. 23 (5) pp. 655-658 (May 1996).

Cortese et al., *Clinical Application of a New Endoscopic Technique for Detection of In Situ Bronchial Carcinoma*, Mayo Clinic Proceedings, vol. 54, Oct. 1979, pp. 635-641.

Cosofret et al., *Microfabricated Sensor Arrays Sensitive to Ph and K+ for Ionic Distribution Measurements in the Beating Heart*, Analytical Chemistry, vol. 67, pp. 1647-1653 (1995).

Daghighian et al., *Intraoperative Beta Probe: A Device for Detecting Tissue Labeled With Positron or Electron Emitting Isotopes During Surgery*, Med Phys, 21(1):153-157 (Jan. 1994).

Data Sciences International, http://www.ispex.ca/companies/instrumentation/DataScInt.html, Profile web pages 1-2 and Instrumental Products 1-7, Copyright Ispex Exchange Inc., 2003, for examination purposes, applicant admits similar devices were available prior to earlier filing date of application.

Deutsch, S., *Fifteen-Electrode Time-Multiplex EEG Telemetry From Ambulatory Patients*, IEEE Transactions on Biomedical Engineering, vol. BME-26, pp. 153-159 (1979).

Dewhirst et al., *Soft-Tissue Sarcomas: MR Imaging and MR Spectroscopy for Prognosis and Therapy Monitoring*, Radiology, 174:847-853 (1990).

Dewhirst, *Concepts of Oxygen Transport at the Microcirculatory Level*, Seminars in Radiation Oncology, vol. 8, 1998, pp. 143-150.

Dienes et al., *Radiation Effects in Solids, Interscience Monographs in Physics and Astronomy*, vol. II, Interscience Publishers, Inc., pp. 1-4, 56-85, 90-122 and 129-177 (© 1957).

Dimitrakopoulou et al., *Studies with Positron Emission Tomography After Systemic Administration of Fluorine-18-Uracil in Patients with Liver Metastases from Colorectal Carcinoma*, J Nucl Med, 34:1075-1081 (Jul. 1993).

Essers, M. et al., *In Vivo Dosimetry During External Photon Beam Radiotherapy*, Int. J. Radiation Oncology Biol. Phys., vol. 43, No. 2, pp. 245-259, (1999).

Farrar IV Harry et al., *Gamma-Ray Dose Mapping in Operational Candu Reactor Containment Areas Using MOS Dosimeters*, pp. 441-446, Reactor Dosimetry, ASTM, 1994.

Fernald, *A Microprocessor-Based System for the Fast Prototyping of Implantable Instruments for Biomedical Research Applications*, Doctoral Dissertation, Elect. & Computer Eng., NC State Univ., (1992).

Fernald, K., T. Cook, T. Miller, III, J. Paulos, *A Microprocessor-Based Implantable Telemetry Systems*, Computer, vol. 24, No. 7, pp. 23-30 (1991).

Fisher, DR, *Radiation Dosimetry for Radioimmunotherapy. An Overview of Current Capabilities and Limitations*, Cancer, 73(3 Suppl):905-911 (Feb. 1, 1994).

Fryer, T., H. Sndler, W. Freund, E. McCutcheon, E. Carlson, *A Multichannel Implantable Telemetry System for Flow, Pressure, and ECG Measurements*, Jour. of Applied Physiology, vol. 39, pp. 318-326 (1973).

Gelezunas et al., *Silicon Avalanche Radiation Detectors: The Basis for a New Ini Vivo Radiation Detection Probe*, Eur J Nucl Med, 8(10):421-424 (1983).

Gerweck, *Tumor pH: Implications for Treatment and Novel Drug Design*, 8 Seminars in Radiation Oncology, No. 5, pp. 176-182 (Jul. 1998).

Gilligan et al., *Evaluation of a Subcutaneous Glucose Sensor Out to 3 Months in a Dog Model*, Diabetes Care, vol. 17, pp. 882-887 (1994).

Griffiths et al., *The Oxylite: A Fibre-Optic Oxygen Sensor*, British J. of Radiology, vol. 72, pp. 627-630 (1999).

Gschwend, S., J. Knutti, H. Allen, J. Meindl, *A General-Purpose Implantable Multichannel Telemetry System for Physiological Research*, Biotelemetry Patient Monitoring, vol. 6, pp. 107-117 (1979).

Hamburger et al, *Primary Bioassay of Human Tumor Stem Cells*, Science, 197:461-463 (1977).

Hansen, B., K. Aabo, J. Bojsen, *An Implantable, Externally Powered Radiotelemetric System for Long-Term ECG and Heart-Rate Monitoring*, Biotelemetry Patient Monitoring, vol. 9., pp. 228-237 (1982).

Hassan et al., *A Radiotelemetry Pill for the Measurement of Ionizing Radiation Using a Mercuric Iodide Detector*, Phys med Biol, 23(2):302-308 (Mar. 1978).

Heij et al., *Intraoperative Search for Neuroblastoma by MIBG and Radioguided Surgery With the Gamma Detector*, Med Pediatr Oncol, 28(3):171-174 (Mar. 1997).

Hines, *Advanced Biotelemetry Systems for Space Life Sciences: PH Telemetry*, Biotelementry XIII, Mar. 26-31, pp. 131-137 (1995).

Hirsch et al., *Early Detection of Lung Cancer: Clinical Perspectives of Recent Advances in Biology and Radiology*, Clinical Cancer Research, vol. 7, Jan. 2001, pp. 5-22.

Hoffman et al., *Intraoperative Probes and Imaging Probes*, Eur Jnl Nucl Med, 26(8):913-935 (Aug. 1999).

Holmstrom, N., P. Nilsson, J. Carlsten, S. Bowald, *Long-Term In Vivo Experience of an Electrochemical Sensor Using the Potential Step Technique for Measurement of Mixed Venous Oxygen Pressure*, Biosensors & Bioelectronics, 13, pp. 1287-1295 (1998).

Jornet et al., *Calibration of Semiconductor Detectors for Dose Assessment in Total Body Irradiation*, Radiotherapy and Oncology, pp. 247-251, vol. 38, (1996).

Kastrissios et al., *Screening for Sources of Interindividual Pharmacokinetic Variability in Anticancer Drug Therapy: Utility of Population Analysis*, Cancer Investigation, 19(1):57-64 (Jan. 30, 2001).

Kern, D.H., *Tumor Chemosensitivity and Chemoresistance Assays*, Cancer 79(7):1447-1450 (1997).

Khouri et al., *An Implantable Semiconductor Beta-Radiation Detector*, Am J Physiol, 232(1):H95-98 (Jan. 1977).

Kinsey et al., *Endoscopic System for Simultaneous Visual Examination and Electronic Detection of Fluorescence*, Review of Scientific Instruments, vol. 51, No. 10, Oct. 1980, pp. 1403-1406.

Kissel et al., *Noninvasive Determination of the Arterial Input Function of an Anticancer Drug From Dynamic PET Scans Using the Population Approach*, Med Phys 26(4):609-615 (Apr. 1999).

Konigsberg Instruments, Inc., http://guide.labanimal.com/guide/companyd.jsp?b=3930, Lab Animal p. 1, Product Categories p. 1, Lab Animal Buyers Guide 2003 p. 1 and Animal Research Equipment pp. 1-12, Nature Publishing Group, 2003, for examination purposes, applicant admits similar devices were available prior to earlier filing date of application.

Koutcher et al., *Potentiation of a Three Drug Chemotherapy Regimen by Radiation*, Cancer Res, 53:3518-3523 (1993).

Kulapaditharom et al., *Performance Characteristics of Fluorescence Endoscope in Detection of Head and Neck Cancers*, Annals of Ontology, Rhinology & Laryngol, vol. 110 (1), Jan. 2001, pp. 45-52.

Lambrechts, M., Sansen, W., *Biosensors: Microelectrochemical Device*, NY, NY: IOP Publishing Ltd., pp. 206-208 (1992).

Loncol et al., *Entrance and Exit Dose Measurements With Semiconductors and Thermoluminescent Dosemeters: A Comparison of Methods and In Vivo Results*, Radiotherapy and Oncology, pp. 179-187, vol. 41, (1996).

Lowe, S., et al., *P53 Status and the Efficacy of Cancer Therapy In Vivo*, Sci., vol. 266, pp. 807-810 (1994).

Ma et al., *The Photosensitizing Effect of the Photoproduct of Protoporphyrin IX*, J. Photochem Photobiol B, Jul. 2001, vol. 60 (2-3), pp. 108-113.

Mackay, *Bio-Medical Telemetry, Sensing and Transmitting Biological Information from Animals and Man*, Second edition. New York, NY: IEEE Press (1993).

Marzouk et al., *Electrodeposited Iridium Oxide pH Electrode for Measurement of Extracellular Myocardial Acidosis during Acute Ischemia*, Anal. Chem., vol. 70, pp. 5054-5061 (1998).

Mathur, V.K, *Ion Storage Dosimetry*, Nuclear Instruments and Methods in Physics Research B, vol. 184 pp. 190-206 (2001).

Mayinger et al., *Endoscopic Fluorescence Spectroscopy in the Upper GI Tract for the Detection of GI Cancer: Initial Experience*, The American Journal of Gastroenterology, vol. 96, No. 9, Sep. 2001, pp. 2616-2621.

Mayinger et al., *Light-induced Autofluorescence Spectroscopy for the Endoscopic Detection of Esophageal Cancer*, Gastrointestinal Endoscopy, vol. 54, No. 2, Aug. 2001, pp. 195-201.

Miller et al., *Clinical Molecular Imaging*, J Amer Coll Radiol 2004, 1, pp. 4-23.

Mittal et al., *Evaluation of an Ingestible Telemetric Temperature Sensor for Deep Hyperthermia Applications*, Int. J. Radiation Oncology Biol. Phys., vol. 21, pp. 1353-1361 (1991).

Moreno, D.J. et al, *A Simple Ionizing Radiation Spectrometer/Dosimeter based on Radiation Sensing Field Effect Transistors (RadFETs)* Transducers '97 International Conference on Solid-State Sensors and Actuators Chicago, pp. 1283-1286 (Jun. 16-19, 1997).

Mueller, J. S., H. T. Nagle, *Feasibility of Inductive Powering of Miniature Low-Power Biotelemetry for Use With Microfabricated Biomedical Sensors*, Proc. Biotelemetry XIII, Williamsburg, VA, Mar., pp. 372-377 (1995).

Myeck et al., *Colonic Polyp Differentiation Using Time-Resolved Autofluorescence Spectroscopy*, Gastrointest. Endosc., Oct. 1998, No. 48 (4), pp. 390-394.

National Aeronautics and Space Administration, *Extravehicular Activity Radiation Monitoring (EVARM)*, Fact Sheet FS 2001-11-191-MSFC, abstract review, Oct. 2001.

Olthuis, W., Bergveld, P., *Simplified Design of the Coulometric Sensor-Actuator System by the Application of a Time-Dependent Actuator Current*, Sensors and Actuators B, vol. 7, pp. 479-483 (1992).

Oshima et al, *Development of Micro-Telemetering Multi-Sensor Capsule System With Newly Developed LSI for the Clinical Applications*, Transducers '87, The $4^{th}$ International Conference on Solid-State Sensors and Actuators, pp. 163-166 (1987).

Pauley, Donald J., R. Martin, *A Microminiature Hybrid Multichannel Implantable Biotelemetry System*, Biotelemetry Patient Monitoring, vol. 8, pp. 163-172 (1981).

PCT International Search Report, International Application No. PCT/US01/47373 dated Aug. 6, 2002.

PCT International Search Report, International Application No. PCT/US02/12855 dated Dec. 16, 2002.

PCT International Search Report, International Application No. PCT/US02/38111.

Pendower, J., *Spontaneous Disappearance of Gall-stones*, Medical Memoranda, British Medical Journal, pp. 492, 1964.

Piwnica-Worms et al., *Functional Imaging of Multidrug-resistant P-Glycoprotein with an Organotechnitium Complex*. Cancer Res, 53:977-984 (1993).

Presant et al., *Enhancement of Fluorouracil Uptake in Human Colorectal and Gastric Cancers by Interferon or by High-Dose Methotrexate: An In Vivo Human Study Using Noninvasive $^{19}F$-Magnetic Resonance Spectroscopy*, J Clin Oncol, 18:255-261 (2000) Jan. 4, 1999.

Presant et al., *Human Tumor Fluorouracil Trapping: Clinical Correlations of In Vivo 19F Nuclear Magnetic Resonance Spectroscopy Pharmacokinetics*, J Clin Oncol, 8(11):1868-1873 (Nov. 1990).

Puers, B., P. Wouters, M. DeCooman, *A Low Power Multi-Channel Sensor Interface for Use in Digital Telemetry*, Sensors and Actuators A, vols. 37-38, pp. 260-267 (1993).

Ranii, D., N&O Article, *Company's Device Aims to Monitor Disease From Inside.*, Mar. 30, 2000.

Ranii, D., N&O Article, *Steel Seeks Go-Ahead for Clinical Trials*. Apr. 17, 2002.

Raylman et al., *Evaluation of Ion-Implanted-Silicon Detectors for Use in Intraoperative Positron-Sensitive Probes*, Med Phys, 23(11):1889-1895 (Nov. 1996).

Reece M.H. et al., *Semiconductor Mosfet Dosimetery*, Health Physics Society annual Meeting, pp. 1-14, 1988.

Rollins et al., *Potential New Endoscopic Techniques for the Earlier Diagnosis of Pre-Malignancy*, Best Pract. Res. Clin. Gastroenterol, Apr. 2001, vol. 15 (2), pp. 227-247.

Schantz et al, *In Vivo Native Cellular Fluorescence and Histological Characteristics of Head and Neck Cancer*, Clin. Cancer Res., May 1998, vol. 4 (5), pp. 1177-1182.

Shortt, Dr. Ken et al., *A New Direct Reading Extremity Dosimeter—How the ED-1 Sensor works*, Health Physics Society Annual Meeting, Jul. 1994.

Small Business Innovation Research Program Phase One Grant Application entitled *An Implantable Multi-channel System for Monitoring Tumors*, submitted on or about Dec. 1996 to U.S. Public Health Service.

Small Business Innovation Research Program Phase One Grant Application entitled *An Implantable Multi-channel System for Monitoring Tumors*, resubmitted with revisions on or about Aug. 1997 to the National Institute of Health.

Small Business Innovation Research Program Phase One Grant Application entitled *An Implantable Multi-channel System for Monitoring Tumors*, resubmitted to the U.S. funding authority on or about Apr. 1998.

Soubra, M. et al., *Evaluation of a Dual Bias Dual Metal Oxide-Silicon Semiconductor Field Effect Transistor Detector as Radiation Dosimeter*, American Assoc. Phys. Med., vol. 21, No. 4, pp. 567-572, Apr. 1994.

Stepp et al., *Fluorescence Endoscopy of Gastrointestinal Diseases: Basic Principles, Techniques, and Clinical Experience*, Endoscopy, May 1998, vol. 30 (4), pp. 379-386.

Stevens et al., *5-Flourouracil Metabolism Monitored In Vivo by $^{19}F$ NMR*, Br J Cancer, 50:113-117 (1984).

Sweeney et al., *Visualizing the Kinetics of Tumor-Cell Clearance in Living Animals*, PNAS, vol. 96, No. 21, pp. 12044-12049, Oct. 12, 1999.

Tarr, N.G. et al., *A Floating Gate MOSFET Dosimeter Requiring No External Bias Supply*. Redecs 97. Fourth European Conference on Radiation and its Effects on Components and Systems (Cat. No. $97^{TH}8294$), pp. 277-281 (1998).

Taylor et al., *The Forces in the Distal Femur and the Knee During Walking and Other Activities Measured by Telemetry*, J. of Anthroplasty, vol. 13, No. 4, pp. 428-437 (1998).

Thomson, I. et al., *Radiation Dosimetry with MOS Sensors*, Radiation Protection Dosimetry, Viol. 6, No. 1-4, Nuclear Technology Publishing, pp. 121-124, 1984.

UCL Christian de Duve Institute of Cellular Pathology, Ludwig Institute for Cancer Research. URL www.Icp.ucl.ac.be/report95/licr95.html (1995).

Van Den Bergh H., *On the Evolution of Some Endoscopic Light Delivery Systems for Photodynamic Therapy*, Endoscopy, May 1998, pp. 392-407.

Von Hoff et al., *Selection of Cancer Chemotherapy for a Patient by an In Vitro Assay Versus a Clinician*, JNCI 82:110-116 (1990) Oct. 25, 1989.

Watanabe et al., *A Preliminary Report on Continuous Recording of Salivary pH Using Telemetry in an Edentulous Patient*, Int'l J. Proshodontics, vol. 12, No. 4, pp. 313-317 (1999).

Wayne, E. et al., *Treatment of Thyroid Disorders*, To-day's Drugs, British Medical Journal, pp. 493-496, Aug. 22, 1964.

Webster, Editor, *Design of Cardiac Pacemakers*, New York, NY: IEEE Press, pp. 155-157 (1995).

Williams et al., *Multipurpose Chip for Physiological Measurements*, IEEE International Symposium on Circuits and Systems, vol. 4, pp. 255-258, Proc. (1994).

Wolf et al., *Potential of Microsensor-Based Feedback Bioactuators for Biophysical Cancer Treatment*, Biosensors & Bioelectronics, vol. 12, pp. 301-309 (1997).

Wolf et al., *19F-MRS Studies of Fluorinated Drugs in Humans*, Adv Drug Deliv Rev, 41(1):55-74 (Mar. 15, 2000).

Wolf et al., *Non-Invasive 19F-NMRS of 5-Fluorouracil in Pharmacokinetics and Pharmacodynamic Studies*, NMR Biomed 11(7):380-387 (Nov. 1998).

Wolf et al., *Tumor Trapping of 5-Fluorouracil: In Vivo $^{19}F$ NMR Spectroscopic Pharmacokinetics in Tumor-Bearing Humans and Rabbits*, Proc Natl Acad Sci USA, 87:492-496 (Jan. 1990).

Woolfenden et al., *Radiation Detector Probes for Tumor Localization Using Tumor-Seeking Radioactive Tracers*, AJR Am J Roentgenol, 153(1):35-39 (Jul. 1989).

Wouters, P., M. De Cooman, R. Puers, A Multi-Purpose CMOS Sensor Interface for Low-Power Applications, *IEEE Journal of Solid-State Circuits*, vol. 29, No. 8, pp. 952-956 (Aug. 1994).

Yang et al., *Visualizing Gene Expression by Whole-Body Fluorescence Imaging*, PNAS, vol. 97, No. 22, pp. 12278-12282, Oct. 24, 2000.

Yarnell et al., *Drug Assays on Organ Cultures of Biopsies from Human Tumours*, BR Med J 2:490-491 (1964).

Young, R. C., V. T. DeVita, *Cell Cycle Characteristics of Human Solid Tumors In Vivo*, Cell Tissue Kinetics, vol. 3, pp. 285-290 (1970).

Zanzonico et al., *The Intraoperative Gamma Probe: Basic Principles and Choices Available*, Semin Nucl Med 30 (1):33-48 (Jan. 2000).

Zonios, et al., *Diffuse Reflectance Spectroscopy of Human Adenomatous Colon Polyps In Vivo*, Applied Optics, Nov. 1999, vol. 1; 38 (31), pp. 6628-6637.

Zuckier et al., *Remotely Pollable Geiger-Muller Detector for Continuous Monitoring of Iodine-131 Therapy Patients*, J. of Nuclear Med., vol. 39, No. 9, pp. 1558-1562 (Sep. 1998).

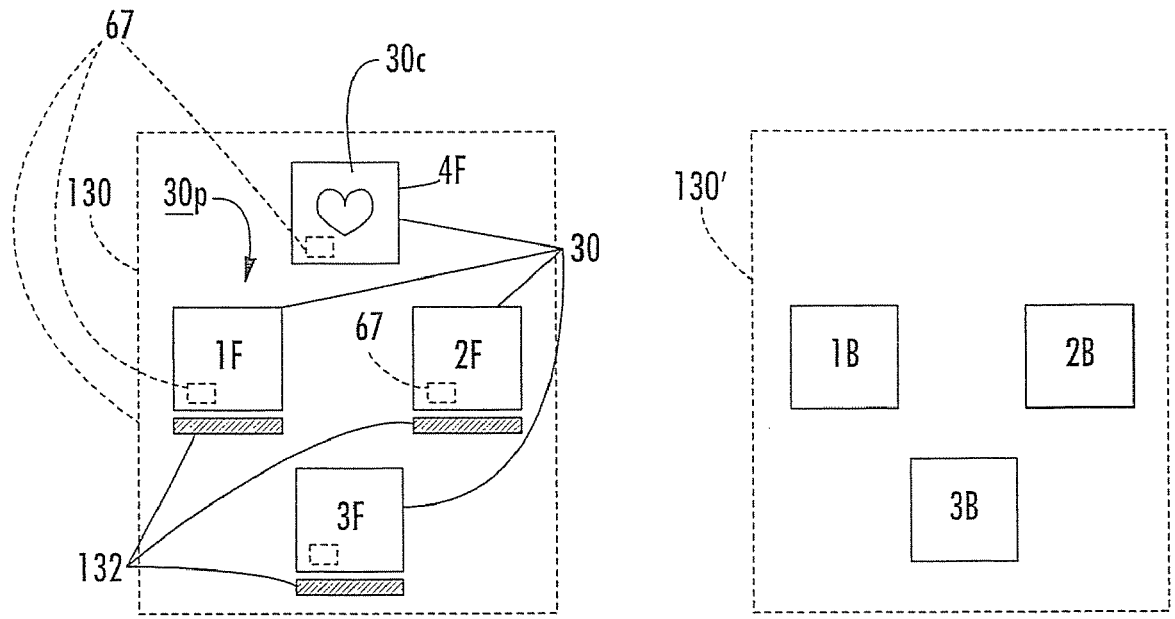
FIG. 3A
FIG. 3B
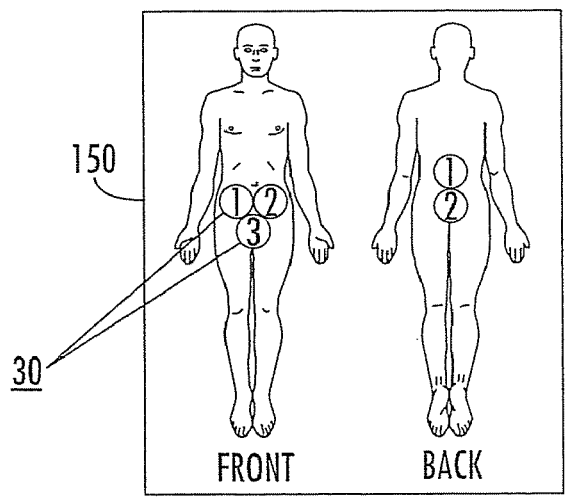
FIG. 3C

FIG. 4

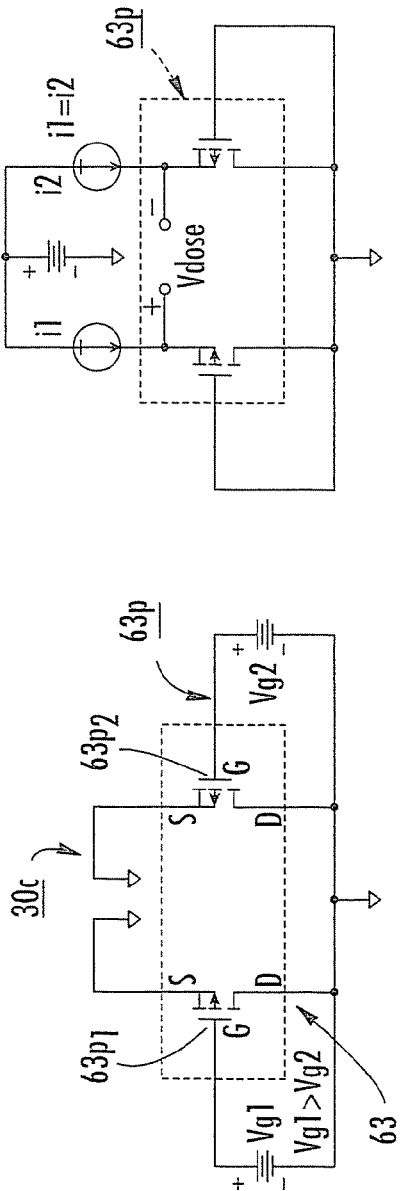
FIG. 14A
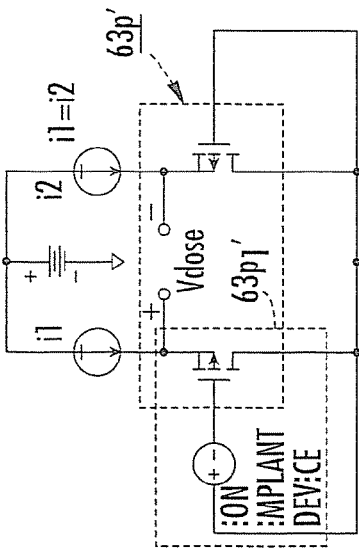
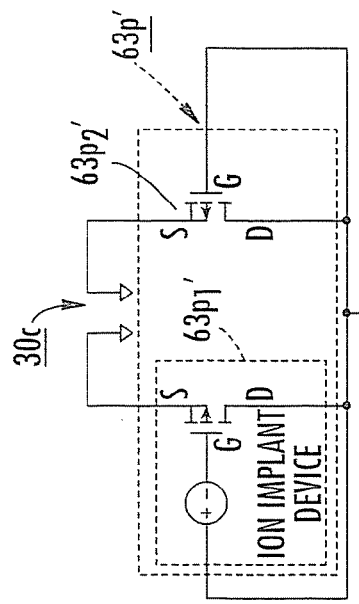
FIG. 14B

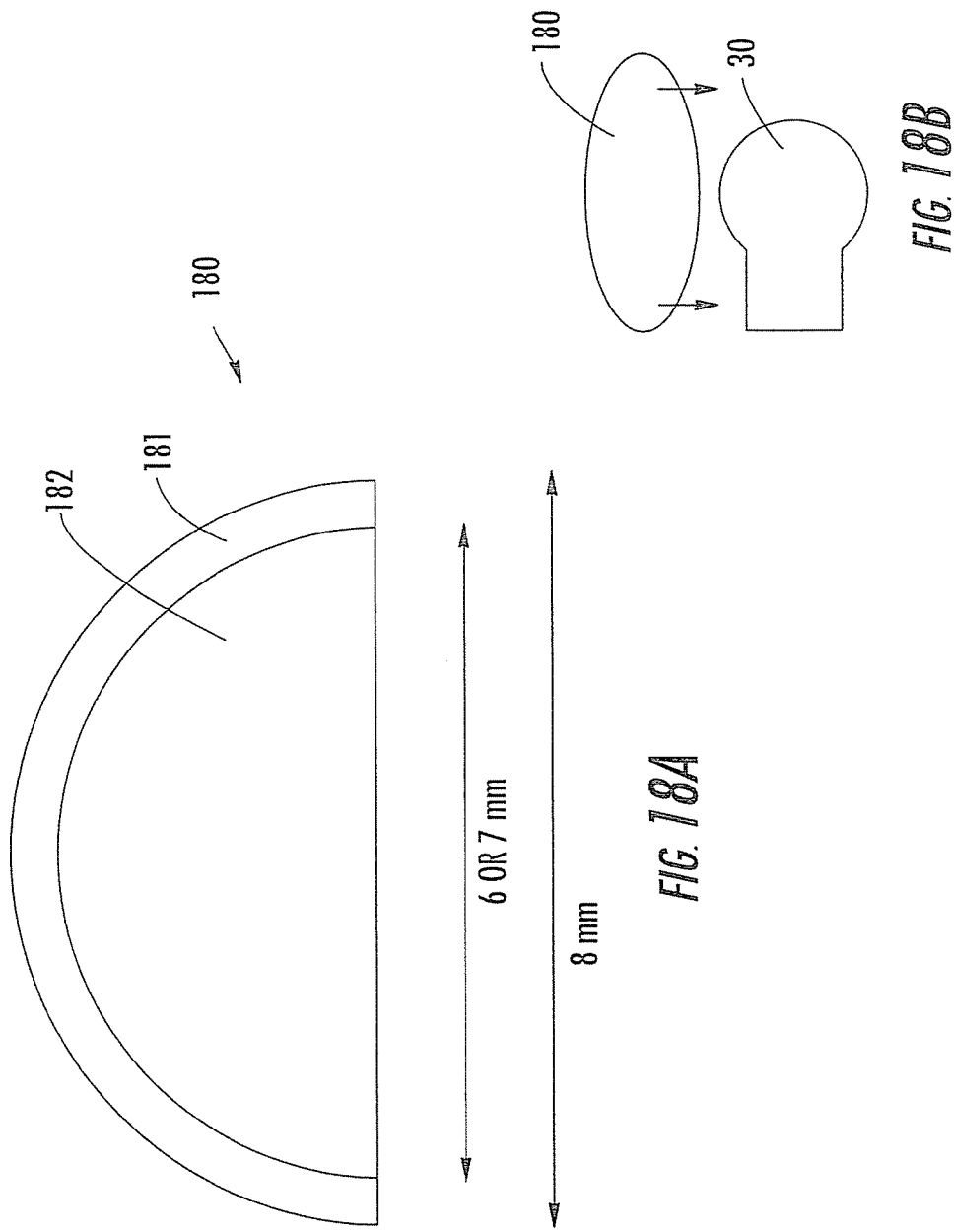

| PARAMETER | MIN | MAX | UNITS |
|---|---|---|---|
| ZTC BIAS CURRENT (DRAIN + GATE SHORTED) | 2 | 50 | μA |
| TEMPCO VS. ZTC BIAS CURRENT SLOPE (MEASURED +/−1μA AROUND THE ZTC CURRENT) | 0 | 100 | (μV/°C)/μA |
| ZTC BIAS CURRENT DRIFT WITH DOSE (100cGy DOSE) | 0 | 0.5 | μA/cGy |
| TEMPERATURE COEFFICIENT AT 10μA BIAS CURRENT (RADFET ONLY) | −2 | 2 | mV/°C |
| INITIAL THRESHOLD VOLTAGE (RADFET) (MEASURED AT ZTC CURRENT- ONE DOSE) | 0.25 | 6.0 | V |
| INITIAL THRESHOLD VOLTAGE (RADFET) (MEASURED AT 10μA - DVS) | 0.25 | 0.65 | V |
| TRANSCODUCTANCE (MEASURED AT ZTC CURRENT) | 10 | 100 | μMho |
| SENSITIVITY (INITIAL 100 cGy DOSE) | 0.35 | 2 | mV/cGY |
| FADE (INITIAL 100cGy DOSE - MEASURE CHANGE IN SHIFT FROM 5 MINUTE TO 15 MINUTE READINGS) | −2.5 | 2.5 | % OF VOLTAGE SHIFT |
| DIODE FORWARD VOLTAGE (MEASURED AT ZTC CURRENT - ONEDOSE ONLY) | 0.4 | 0.7 | V |

TABLE 1

*FIG. 19*

| FACTOR | VALUE |
|---|---|
| ENERGY = 8 MeV, ELECTRON | 1.055 |
| DOSE RATE = 300cGy / MIN | 1.000 |
| FIELD SIZE = 10 cm * 10 cm | 1.000 |
| TEMPERATURE = 33C | 1.000 |
| WEDGE ANGLE = 30 DEGREES | 0.990 |
| FADE TIME = 22 MINUTES | 1.021 |
|  |  |

TABLE 2

| COEFFICIENT | LOCATION |
|---|---|
| a - TEMPERATURE | 370-373h |
| b - TEMPERATURE | 374-377h |
| c - TEMPERATURE | 378-37Bh |
| d - TEMPERATURE | 37C-37Fh |

| COEFFICIENT | LOCATION |
|---|---|
| a - FADE | 380-383h |
| b - FADE | 384-387h |
| c - FADE | 388-38Bh |
| d - FADE | 38C-38Fh |

TABLE 4

| DESIRED CURRENT (μA) | IDEAL DAC SETTING REQUIRED (DEC) | ACTUAL DAC SETTING REQUIRED (DEC) |
|---|---|---|
| 2 | 32448 | 32317 |
| 5 | 31968 | 31837 |
| 10 | 31168 | 31039 |
| 20 | 29568 | 29439 |
| 30 | 27968 | 27841 |
| 40 | 26368 | 26242 |
| 50 | 24768 | 24644 |
| 100 | 16768 | 16651 |
| 150 | 8768 | 8659 |
| 200 | 768 | 666 |

| FIELD | DESCRIPTION (PATCH MEMORY LOCATION) |
|---|---|
| READING NUMBER | READING RECORD NUMBER |
| SERIAL NUMBER (KEY) | THE SENSOR'S SERIAL NUMBER (10-DIGIT BCD, FORMAT AABBCCDD-EE) |
| CALCULATED DOSE | THE CALCULATED DOSE IN cGy (IEEE-754) |
| ZEROING A/D VALUE | THE 24-BIT A/D CONVERSION VALUE FROM THE ZEROING OPERATION |
| READING A/D VALUE | THE 24-BIT A/D CONVERSION VALUE FROM THE READING OPERATION |
| PATIENT ID | THE PATIENT'S ID# (14-DIGIT BCD) |
| THERAPY MACHINE | THE THERAPY MACHINE'S ID# (2-DIGIT BCD) |
| FIELD NUMBER | THE FIELD # (2-DIGIT BCD) |
| SENSOR LOCATION | A NUMERIC DESCRIBING THE SENSOR PLACEMENT (2-DIGIT BCD) |
| PLANNED DOSE | THE PLANNED DOSE IN cGy (4-DIGIT BCD, FORMAT AAB.B) |
| THERAPIST NUMBER | THE THERAPIST'S ID# (4-DIGIT BCD) |
| ZERO TIME STAMP | THE ZERO READING TIME STAMP FOR THE SENSOR |
| DOSE TIME STAMP | THE DOSE READING TIME STAMP FOR THE SENSOR |
| % PLAN | THE PERCENTAGE OF THE PLANNED DOSE ACTUALLY DETECTED (IEEE-754) |
| CALC_CONFIG | THE CALCULATION CONFIGURATION REGISTER USED DURING DOSE CALCULATION |
| FIELD SIZE | THE FIELD SIZE (4-DIGIT BCD, FORMAT AA X BB $cm^2$) |
| DOSE RATE | THE DOSE RATE IN MU/MIN |
| ENERGY TYPE | TREATMENT ENERGY TYPE: 0 = NOT SPECIFIED, 1= PHOTON, 2 = ELECTRON |
| ENERGY | TREATMENT ENERGY IN MB OR MeV USED |
| MONITOR UNITS | THE # OF MONITOR UNITS (MU) APPLIED |
| SSD | THE SOURCE-TO-SURFACE DISTANCE |
| BOLUS THICKNESS | THE THICKNESS OF BOLUS IN mm (2-DIGIT BCD) |
| WEDGE ANGLE | THE WEDGE ANGLE (IN DEGREES) (2-DIGIT BCD) |
| CHECKSUM | 16-BIT CRC CHECKSUM FOR THE DOSE RECORD (62-BYTES) |

TABLE 6

FIG. 30

TABLE 7
Functional Specifications of a Test Strip
- The test strip may be constructed as a dosimeter with the RADFET replaced with a series combination of a 1.2V shunt reference (specified at 0.1% tolerance and a 10K resistor (0.1% tolerance). The Gate/Drain connection may have a 39K, 0.1% tolerance resistor connected to circuit ground on the test strip.
- The test strip memory map may contain all of the defaults from the base load (at the ZTC process).

FIG. 31

TABLE 8
Exemplary Functional Specifications of a Reader
- The Reader bias current may be configured to have an accuracy of within about +/-50nA.
- The Reader may reproduce the bias current between the "pre" and "post" readings to within about 1nA.
- The reader battery may be about a 9V user-replaceable type; other battery types may be used.
- A 5 Volt regulator may power the reader pcb (Vcc).
- The initial tolerance of the Vcc supply may be specified at about 3% or better.
- The battery may constantly supply a low-power (such as about 3.3V) regulator (which may be independent of the power switch state) to serve as a backup supply for the real-time clock.
- The back-up supply may have sufficient storage capacitance to allow for changing the battery without the loss of the real-time clock settings (typically at least 2 minutes).
- The main voltage reference may be specified as about a 4.096V, with about a 0.1% initial accuracy device with a specified temperature coefficient of about 10ppm/C or better.
- The battery voltage (after reverse polarity protection and the switching circuitry) may be sensed by the A/D converter on the Display Controller in order to monitor the battery voltage.
- The Reader Software may periodically sample the battery voltage and provide a "Low Battery" warning.
- The Reader Software may disable dose readings and may display a "Replace Battery" message on the display based on the sensed battery voltage.
- The reader may have an on-board substantially real-time clock capable of keeping track of time and date.
- The reader software may have functions to set and retrieve the current time and date.
- The time and date may be displayed on the LCD display and may be recorded as part of the electronic Dose record for each individual patch.
- The clock may maintain date and time settings long enough for the user to replace the battery (typically at least 2 minutes).
- The Reader may have on-board memory capable of storing reader-specific calibration coefficients, serial number, and user entered information (ex. Hospital ID).
- There may be a bank of memory capable of storing multiple dose records for display or for download through the USB port.
- Each Dose Record within the reader memory may contain multiple fields. Each record may have a size limit, such as about 64 bytes in length.
- The reader memory may be large enough to hold at least about 100-250 dose records.
- The display may be a 2-line, 16-character LCD module.
- This digital to analog controller, referenced as the IBIAS DAC, may work in conjunction with op-amp circuitry to provide about $\pm 2 - \pm 50 \mu A$ of programmable bias current with at least about 20nA of resolution under processor control.

FIG. 32A

TABLE 8
- The Reader may be designed to remain in calibration for at least about 6 months (typically about 1 year). The user may have the option to test the reader calibration using an external test strip.
- The reader may interrogate the test strip memory and request that the user perform a "zeroing operation". The test strip may be zeroed and the resulting DACB value may be compared to the DACB value determined at the factory and may indicate a "Reader OK" if the DACB value is within the limits provided or a "Reader needs Cal" message if the DACB value is outside the limits. The limits may be determined on a per-Reader basis in factory calibration. The test strip may be configured so as not to be modified by the reader.
- The reader may indicate "Reader OK" when the test strip is inserted and the (4.096V) reference is within a target range (typically 4.075 - 4.116V for the 4.096 V reference) and display "Reader needs Cal" if outside of these limits. The tolerance on the limits may be about +/- 0.005V.

*FIG. 32B*

TABLE 9
Exemplary Functional Specification of a Patch

- The flex circuit may be designed for ease of manufacturability and for substantial conformance to the contours of the body.
- The patch may be smaller than about 4cm long by about 1cm wide.
- There may be test points on the top-side of the patch to simplify the test fixturing for the patch.
- The flex circuits may be configured in an array of about 16*2.
- The 32 RADFET devices may fit within a window of about 0.75" by 4."
- There may be an area reserved on the flex circuit panel for an adhesive barcode to uniquely identify the panel.
- The flex circuit may be compatible with multiple insertions (such as at least about 10-20) into an appropriate connector.
- The RADFET may be a p-type enhancement-mode device.
- The SENSOR may be constrained so that at the Zero-Temperature Coefficient (ZTC) current, the threshold voltage, measured upon receipt, is less than about 6 Volts and greater than about 0.25V.
- The initial voltage shift of the SENSOR may be at least about 35mV for a 100cGy dose.
- The maximum initial threshold voltage shift for the SENSOR is about 200mV for a 100cGy dose.
- The system may be designed for a maximum difference in temperature between the "pre" and "post" readings of about ±5°C.
- The ZTC current for each individual SENSOR may be determined during factory processing and be configured to operate within a drift tolerance.
- The SENSOR may have a trans-conductance between about $1/10K\Omega$ and $1/100K\Omega$ (100µMho and 10µMho respectively) when measured at the ZTC current.
- The SENSOR may not fade more than 2.5% when a 100cGy dose is applied and the measurements taken at one or more of 5 minutes and 15 minutes after dose application.
- The Patch may have an on-board memory to store biasing, calibration and the dose record information.
- The device may be a serial EEPROM with a clock and data interface.
- The device may be rated to operate from about 3.3V – 10% to 5V +10%.
- The device may accommodate at least 2k bits of storage.
- The patch may be characterized for energy dependence and correction factors applied as necessary.
- There may be an adhesive (with peel away strip) on the bottom of the patch that allows direct placement on the patient.
- The SENSOR may have a ZTC current in the range of about 2µA to 50µA.
- A single patch may be provided to cover the 4-25MV, 4-25Mev energy range without correction factors.

FIG. 33

SINGLE-USE EXTERNAL DOSIMETERS FOR USE IN RADIATION THERAPIES AND RELATED DEVICES AND COMPUTER PROGRAM PRODUCTS

RELATED APPLICATIONS

This application is a divisional of and claims priority from U.S. patent application Ser. No. 10/865,615, filed Jun. 10, 2004, now U.S. Pat. No. 7,495,224, which is a continuation-in-part of U.S. patent application Ser. No. 10/303,591, filed Nov. 25, 2002, now U.S. Pat. No. 7,557,353, which claims priority from U.S. Provisional Patent Application Ser. No. 60/334,580, filed Nov. 30, 2001, the contents of which are hereby incorporated herein by reference as if set forth in their entirety.

FIELD OF THE INVENTION

The present invention generally relates to the assessment or quantitative evaluation of the amount of radiation delivered to a patient receiving radiation during a therapeutic procedure.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

BACKGROUND OF THE INVENTION

Conventionally, radiation therapy is delivered over a successive series of radiation treatment sessions. High-energy photons and/or electrons are carefully directed and/or focused from an ex vivo radiation source so that they travel into a targeted treatment area in a patient's body. The size, shape, and position of the treatment area (typically where a tumor is or was) as well as its anatomical location in the body and its proximity to sensitive normal tissues are considered when generating a particular patient's treatment plan. That is, the treatment is planned so as to deliver a suitably high dose of radiation to the tumor or targeted tissue while minimizing the dose to nearby sensitive tissue that typically cannot be completely avoided. Directing radiation into non-affected regions may produce undesired side effects particularly as it relates to tissue that may be sensitive to certain dosages of radiation. Unfortunately, even when the patient plan is carefully constructed to account for the location of the cancerous tissue and the sensitive non-affected regions, even small errors in set-up due to beam angle or patient position during delivery of the radiation therapy can inadvertently misdirect radiation into those regions or can influence the dose amount that is actually received by the targeted tissue. Further, the demand for radiation treatment equipment is typically relatively high and this demand may limit the set-up time allowed or allocated in the treatment room between patients.

In the past, implantable devices for oncology applications have been proposed to evaluate the radiation dose amount received ill vivo at the tumor site. See e.g., U.S. Pat. No. 6,402,689 to Scarantino et al., the contents of which are hereby incorporated by reference herein. Measuring the radiation at the tumor site in vivo can provide improved estimates of doses received. However, for certain tumor types or situations, a skin-mounted or external surface radiation dosimeter may be desirable and sufficient for clinical purposes.

Conventional external or skin-mounted radiation dosimeter systems use semiconductor circuitry and lead wires that power/operate the dosimeters. These types of dosimeters are available from Scandatronics and/or IBA ("Ion Beam Applications") having an international headquarters location in Belgium. While these radiation dosimeter systems may provide radiation dose estimations, they can, unfortunately, be relatively expensive. Further, these types of dosimeters are used for a plurality of patients potentially raising sterility or cleanliness problems between patients. Conventional dosimeter systems may also require substantial technician time before and during the radiation session. For example, conventional dosimeter systems need to be calibrated before the radiation session may begin. In addition, the lead wires can be cumbersome to connect to the patients and may require excessive set-up time as the technician has to connect the lead wires to run from the patient to the monitoring system and then store the lead wire bundle between patient treatment sessions. Therefore, technicians do not always take the time to use this type of system, and no confirmation estimate of the actual radiation delivered is obtained.

Other radiation sensors include thermo-luminescent detectors (TLD's). However, while TLD detectors do not require wires during operation, they are analyzed using a spectrophotometer (that may be located in an offsite laboratory) and are not conducive to real-time readings.

Devices, methods and systems of radiation detection are also discussed in U.S. Pat. Nos. 4,678,916, 5,117,113, 5,444, 254, 6,172,368, 6,614,025 and 6,650,930 that are assigned to Thomson & Nielsen.

In view of the foregoing there remains a need for improved economical and easy to use radiation dosimeters.

OBJECTS AND SUMMARY OF THE INVENTION

It is therefore an object of the present invention to provide a cost-effective surface mount radiation dosimeter that can be used to evaluate the radiation dose delivered to a patient undergoing radiation therapy.

It is a further object of the present invention to provide economic methods and devices that can reduce labor set-up time in the radiation treatment chamber over conventional evaluation methods and devices.

It is an additional object of the present invention to provide a memory storage device on the patch to record the dose history of the patch. This memory storage device may be queried at any time in order to obtain a record of the dose applied to the patch. Other information, such as patient identification, time, date, hospital, therapist, state of the device, dosed/undosed and calibration data may be stored in the memory storage device.

It is an additional object of the present invention to provide an economic method of determining the amount of radiation delivered to an oncology patient in situ.

These and other objects can be satisfied by the present invention by a disposable, single-use skin mounted radiation dosimeter that has a self-contained package that is small, adhesively attachable to the skin of the patient, and operates in a relatively easy to operate and read manner without requiring the use of lead wires.

Certain embodiments of the present invention are directed to methods for monitoring radiation doses administered to patients undergoing radiation treatments. The methods include the steps of: (a) releasably securing at least one single-use dosimeter sensor patch onto the skin of the patient such that the patch is self-contained and devoid of leads extending therefrom; (b) administering radiation to the patient in a first treatment session; (c) contacting the sensor patch with a dose-reader device after the administering step to obtain data associated with a change in an operational parameter in the dosimeter sensor patch; and (d) determining the radiation dose received by the patient during the administering step based on the change in the operational parameter.

In some embodiments, the sensor patch may be pre-dosed and/or calibrated before the sensor patch is secured to the patient. The obtained data may be stored in an electronic storage device provided on the sensor patch itself. The storage device may be, for example, an EEPROM. Other information, such as the patient's name, the doctor's name, the test date and the like, may also be stored in the storage device provided on the sensor patch. In further embodiments of the present invention, the electronic memory may include methodology data that instructs a reader how to interface with, i.e., obtain data from, the sensor patch(es). In still further embodiments of the present invention, the electronic memory may include a zero temperature coefficient (which may be used interchangeably for the phrase "zero temperature coefficient") of a MOSFET included on the sensor patch. This zero temperature coefficient may be used to bias the MOSFET after the radiation treatment before a post-radiation threshold voltage is obtained. Alternatively, the data can be stored on a computer readable memory integrated on a physical record sheet that can be placed in the patient's file.

In some embodiments of the present invention, a zero temperature coefficient of the MOSFET may be measured prior to the administering of therapeutic radiation to the patient and stored in the electronic memory. The MOSFET may be biased using the stored zero temperature coefficient after the administration of therapeutic radiation to the patient and the radiation dose may be automatically calculated based on the change in threshold voltage of the MOSFET.

Other embodiments are directed to systems for monitoring radiation administered to a patient during a therapeutic treatment. The system comprises: (a) at least one disposable single-use dosimeter patch, the patch comprising a body holding a circuit with at least one MOSFET and an external reader contact region thereon, the MOSFET(s) having an associated threshold voltage that changes when exposed to radiation, the body comprising opposing upper and lower primary surfaces; and (b) an external portable dose-reader being configured to make electrical contact with the patch by physically engaging with the contact region on the patch to obtain voltage threshold data corresponding to the dose amount of radiation exposure it is exposed to in use. During irradiation, the patch is self-contained (e.g., has a perimeter that is devoid of outwardly external lead wires).

In some embodiments, the patch includes a conformable resilient body. The lower primary surface may include a medical grade adhesive and the sensor patch may be pressed on to secure the sensor patch to the patient. In other embodiments, an adhesive coverlay is applied over the sensor patch to secure the sensor to the patient. A portion or all of the sensor patch may be adapted to be inserted into the dose-reader to transmit the dose data and the dose-reader may similarly be adapted to receive a portion or all of the sensor patch. Insertion of the sensor patch into the reader electrically couples the sensor to the reader and allows the reader to receive the radiation dose data from the sensor patch. The sensor patch may also include an electronic storage device in electrical communication with the sensor. The sensor patch may then be pre-dosed and/or calibrated before the radiation session. Data may be downloaded from the electronic memory of the sensor patch to a remote computer and/or a computer application using the electrical coupling of the sensor patch and the dose-reader.

In certain embodiments, the at least one dosimeter patch is a plurality of discrete sensor patches and the reader is configured to serially contact with each respective sensor patch to obtain the threshold voltage value associated therewith.

A sheet of sensor patches may be pre-dosed and/or calibrated simultaneously or individually before the sensor patches are secured to the patient. The calibration and/or pre-dosing may be performed at the original equipment manufacturer (OEM) or at the actual test site. The sheet of sensor patches may include about 30 to about 100 sensors. The sensors may also be provided in a high density array of sensors where so many sensors are provided in a certain area of the high density array, for example, multiple sensors may be provided per square inch or per 3 by 3 inch regions of the high density array.

Still other embodiments are directed to sets of disposable single-use radiation dosimeter patches. The sets comprise a plurality of discrete disposable single-use dosimeter patches, each patch comprises a conformable body holding a circuit with an operational electronic component that changes a parameter in a detectable predictable manner when exposed to radiation, the body comprising opposing upper and lower primary surfaces and the dosimeter patch, in use and positioned on the patient, is devoid of externally hanging lead wires.

The operational electronic component may be a radiation sensitive biased MOSFET or MOSFETs (such as MOSFET pairs) and the detectable operational parameter that changes can be the MOSFET threshold voltage(s). Furthermore, a medical grade adhesive may be supplied on the lower primary surface of the sensor body such that the sensor may be adhered to the patient's skin. In certain embodiments, an adhesive coverlay may be provide over the body of the sensor to secure the sensor to the patients skin.

In some embodiments of the present invention, a buildup cap is placed over the sensor patch to, for example, simulate placement of the sensor patch beneath the patient's skin. This type of simulation may help to focus and/or form equilibrium in the radiation beam in proximity to the sensor patch and, therefore, increase the reliability of radiation measurement. The buildup cap may simulate a distance of from about 1 to about 3 cm beneath the skin of the patient. In certain embodiments of the present invention, the buildup cap may have a hemispherical shape and may be configured to hook onto the sensor patch. The buildup cap may include a layer of molded polystyrene and a layer of copper on the layer of molded polystyrene. The copper layer may have a thickness of from about 0.5 to about 1 mm and the polystyrene may have a diameter of from about 6 to about 7 mm.

Another embodiment is directed to a computer program product for evaluating a radiation dose delivered to a patient. The computer program product comprises a computer readable storage medium having computer readable program code embodied in the medium. The computer-readable program code comprises: (a) computer readable program code for receiving pre-irradiation threshold voltage data associated with a plurality of disposable sensor patches; (b) computer readable program code for accepting data from a reader configured to electrically serially contact each of the plurality of disposable sensors for a short time; and (c) computer readable program code for determining the voltage threshold shift of the disposable sensor patches after radiation to determine the radiation exposure.

In still further embodiments of the present invention, a dose-reader may be adapted to receive a sensor patch in a sensor port. The sensor patch is also adapted to be inserted in the sensor port. The dose-reader can be a pocket or palm sized portable device. The dose-reader may also include a communications port, for example, a universal serial port (USB), RS 232 and the like, for downloading obtained data to a computer application or remote computer. The dose-reader functionality may be incorporated into a personal digital assistant (PDA) or other pervasive computer device.

In some embodiments of the present invention, a dose reader may be provided having a circuit integrated with the reader that is configured to communicate with an electronic memory of at least one single use dosimeter patch to obtain threshold data corresponding to a dose amount of radiation exposure the at least one sensor patch is exposed to in use and to prompt a user to provide predetermined data needed to determine the dose amount. The dose reader may be configured to automatically prompt the user of the reader for predetermined data before determining the radiation dose and automatically determine the radiation dose using the predetermined data. The predetermined data may include a correction factor related to the at least one sensor patch.

In further embodiments the sensor patch may be configured to communicate with the dose-reader wirelessly. For example, the sensor patch and the dose-reader may both be equipped with a radio frequency (RF) interface so that information may be shared between the two devices.

In still further embodiments of the present invention, a test strip may be provided. The test strip is sized and configured to be read by an external dose-reader. The test strip can be sized and configured to be generally the same as a patch. The test strip may include a conformable substrate holding a circuit. The circuit may include a resistor and a voltage reference, operational parameters of which may be configured to change in a detectable predictable manner when exposed to radiation to indicate a calibrated status of the external reader.

In some embodiments of the present invention, the voltage reference of the test strip includes a 1.2 V shunt and the resistor includes comprises a 10 KΩ resistor. The circuit may be adapted to engage with the external reader, compare a pre-radiation value to a post-radiation value to provide a comparison result and determine the state of the reader based on the comparison result. The circuit may be configured to indicate that the external reader is functional if the comparison result is within a set of defined limits and that the external reader is not functional if the comparison result is outside the set of limits.

The foregoing and other objects and aspects of the present invention are explained further in the specification set forth below.

BRIEF DESCRIPTION OF THE FIGURES

FIGS. 3A and 3B are illustrations of sets of disposable dosimeter patches according to still further embodiments of the present invention.

FIG. 3C is an anatomical map of sensor location according to some embodiments of the present invention.

FIG. 4 illustrates an exemplary patient information form according to some embodiments of the present invention.

FIG. 14A is a schematic of a circuit diagram with a MOSFET pair, the left side of the figure corresponding to an irradiation operative configuration and the right side of the figure corresponding to a read dose operative configuration, according to some embodiments of the present invention.

FIG. 14B is a schematic of a circuit diagram with a MOSFET pair, the left side of the figure corresponding to an irradiation operative configuration and the right side of the figure corresponding to a read dose operative configuration, according to further embodiments of the present invention.

FIGS. 18A and 18B are schematic diagrams illustrating buildup caps according to further embodiments of the present invention.

FIG. 19 is a table including sensor specifications according to further embodiments of the present invention.

FIG. 30 is a table including a list of items included in an exemplary dose record according to some embodiments of the present invention.

FIG. 31 is a table including functional specifications of test strips according to further embodiments of the present invention.

FIGS. 32A and 32B is a table including functional specifications readers according to still further embodiments of the present invention.

FIG. 33 is a table including functional specifications of patches according to some embodiments of the present invention.

DESCRIPTION OF EMBODIMENTS OF THE INVENTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain components, features, or layers may be exaggerated for clarity. In the block diagrams or flow charts, broken lines indicate optional operations, or features unless stated otherwise. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

The statements characterizing one or more of the priority applications as a "continuation-in-part" application of a prior application listed under the "Related Applications" section above is used to indicate that additional subject matter was added to the specification of the prior application but does not necessarily mean that the entire invention described and claimed in the present application is not supported in full by the prior application(s).

Figure 1:
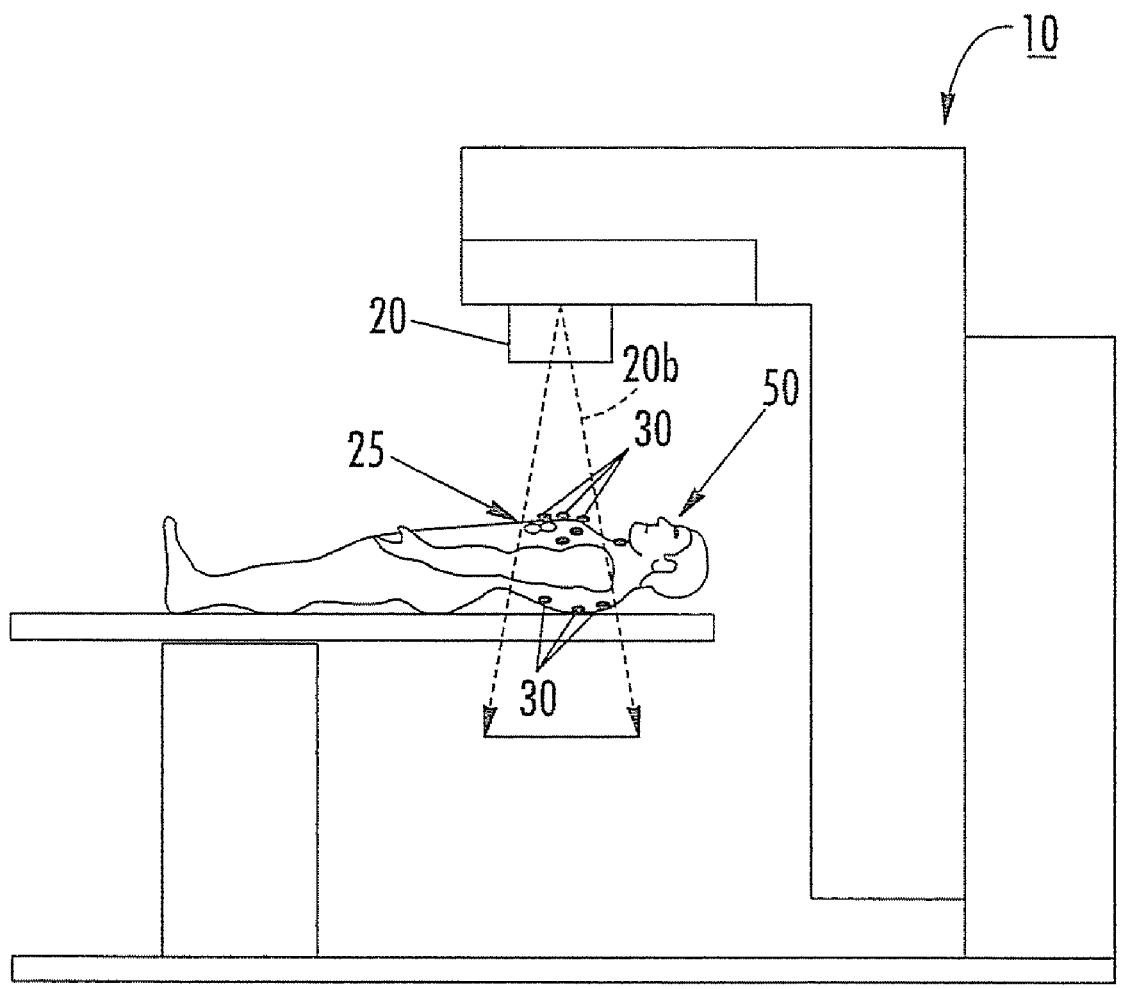
FIG. 1 is a schematic illustration of a patient undergoing radiation treatment according to some embodiments of the present invention.

FIG. 1 illustrates an example of a radiation system 10 with a radiation beam source 20 directed at a patient 50 having a tumor site. The patient 50 can be positioned so as to be aligned and stationary with respect to the beam 20b (illustrated by the diverging dotted lines) during the treatment. As such, the patient 50 can be arranged in any desired position depending on the direction of the beam, the location of the tumor, and the type of radiation therapy system employed. As shown, the patient is reclined, substantially flat and face up on a table so that the beam 20b is directed into the targeted tumor site in the body as the patient undergoes radiation therapy in a treatment session. Typically, the patient will undergo a plurality of successive treatment sessions over a treatment period. Each treatment session may be planned to administer radiation doses of between about 1-2 Gray (100-200 cGy) with an overall typical treatment limit of about 35-80 Gray.

To help monitor or estimate the amount of radiation that is delivered to the patient during a treatment session, at least one disposable single-use dosimeter sensor patch 30 can be positioned externally on the skin of the patient 50. As used herein, "single-use" is used to refer to a use for a single patient during a treatment session. The sensor patch 30 is typically worn once proximate in time and during a treatment. In other embodiments, the sensor patch 30 may be episodically worn or continuously worn over a target period. It will be understood that a treatment session may include an active radiotherapy administration during a single treatment session or serially spaced apart treatment sessions. The treatment session may have a duration of minutes, hours, days and the like. Furthermore, a calibration dose obtained before the sensor patch 30 is positioned on a patient is not to be considered the "single-use."

As shown in FIG. 1, a plurality of sensor patches 30 are located both on the front and back of the patient 50. The sensor patches 30 are configured to change an operational parameter in a predictable manner that correlates to radiation dose it receives, as will be discussed further below. The sensor patch 30 can be configured so as to be self-contained and discrete and devoid of dangling lead wires extending to a remote power source or operating system during use and in position on the patient. As such, a reader, for example, reader 75 (FIGS. 6 and 7), can be configured to obtain the data from the sensor patch 30 by, for example, electrically contacting with each sensor patch 30 of interest.

As used herein, the reference number "75" will be used to refer generally to a reader device according to embodiments of the present invention. Particular embodiments of a reader device 75 may be referred to using the reference number 75 and one or more primes attached thereto. For example, particular embodiments of the reader device may be denoted 75' or 75". This convention may similarly be used with respect to other features of the present invention. For example, the reference number "30'" will be used to refer to particular embodiments of a sensor patch herein. It will be understood that features discussed with respect to any embodiment of the present invention may be incorporated into other embodiments of the present invention even if these features are not discussed specifically with reference to each individual embodiment.

Figure 2:
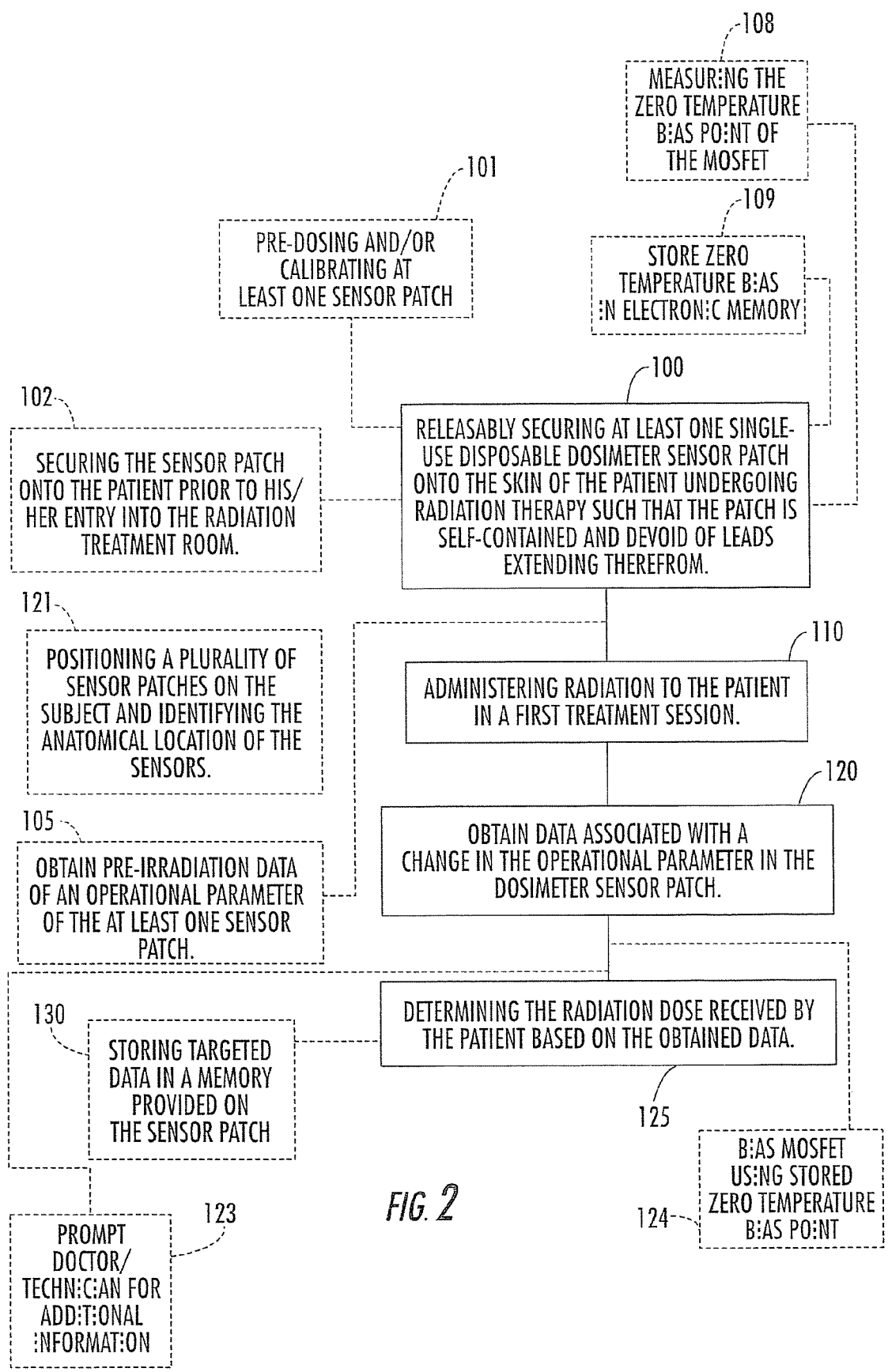
FIG. 2 is a block diagram of operations for monitoring patients undergoing radiation treatments according to further embodiments of the present invention.

Referring to FIG. 2, operations that can be carried out to monitor the radiation dose that is delivered to a patient undergoing radiation therapy are illustrated. At least one single-use dosimeter sensor patch can be releasably secured to the skin of the patient (block 100). In certain embodiments, the sensor patch may be calibrated and/or pre-dosed before being attached to the patient (block 101). The calibration and/or pre-dosing of the sensor patch may be done on an individual patch basis or many sensor patches may be calibrated and/or pre-dosed in batches simultaneously as discussed further below. In certain embodiments, the patch(es) can be conveniently attached to the patient in operation-ready condition before the patient enters the radiation treatment room or chamber (block 102) to limit or reduce the set-up time required or the "down-time" of the equipment or the treatment room. In other words, the sensor patch or patches may be secured to the patient prior to his/her entry into the radiation treatment room. A pre-irradiation or pre-dose measurement or reading of data associated with an operational parameter of the sensor patch(es) 30 can be obtained prior to initiation of the radiation treatment (block 105). The data can be obtained in situ, with the sensor patch(es) 30 in position on the patient. Alternatively, the pre-dose data can be established prior to positioning the sensor patch(es) onto the subject as discussed above and the data then transferred to the reader or associated controller and/or computer at a desired time.

In certain embodiments of the sensor patch(es), the post-radiation reading can be taken when the patient leaves the treatment room to evaluate the dose delivered during the treatment session to limit the amount of room-use time. The sensor patches 30 can be removed from the patient and then read by a handheld portable and/or a bench top reader. In other embodiments, the reading can be obtained while the sensor patches 30 remain on the patient. In certain particular embodiments, the reading may be able to be obtained in situ during the treatment session (without removing the sensor patch(es) from the patient) to provide real-time feedback to the clinician estimating whether the desired dose is being administered to the patient. In certain embodiments, the temperature of the sensor patch (such as at a location adjacent the circuitry) or of the subject (skin or core body) can also be ascertained or obtained and taken into account when calculating the radiation dose. In any event the dose reading can be obtained without requiring external powering or externally applied biasing of the sensor patches 30 during the radiation treatment.

In certain embodiments, a plurality of discrete sensor patches 30 can be positioned to cover a region on the skin that is in the radiation beam path so as to reside over the tumor site. In particular embodiments, one or more sensor patches 30 can also be positioned in radiation sensitive areas of the body to confirm stray radiation is not unduly transmitted thereto. FIG. 1 illustrates that a sensor patch can be located at the neck over the thyroid when the tumor site is over the chest region. As such, sensitive regions include, but are not limited to, the thyroid, the spine, the heart, the lungs, the brain, and the like.

In any event, referring again to FIG. 2, radiation is administered to the patient in a first treatment session (block 110). Data associated with a change in an operational parameter in the dosimeter sensor patch circuitry may be obtained from the sensor patch using a reader device (block 120) after administering the radiation to the patient (block 110). In certain embodiments, a sensor patch may be removed from the patient and inserted into the reader device to transfer the data from the sensor patch. In further embodiments, the reader device may contact the sensor patch as discussed further below. In still further embodiments, the reader may transfer data from the sensor patch wirelessly. The radiation dose received by the patient can be determined based on the obtained data (block 125).

In some embodiments of the present invention, the obtained data may include a voltage threshold of a metal-oxide semiconductor field-effect transistor (MOSFET) included on the at least one sensor patch 30. In these embodiments of the present invention, a pre-radiation voltage threshold of the MOSFET and a zero temperature coefficient of the MOSFET may be measured before the patient undergoes radiation therapy (block 108). The pre-radiation threshold voltage and the zero temperature coefficient of the MOSFET may be stored in the electronic memory of the at least one sensor patch (blocks 109 and 130). The stored zero temperature coefficient may be used to bias the MOSFET (block 124) on the at least one sensor patch 30 after the patient undergoes radiation therapy and before the post-radiation threshold voltage is measured as discussed further below.

It will be understood that the radiation dose may be automatically determined by the reader 75 without any input by a doctor or technician. However, in some embodiments of the present invention, the doctor or technician may be prompted for additional information (block 123) by the reader 75 to determine the radiation dose. For example, the reader 75 may prompt the technician for a correction factor related to the sensor patch 30 and/or, radiation type, equipment set-up and the like. The prompts may be carried out before and/or after the irradiation. Once the doctor or technician supplies the requested additional information, the reader 75 may automatically determine the radiation dose using the additional information provided. The obtained data, as well as other information, may be stored in an electronic memory (memory device) included on the sensor patch (block 130).

In particular, the electronic memory may include methodology data that instructs the reader 75 how to interface with, i.e., obtain data from, the sensor patch(es) 30. In particular, the electronic memory may include methodology data that instructs the reader 75 how to interface with, i.e., obtain data from, the sensor patch(es) 30. Thus, for example, if the patch 30 changes electronic configuration, the patch 30 can be configured to automatically instruct the reader 75 on how to obtain the radiation and other patch data of interest, allowing the reader 75 to operate with different versions of patches. In other embodiments, the reader 75 can be periodically upgraded with software to communicate with the different versions of patches. Combinations of these configurations may also be used.

The electronic memory may further include radiation-dose data, patient data, time and date of a radiation reading, calibration data and the like. Furthermore, as discussed above, the electronic memory may include the zero temperature coefficient of a MOSFET included on the sensor patch 30. This zero temperature coefficient may be used to bias the MOSFET after the radiation treatment before a post-radiation threshold voltage is obtained as discussed further below.

The sensor patch 30 does not require lead wires extending from a remote power source or computer system to operate (i.e., is basically inactive and/or unpowered) during irradiation. For example, where a MOSFET-based radiation sensor circuit is used, the MOSFET is generally passive but collects a permanent space charge as a result of the passage of ionizing radiation. After radiation exposure or at a desired evaluation time, the biosensor(s) can be inductively powered and the MOSFET-based radiation data can be wirelessly transferred to a remote reader.

Instead, the sensor patch 30 is configured to be a discrete patch(es) (or a patch array of sensors). In some embodiments, the patch 30 can transmit or relay radiation data upon contact with and/or insertion into a reader device 75 and may store data in an electronic memory device included on the sensor patch. As discussed above, in certain embodiments, the sensor patch 30 may be configured to communicate wirelessly with the reader 75. The radiation dose received by the sensor patch 30 can be determined and used to estimate the dose received by the patient during the radiation therapy session based on the data obtained by the reader. The reader 75 itself can be a handheld portable unit that may or may not require wires to connect with a remote controller or computer or may use a standard communication port as will be discussed further below. The reader 75 can include a user input such as a touch screen and/or keypad entry. In any event, the operations can be carried out for each or a selected radiation treatment session. If the operations are repeated for each treatment session, a cumulative amount of delivered radiation can be estimated/confirmed to allow a clinician to evaluate whether additional treatments are desired.

Figure 15A:
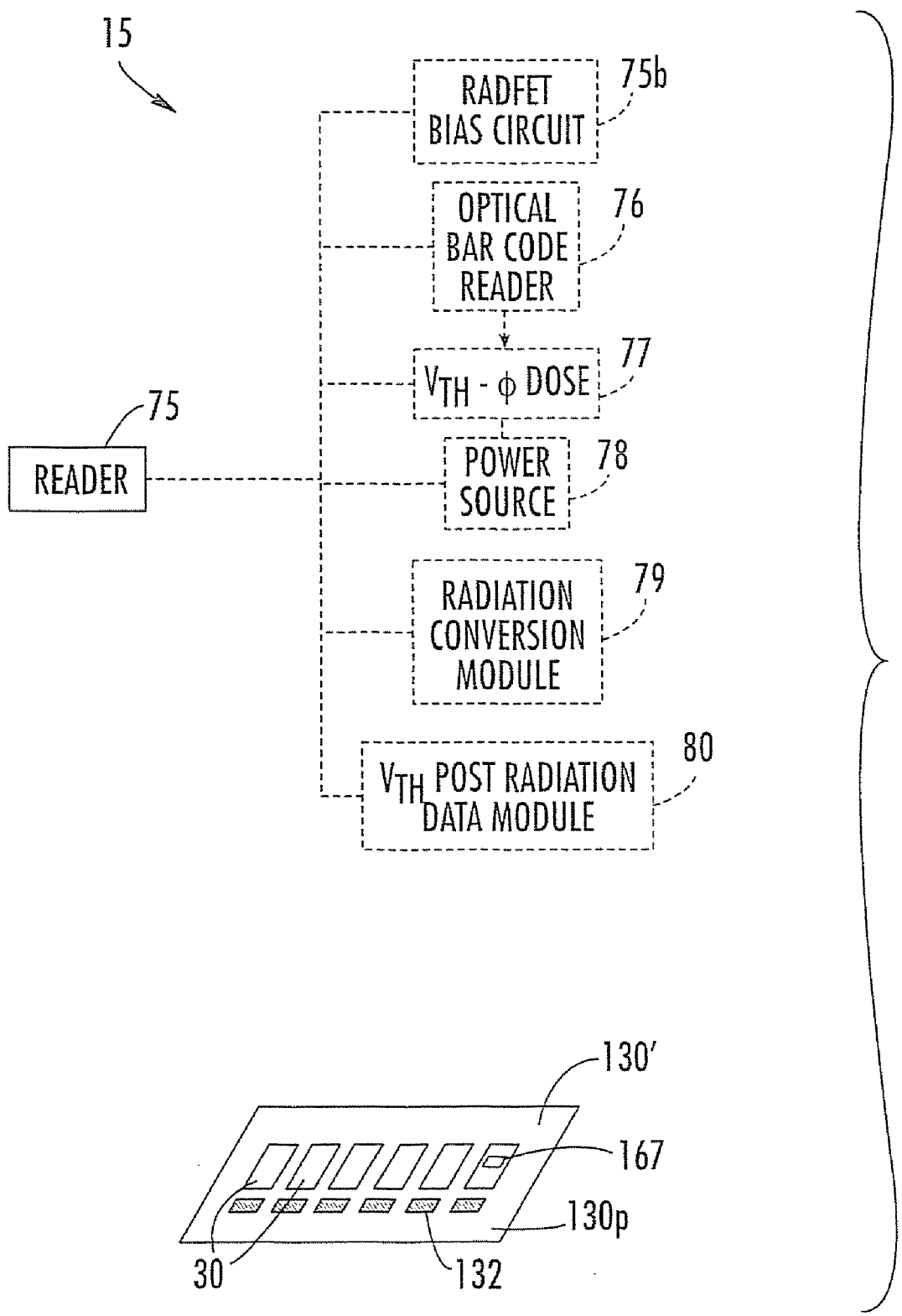
FIG. 15A is a schematic of a system or computer program product for estimating radiation based on data taken from a point contact-reader data acquisition system according to still further embodiments of the present invention.

FIG. 3A illustrates that the sensor patches 30 can be provided in a kit or set 130 including a plurality of sensors 30p. The plurality of sensors 30p may be configured in sufficient numbers or types for a single patient or so as to be able to supply sensors across a plurality of patients. In certain embodiments, a strip of six sensor patches 30 can be packaged together as a set 130' as shown in FIG. 15A. It is contemplated that, depending on the treatment type, the treatment location, the tumor site, and the like, different numbers of sensor patches 30 may be used for different patients. Thus, if the sensor kit 130 is sized for a single patient, the kit may include from about 2 to about 10 or more sensor patches 30 that can be selectively chosen for use by the clinician. Each sensor patch 30 can be sterilized and sealed in a sterile package or the kit 130 itself can be sized and configured to hold a plurality of the sensor patches 30p in a sterile package that, once opened, can be either used or discarded. Similarly, if the sensor kit 130 is sized for multi-patient use, then larger quantities may be packaged individually, or in sets within the multi-patient package, together. The sterilization can be performed by heat or chemical exposure, such as by ethylene oxide sterilization. In certain embodiments, sterilization and/or sterile packaging may not be required.

As is also shown in FIG. 3A, each sensor patch 30 can be packaged with pre-irradiation characterizing data 132. This data 132 can be included in optically or electronically readable formats such as in bar code format for the reader to be able to read without having the clinician enter the information into a controller/computer. In certain embodiments, the data 132 may be included in a memory storage device 67, for example, an electrically programmable memory such as an electrically erasable read only programmable memory (EEPROM), provided on each sensor patch 30p as discussed further below. The memory storage device 67 may include information such as patient identification, time, date, hospital, therapist, state of the device, dosed/undosed sensor data and calibration data. The memory storage device 67 may further be used to store bias parameters and/or information with respect to measurement methodology for each individual patch 30. For example, the measurement methodology may include instructions for the reader 75 on how to communicate with the sensor patch 30. Including these instructions in the memory storage device may allow the reader 75 to operate with any version of the sensor patch 30 as the reader 75 may not have to be configured for the specifications of a particular sensor patch 30. In some embodiments of the present invention, the memory storage device 67 of the sensor patch 30 may have at least 2 K of storage thereon.

Each sensor patch 30 can have an individual calibration coefficient, dose data or characterizing data label located on the sensor patch 30 or as a corresponding label held with the package or kit 130. In other embodiments, each sensor patch 30 produced in a common production run (off of the same wafer or chip) with substantially similar characterizing data may be packaged together and a single calibration characterizing data or label 132 can be included with the set 130 or sets or production run. In certain embodiments, the calibration related characterizing data can include the pre-irradiation threshold voltage value of a MOSFET(s) that is measured at an OEM and provided in or with the sensor patch set 130.

In further embodiments, the memory storage device 67 may include a zero temperature bias parameters associated with the MOSFET included on the sensor patch 30. The zero temperature coefficient of the MOSFET may be measured prior to administration of radiation therapy to the patient and stored in the memory storage device 67. The zero temperature coefficient of the MOSFET may be used to bias the MOSFET before obtaining a post-radiation threshold voltage value of the MOSFET as discussed further below.

Referring now to FIG. 19, Table 1 summarizes exemplary specifications for the sensor patch 30 according to some embodiments of the present invention. It will be understood that the specifications provided in Table 1 are provided for exemplary purposes only and that embodiments of the present invention should not be limited to this configuration.

In certain embodiments, identifying indicia may be disposed on the sensor patches 30 to allow a clinician to easily visually identify and/or account for the sensors used. For example, FIG. 3A illustrates three discrete sensor patches labeled as 1F, 2F, and 3F as well as a sensor with a pictorial representation of a heart 4F (other visual images can also be used such as a yellow caution sign, other anatomical symbols, and the like). In some embodiments of the present invention, the patches may be configured to accept direct indicia using, for example, a marker or a pen thereon. The heart or caution sensor patch 30s can be positioned in a radiation sensitive area to detect the amount of radiation delivered to that area. Typically, the radiation beam is adjusted to reduce the radiation exposure to sensitive areas and a caution-sensitive sensor patch 30s (or patches) can indicate whether adjustments need to be made to reduce the detected exposure for each or selected treatment sessions. The sensor patches 30s used for sensitive detection may be configured with increased sensitivity for enhanced dose resolution capability for measuring small, residual, or stray doses of radiation (such as those located over critical organs which are not in the treatment volume). For example, for "normal" single use sensors may be configured to operate over a range of between about 20-500 cGy; the "high sensitivity" sensor might be configured to operate from about 1-50 cGy. In particular embodiments, the circuit 30c (FIG. 9A) for the high sensitivity sensor 30s includes at least one radiation-sensitive field-effect transistor (RADFET) that can be configured to produce a larger threshold voltage shift for a given amount of received or absorbed dose relative to the sensors 30 positioned in the window of the targeted treatment volume. The larger voltage shift may increase dose resolution and possibly dose repeatability.

In addition, single-use dosimeters can be optimized to work over a much lower dose range than multiple use dosimeters. Since the typical per day fraction for radiation therapy is about 200 cGy, the dosimeter sensor 30 can be optimized for accuracy and repeatability over this dose range. A 20-500 cGy operating range should meet performance goals while providing adequate flexibility for varying treatment plans. A multiple-session fraction dosimeter sensor 30 may require a much larger dose range that depends on the number of fractions over which the sensor will operate. As used herein, "disposable" means that the sensor patch is not reusable and can be disposed of or placed in the patient's records.

As shown in FIG. 3A, the indicia can include an alphanumeric identifier such as the letter "F" located to be externally visible on the sensor patches 30. The letter "F" can represent that the sensors are placed on a first side or front of the patient. FIG. 3B illustrates that a second set of sensors 130' can be supplied, these sensor patches 30 can be labeled with different indicia, such as 1B, 2B, 3B and the like, representing that they are located at a different location relative to the first set (such as a second side or back of the patient). Using data from opposing outer surfaces can allow an interpolated radiation dose amount to be established for the internal tumor site.

It will be understood that the indicia described above, namely "F" and "B", are provided herein for exemplary purposes only and that indicia according to embodiments of the present invention are not limited by the examples provided. Any label, mark, color or the like may be used that would serve to distinguish one patch or set of patches from another patch or set of patches without departing from the teachings of the present invention. For example, instead of "F" and "B", the first set of patches 130 may be blue and the second set of patches 130' may be red. Furthermore, the indicia may be, for example, on the sensor patch itself or on an adhesive covering placed on or over the sensor patch without departing from the teachings of the present invention.

FIG. 3C illustrates a patient anatomical map 150 that can be used to identify where each of the sensor patches 30 are placed on the body of the patient. The map 150 may be stored in the patient chart or file. For each treatment session for which dose monitoring is desired, the clinician can allocate the same sensor patch identifier ("A", "1F", etc. . . . ) to the same location. The map 150 and/or indicia on the sensor patches 30 can, in turn, help the clinician consistently identify whether a particular location may have undue or deficient exposure. For example, if sensor patch F1 indicates a low radiation exposure, while F3 indicates a relatively high exposure, and the two are positioned in the targeted beam region, either one or both of the sensor patches 30 is not functioning properly, or the radiation beam may need adjustment. Using substantially the same sensor patch position for successive treatment sessions may allow cumulative radiation dose data to be obtained and correlated to provide a more reliable indication of dose. The clinician may also draw markings on the patient's skin to help align the sensor patches 30 in relation thereto over the different treatments sessions.

In certain embodiments, the discrete sensor patches 30 can be arranged to reside on a common substrate or to be attached to each other so as to define known or constant distances therebetween (not shown). The sensor patches 30 may be configured to be at the body temperature of the patient during use or at room temperature, or temperatures in between. In certain embodiments, to establish a calculated dose amount, a temperature reading may be obtained, assumed, or estimated. In certain particular embodiments, the temperature may impact the operational change if substantially different from that upon which the calibration data is established. In some embodiments, the at least one sensor patch 30 can be used with other therapies that generate radiation and potentially expose a patient to radiation. For example, but not limited thereto, at least one sensor patch 30 can be mounted to a patient during a fluoroscopic procedure to evaluate the skin radiation exposure.

In certain embodiments, a first set-up pre-dose verification protocol can be carried out to deliver a first radiation dose and a first radiation dose value can be obtained for at least one selected patch to confirm that the radiation beam focus location is correct or suitable (or whether a sensitive area is receiving radiation). In addition, the system can be configured to map a dose gradient by correlating the determined radiation dose values at each patch location to the anatomical location on the subject of each patch.

Figure 4:
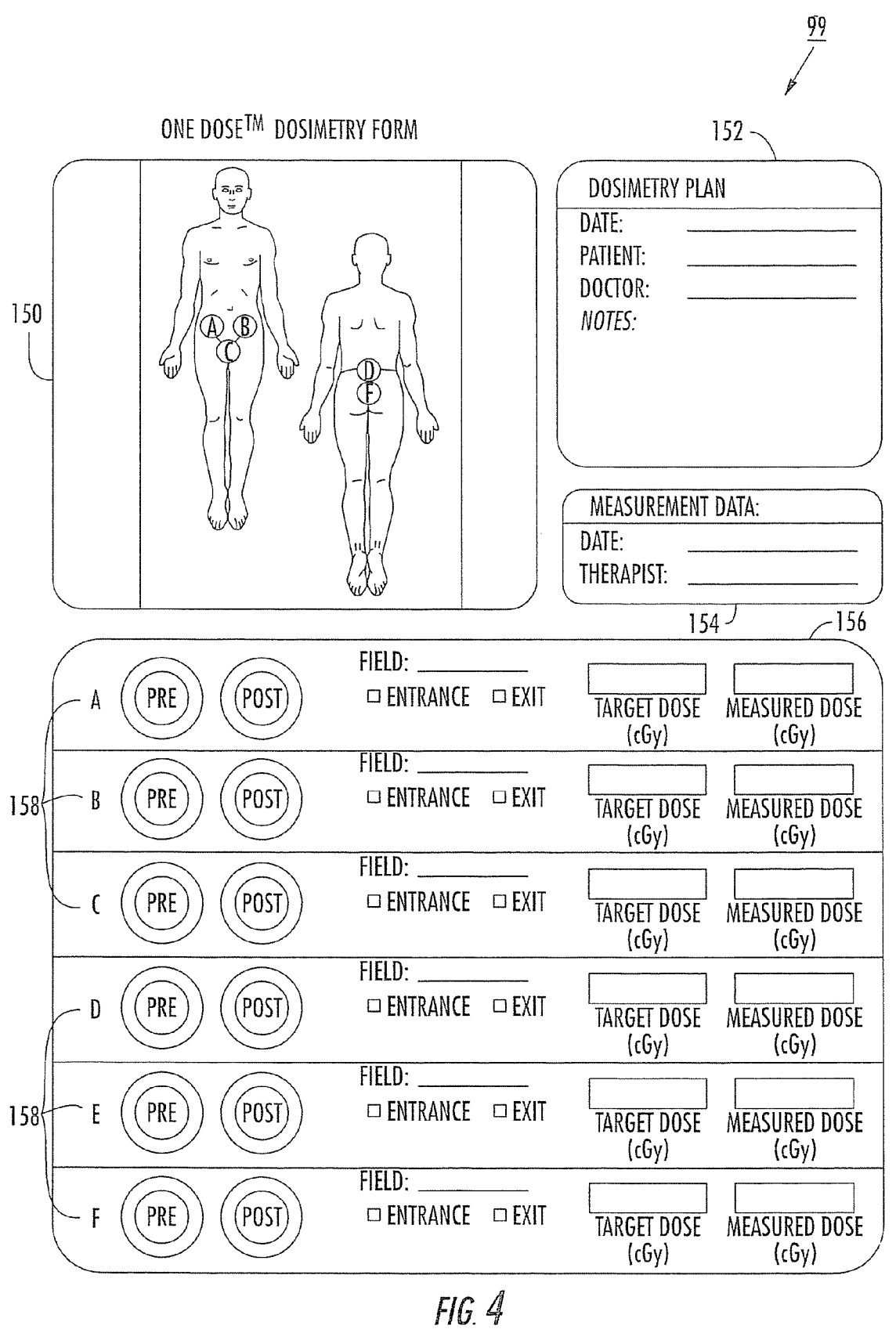

FIG. 4 illustrates an exemplary patient dosimetry form 99, which may be, for example, a paper sheet or computer printable document. The form 99 can contain an anatomical map 150 as discussed above with respect to FIG. 3C. Sicel Technologies, Inc. asserts copyright protection for the form illustrated in FIG. 4 and has no objection to reproduction of the patent document, as it appears in the Patent and Trademark Office patent file or records, but reserves all other rights whatsoever.

As discussed above, the map 150 may be used to identify and/or memorialize for the patient record where each of the sensor patches 30 are placed on the body of the patient during use. An anatomical map 150 can be used to record the specifics of each radiation session and may be placed in each patient's chart or file to assist the doctor and/or clinician. Patients being treated on an ongoing basis may have multiple dosimetry forms 99 in their chart and/or file corresponding to each treatment session. As noted above, for each treatment session, the clinician can, as desired, allocate the same sensor patch identifier to the same location aided by the map 150. As further illustrated in FIG. 4, the dosimetry form 99 may further include a dosimetry plan portion 152, a measurement data portion 154 and a sensor patch record portion 156.

The dosimetry plan portion 152 may include the patient's name, the date or dates the patient is scheduled for the treatment, the patient's doctor, and any information that may be specific to the patient or the patient's treatment. The measurement data portion 154 may include information such as the date of the treatment and the therapist administering the treatment on that date. The sensor patch record portion 156 may include labeled sections 158 (A, B, . . . ) giving each patient a discrete identifier which may correspond to sensor patch locations (A, B, . . . ) with the identifiers indicated on the anatomical map 150. The sensor patch record portion 156 may further include dosing data, for example, target and measured doses as illustrated in FIG. 4. The sensor patch record portion 156 may further include the actual sensor patch used on the patient in each of the labeled sections 158. As shown, the form 99 can include two separate storage regions, namely a pre and post dose use storage region. In addition, the form 99 can also allow a clinician to indicate whether the sensor patch was held in the entrance and/or exit field.

In certain embodiments, the sensor patch 30 may contain a storage or memory device 67 (FIGS. 3A, 9B), the storage or memory device on the sensor patches may be accessed to determine dosing information etc. if this information fails to be recorded, is misplaced or requires verification. Furthermore, the memory device 67 included on the sensor patch 30 may further include the data recorded in the map portion 150, the dosimetry plan portion 152 and the measurement data portion 154 of the dosimetry form 99. Accordingly, the memory device 67 on the sensor patch 30 may serve as an electronic dosimetry patient record form. It will be understood that the dosimetry form 99 of FIG. 4 is provided for exemplary purposes only and that the present invention may provide data and/or hold sensor patches in alternate manners without departing from the teachings of the present invention.

Figure 5A:
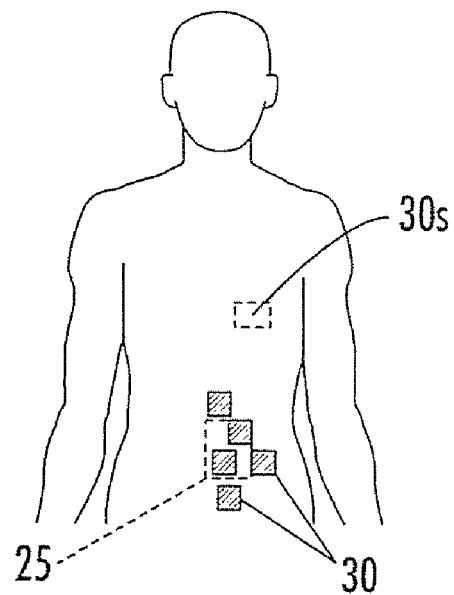
FIGS. 5A and 5B are schematic illustrations of sensor placement on a patient according to further embodiments of the present invention.
Figure 5B:
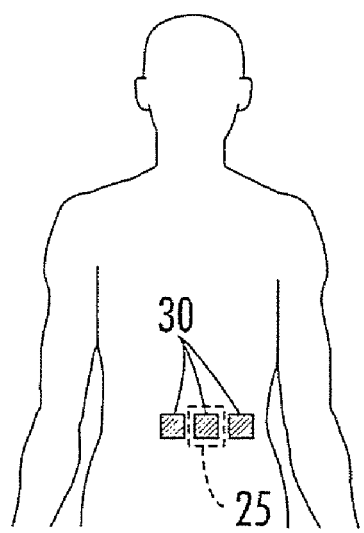

FIG. 5A illustrates the use of five primary sensor patches 30 positioned over the targeted treatment region (on the front side of the patient) and one sensor patch 30s positioned over the heart. FIG. 5B illustrates three primary sensors 30 located over the back surface proximate the area corresponding to the underlying tumor site 25.

Figure 6:
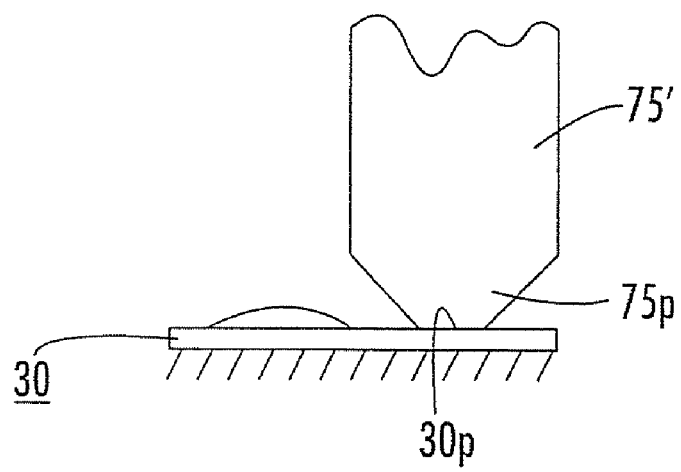
FIG. 6 is a schematic illustration of embodiments of a reader contacting the sensor to obtain the radiation dosage data according to still further embodiments of the present invention.

FIG. 6 illustrates a reader or data acquisition device 75' according to embodiments of the present invention, in point contact with the underlying sensor patch 30 in order to detect the amount of radiation that the sensor patch 30 was exposed to during (or after) the treatment session. In certain embodiments, as discussed above, the sensor patch(es) 30 can be secured to a patient's chart or dosimetry form 150 and read after removal from the patient. The reader 75' illustrated in FIG. 6 may be configured to contact a portion of an electrical circuit on the sensor patch 30 that includes a device that has an operating characteristic or parameter that changes upon exposure to radiation in a predictable manner to allow radiation doses to be determined. The reader 75' can be configured with a probe 75p that is configured to electrically contact an electrically conductive probe region on the sensor patch 30 so as to obtain a reading in a "short" time of under about 30 seconds, and typically in less than about 5-10 seconds, for each of the sensor patches 30.

Figure 7A:
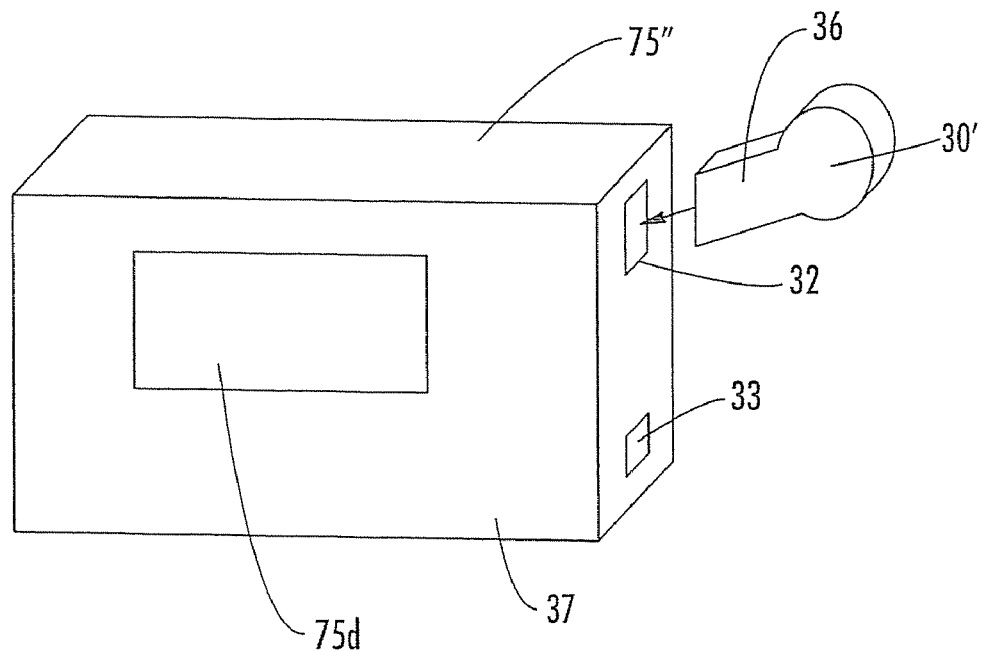
FIG. 7A is a schematic illustration of further embodiments of a reader receiving the sensor in a sensor port to obtain the radiation dosage data according to some embodiments of the present invention.

Referring now to FIG. 7A a sensor patch 30' disposed in a reader or data acquisition device 75" according to further embodiments of the present invention. Sensor patches 30' according to embodiments of the present invention may be adapted to be inserted into the reader 75". Similarly, the reader 75" is adapted to receive the sensor patch 30'. As shown, the sensor patch 30' is formed to include a tab portion 36 that at least a portion of is sufficiently rigid to sustain its shape for proper electrical coupling when inserted into a port 32 in the reader device 75". As further illustrated in FIG. 7A, the reader 75" may include a sensor port 32 and the sensor patch 30' may be inserted into the port 32 in the reader 75" in order to detect the amount of radiation that the sensor patch 30' was exposed to. The port 32 can read the sensor patch 30' as it is held in selected orientations in the port 32. The port 32 may be configured similar to conventional devices that read, for example, glucose strip sensors and the like. The port 32 illustrated in FIG. 7A may contain one or more electrical contacts configured to contact one or more electrical contacts on the sensor patch 30' to electrically connect the reader 75" to an electrical circuit on the sensor patch 30'. The electrical circuit on the sensor patch 30' includes a radiation-sensitive component that has an operating characteristic or parameter that changes upon exposure to radiation in a predictable manner to allow radiation doses to be determined. As before, the reader 75" may obtain a reading in under about 30 seconds, and typically in less than about 5-10 seconds, for each of the sensor patches 30.

Figure 15B:
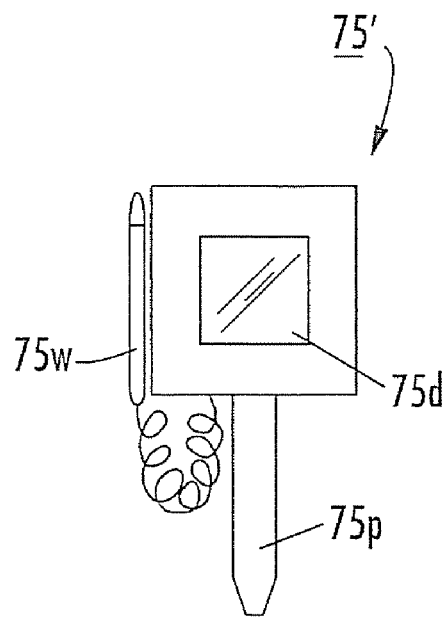
FIG. 15B is a block diagram illustrating a reader device according to some embodiments of the present invention.

The reader device 75" can be held in a portable housing 37. It may be pocket sized and battery powered. In certain embodiments, the reader device 75 may be rechargeable. As shown in FIGS. 7, 15A and 15B, the reader 75 may include a display portion 75d, for example, a liquid crystal display (LCD), to provide an interface to depict data to the doctor and/or technician.

The function of the reader device 75 may be incorporated into any portable device adapted to receive a sensor patch 30 in, for example, a sensor port 32. For example, the reader 75 functionality/circuitry could be disposed in a personal digital assistant (PDA) that is adapted to include a radiation sensor port 32. The reader 75 may further include a remote computer port 33. The port 33 may be, for example, RS 232, infrared data association (IrDA) or universal serial bus (USB), and may be used to download radiation and/or other selected data from the sensor patch 30 to a computer application or remote computer.

Figure 7B:
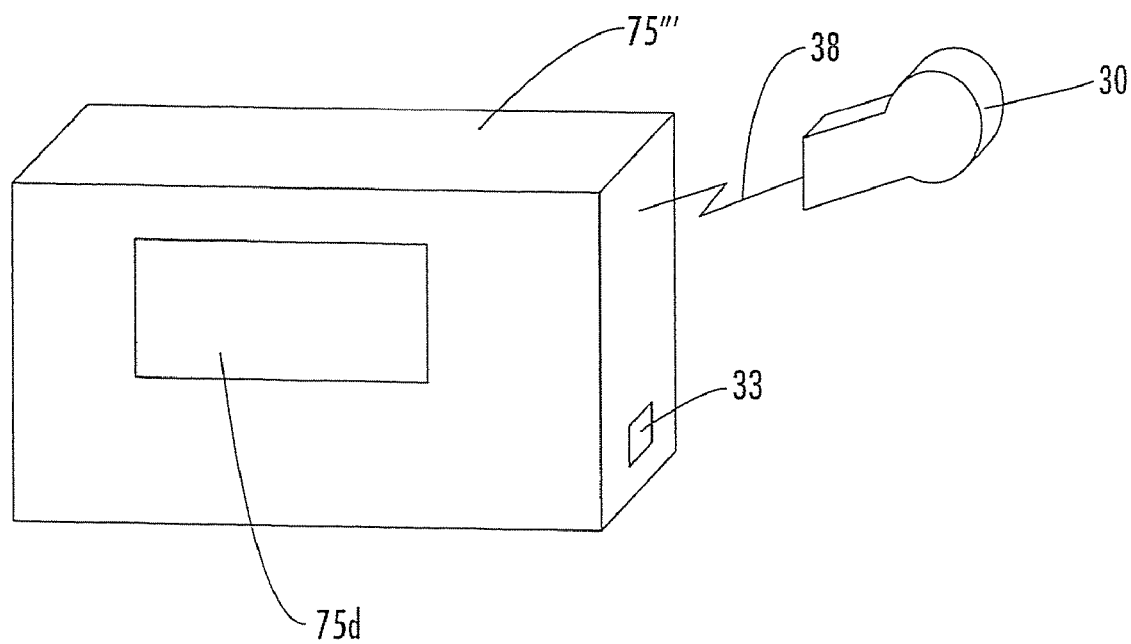
FIG. 7B is a schematic illustration of still further embodiments of a reader receiving wireless communications from the sensor to obtain the radiation dosage data according to further embodiments of the present invention.

As illustrated in FIG. 7B, in some embodiments, the sensor patch 30 and the reader device 75''' may both be equipped with a radio frequency (RF) interface and information may be shared between the reader device 75''' and the sensor patch 30 using wireless signals 38 without departing from the scope of the present invention. Exemplary embodiments of a reader 75 according to embodiments of the present invention are provided in commonly assigned U.S. Design patent application Ser. No. 29/197,934 entitled Portable Oncologic External Dosimeter Reader, filed Jan. 21, 2004, the content of which are hereby incorporated herein by reference as if set forth in its entirety.

In certain embodiments, as noted above, the sensor patch 30 includes a storage or memory device 67. In these embodiments, the reader 75 may be configured to obtain data stored in the memory device 67 of the sensor patch 30 using, for example, electrical contacts on the reader 75 and the patch 30, to transfer the data stored in the memory device 67 of the sensor patch 30. This data obtained from the sensor patch memory device 67 may, for example, be stored locally on the reader 75 or be downloaded to an application on, for example, a remote computer using a port 33 provided in the reader 75. The memory device 67 on the sensor patch 30 may serve as a permanent record of the radiation dose and may contain a real time clock such that the obtained data may include a time and date stamp.

Figure 20:
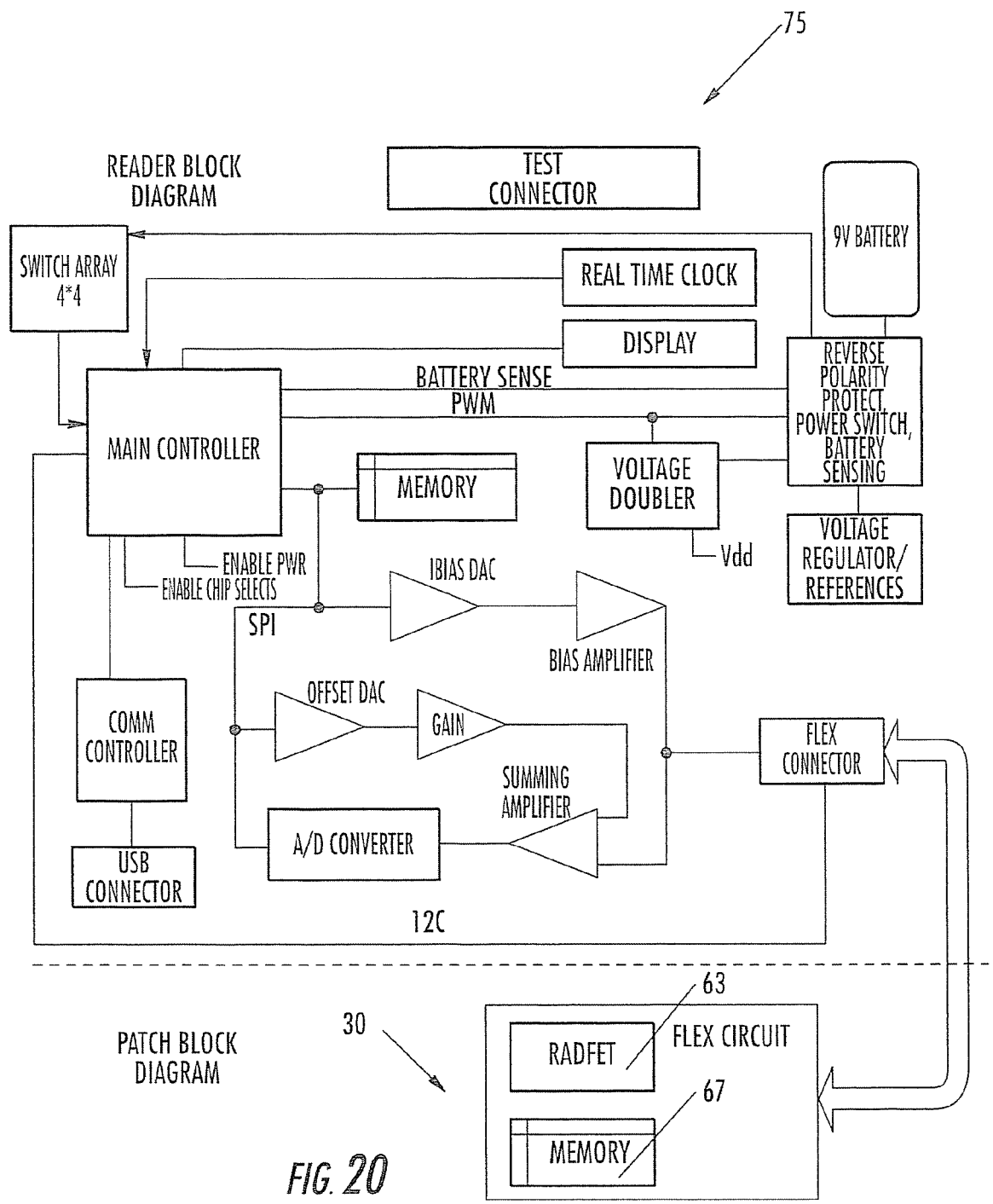
FIG. 20 is a block diagram illustrating functions of a reader device and a patch according to some embodiments of the present invention.
Figure 21:
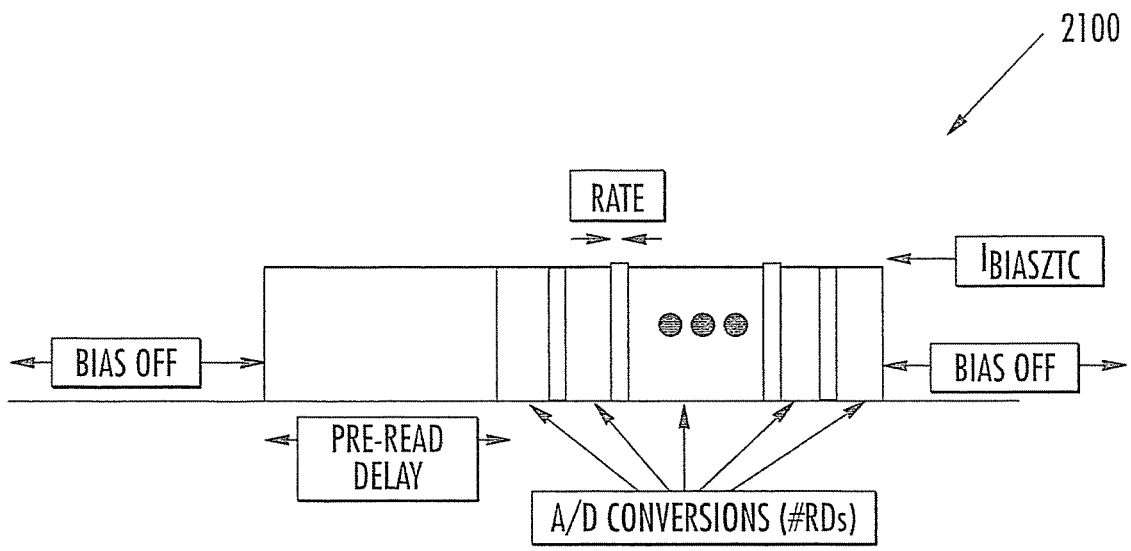
FIG. 21 is a block diagram illustrating a process for modifying conversion parameters and bias timing according some embodiments of the present invention.

An exemplary block diagram of a reader 75 and a sensor patch 30 including a RADFET 63 and an electronic memory 67 according to some embodiments of the present invention is provided in FIG. 20. It will be understood that the block diagram of the reader 75 and the sensor patch 30 of FIG. 7B is provided for exemplary purposes only and embodiments of the present invention should not be limited to the configuration provided therein. Furthermore, a flow diagram 2100 of FIG. 21 illustrates how a number of reads, a read delay and/or a rate may modify conversion parameters of the RADFET according to some embodiments of the present invention.

Figure 8A:
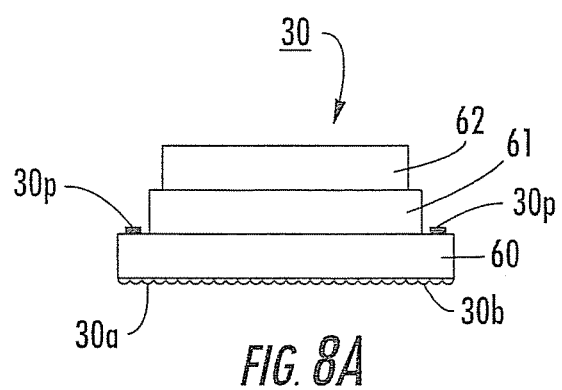
FIG. 8A is a greatly enlarged side view of a disposable radiation dosimeter according to still further embodiments of the present invention.

FIG. 8A illustrates exemplary embodiments of a sensor patch 30. As shown, the sensor patch 30 includes a substrate layer 60, a circuit layer 61, and an upper layer 62 that may be defined by a coating, film, or coverlay material. The substrate layer 60 can be selected such that it is resilient, compliant, or substantially conformable to the skin of the patient. Examples of suitable substrate layer materials include, but are not limited to, Kapton, neoprene, polymers, co-polymers, blends and derivatives thereof, and the like. The underside or bottom of the sensor patch 30b may include a releasable adhesive 30a so as to be able to attach to the skin of the patient. The adhesive 30a can be a medical grade releasable adhesive to allow the sensor patch 30 to be secured to the skin during the treatment session and then easily removed without harming the skin. The adhesive 30a can be applied to portions, or all, of the bottom surface of the substrate layer 60. A releasable liner can be used to cover the adhesive, at least prior to positioning on the patient. In certain embodiments, the underside of the sensor patch 30b may be free of the adhesive. In these embodiments, an adhesive coverlay 30cl (FIG. 9C) may be placed over the body of the sensor patch 30 to secure the sensor patch 30 to the patient. The adhesive coverlay 30cl may be sized to extend beyond the outer perimeter of the sensor substrate 60. The adhesive may be on a portion or all of the underside of the coverlay 30cl.

In other embodiments, the sensor patch(es) 30 is configured as a discrete, low profile, compact non-invasive and minimally obtrusive device that conforms to the skin of the patient. The sensor patch(es) may be less from about 0.25 to about 1.5 inches long and wide and have a thin thickness of from about 1 to about 5 mm or less. As such, the sensor patches 30 can, in certain particular embodiments, be secured to the patient and allowed to reside thereon for a plurality or all of the successive treatments. For example, the sensor patches 30 can be configured to reside on the patient in its desired position for a 1-4 week, and typically about a 1-2 week period. In this manner, the same sensor patches 30 can be used to track cumulative doses (as well as the dose at each treatment session). An adhesive may be applied in a quantity and type so as to be sufficiently strong to withstand normal life functions (showers, etc.) during this time. Of course, selected ones of the sensor patches 30 can also be replaced as desired over the course of treatment as needed or desired.

In certain embodiments of the present invention, the sensor patch 30 can be attached to the patient so that it makes and retains snug contact with the patient's skin. Air gaps between the sensor 30 and the patient's skin may cause complications with respect to obtaining the estimated dosage data. As illustrated in FIGS. 9D and 9E, some embodiments of the present invention include the placement of an overlay material 30fl over the sensor patch 30 to, for example, simulate placement of the sensor patch 30 beneath the patient's skin. This type of simulation may inhibit scatter of the radiation beam and/or establish electronic equilibrium in proximity to the sensor patch 30 and, therefore, increase the reliability of radiation measurement. Radiation measurement using the sensor subsurface electronics may be optimal at from about 0.5 to about 3 cm beneath the patient's skin, but typically is from about 1 to about 1.5 cm beneath the patient's skin. Accordingly, the overlay material 30fl may be from about 0.5 to about 3 cm thick to simulate subsurface depth measurement conditions. The presence of this overlay material 30fl may decrease the influence of air gaps between the sensor 30 and the patient's skin.

The overlay material 30fl may be, for example, a resilient flubber like or flexible material that will conform to the skin such as an elastomeric or the like. As illustrated in FIG. 9D, the overlay material 30fl may be placed between the adhesive coverlay 30cl and the sensor patch 30 such that the adhesive coverlay 30cl adheres the sensor patch 30 and the overlay material 30fl to the patient's skin. As illustrated in FIG. 9E, the overlay material 30fl may be placed over the adhesive coverlay 30cl and the sensor patch 30. In certain embodiments, the overlay material may have adhesive properties such that the overlay 30fl may be adhered to the patient's skin. The overlay material 30fl may also be integrated with the sensor patch 30 without departing from the teachings of the present invention.

As further illustrated in FIGS. 18A and 18B, some embodiments of the present invention include the placement of a buildup cap 180 over the sensor patch 30 to, for example, simulate placement of the sensor patch 30 beneath the patient's skin. This type of simulation may help to focus a narrow portion of the radiation beam in proximity to the sensor patch 30 and, therefore, increase the reliability of radiation measurement. As further illustrated in FIG. 18A, the buildup cap 180 may have a hemispherical shape and may simulate placement of the sensor patch 30 inside the body to a depth called "Dmax". Dmax may be, for example, from about 1 to about 3 cm and is the depth at which the absorbed dose reaches a maximum for a given energy. The buildup cap 180 may include a material equivalent to water and a metallic material. For example, the buildup cap 180 may include a layer of polystyrene 182 having a diameter of from about 6 to about 7 mm and a layer of copper 181 on the polystyrene have a thickness of about 0.5 to about 1 mm.

The buildup cap 180 may include a small lip (not shown) that hooks onto the front edge of the patch for consistent alignment. The buildup cap 180 may have a medical grade adhesive that would stick well, but not permanently, to the top face of the sensor patch 30. In some embodiments of the present invention, the geometry of the cap could be made to help with isotropy. The buildup cap 180 may be placed on the sensor patch 30 separately based on the energy range of the buildup cap 180, thereby allowing the underlying sensor patch 30 to be used with different buildup caps 180 for different energy ranges. In some embodiments of the present invention, the buildup caps 180 may be provided in different colors, the colors indicating the energy range of the buildup cap 180. Thus, in some embodiments of the present invention, the bulk of the buildup cap 180 may be injection molded polystyrene 182 that is coated with a copper layer 181 and some rubbery or elastomeric surface paint applied in different colors corresponding to the different energy ranges provided by the buildup cap 180. The buildup cap 180 can also be shaped to provide a measurement that is independent of X-ray beam entry angle.

It will be understood that the buildup cap 180 may be placed between the adhesive coverlay 30cl and the sensor patch 30 such that the adhesive coverlay 30cl adheres the sensor patch 30 and the buildup cap 180 to the patient's skin. It will be further understood that the buildup cap 180 may also be placed over the adhesive coverlay 30cl and the sensor patch 30 without departing from the scope of the present invention Still referring to FIG. 8A, the sensor circuit layer 61 can be attached to, and/or formed on, the underlying substrate layer

60. The upper layer 62 can be configured as a moisture inhibitor or barrier layer that can be applied over all, or selected portions of, the underlying circuit layer 61. It is noted that, as shown, the thickness of the layers 60-62 are exaggerated for clarity and shown as the same relative thickness, however the thickness of the layers may vary. In certain embodiments, the sensor patch 30 is configured as a low profile, thin device that, when viewed from the side, is substantially planar.

Figure 8B:
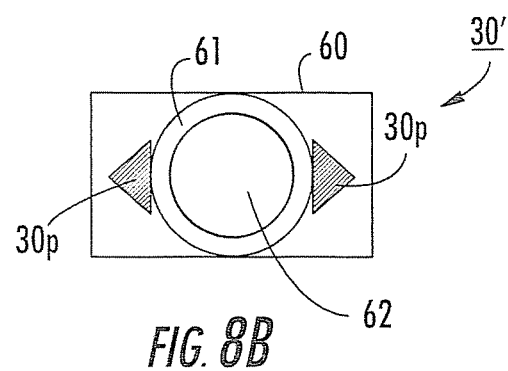
FIG. 8B is a top view of the dosimeter shown in FIG. 8A.

FIG. 8B is a top view of embodiments of a sensor patch 30. As shown, in certain embodiments, the circuit layer may include two conductive probe contacting regions 30*p*. During data readings/acquisitions, the probe contacting regions 30*p* are configured to provide the connections between the operating circuitry on the circuit layer 61 and the external reader. The probe contacting region(s) 30*p* can be directly accessible or covered with a protective upper layer 62. If directly accessible, during operation, the reader 75 can merely press against, contact or clip to the sensor patch 30 to contact the exposed surface of the conductive probe region 30*p* to obtain the reading. If covered by an upper layer 62 that is a protective coating or other non-conductive insulator material, the clinician may need to form an opening into the coating or upper layer over the region 30*p* so as to be able to penetrate into the sensor patch 30' a certain depth to make electrical contact between the probe region 30*p* and the probe of the reader 75*p*.

Figure 8C:
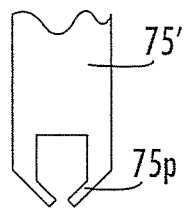
FIG. 8C is a partial cutaway view of a probe head for a reader according to some embodiments of the present invention.

FIG. 8C illustrates a probe portion 75*p* of the reader 75' of FIG. 6. As illustrated, the probe portion 75*p* may be configured so that the probe 75*p* includes, for example, conductive calipers, pinchers, or other piercing means, that can penetrate to make electrical contact with the probe contacting region 30*p* of the sensor patch.

Figure 9A:
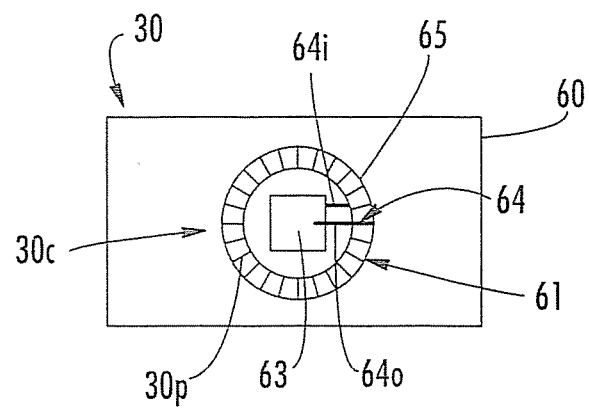
FIG. 9A is a schematic of embodiments of a sensor patch with a circuit thereon according to further embodiments of the present invention.

FIG. 9A illustrates a top view of embodiments of a circuit layer 61. As shown, the circuit layer 61 includes the radiation sensitive operative sensor patch circuitry 30*c* that is self-contained and devoid of outwardly extending or hanging lead wires that connects to an operational member. The sensor patch circuitry 30*c* includes a radiation sensitive device 63 that exhibits a detectable operational change when exposed to radiation. In certain embodiments, the radiation sensitive device 63 is a miniaturized semiconductor component such as a MOSFET. Suitable MOSFETs include RADFETs available from NMRC of Cork, Ireland. In certain embodiments, the MOSFET may be sized and configured to be about 0.5-2 mm in width and length. The circuitry 30*c* also includes at least one conductive lead or trace 64 extending from the radiation sensitive device 63 to the conductive probe contacting region 30*p*. In the embodiment shown, the conductive probe contacting region 30*p* is an annular ring. As also shown there are two traces 64*i*, 64*o* that connect the device 63 to the ring 30*p*. The traces or leads 64' may be formed, placed, or deposited onto the substrate layer 60 in any suitable manner including, but not limited to, applying conductive ink or paint or metal spray deposition on the surface thereof in a suitable metallic pattern, or using wires. As desired, an upper layer 62 such as described above (such as epoxy) may be formed over the circuit layer 61 (or even the entire sensor patch). The sensor patch 30 may include integrated Electro Static Discharge (ESD) protection, the reader 75 may include ESD protection components, or the user/operator may use ESD straps and the like during readings.

In particular embodiments, the sensor patch 30 and circuit 30*c* can be configured with two or more MOSFETS. In embodiments configured to have two MOSFETS, one may be positioned over the other on opposing sides of the substrate in face-to-face alignment to inhibit orientation influence of the substrate. (not shown). Additionally, other materials, e.g., certain epoxies, can be used to both encapsulate the MOSFETs and provide further scattering influence to facilitate isotropic response of the MOSFETs. In addition, there are well known influences of radiation backscatter from the surface of patients on whom surface-mounted dosimeters are used. The backscatter effect can be taken into account when calculating an entrance or exit dose or sufficient build-up may be provided on the top of the dosimeter to promote the equilibration of scattered electrons. See, *Cancer, Principles and Practice of Oncology,* 3d edition, ed. V T DeVita, S. Hellman, and S A Rosenberg (JB Lippincott Co., Phila., 1989), the contents of which are hereby incorporated by reference as if recited in full herein.

Figure 9B:
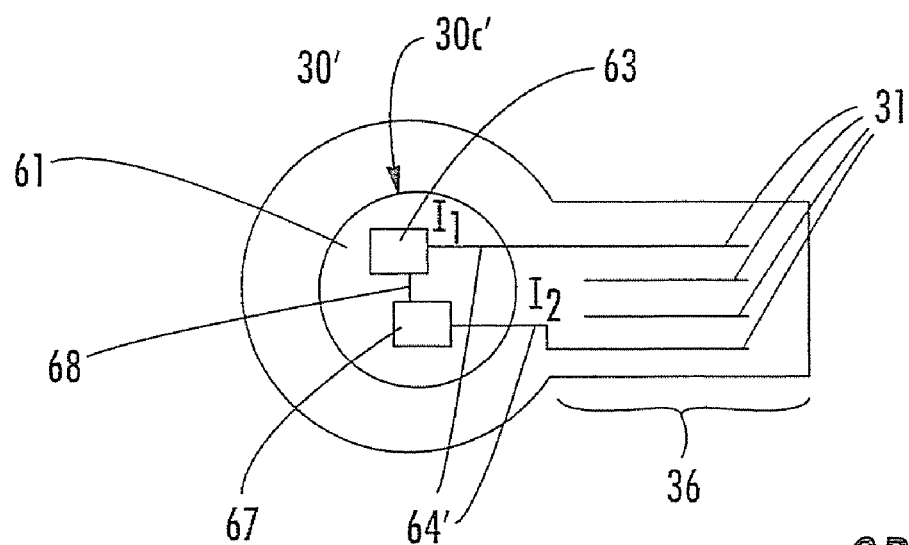
FIG. 9B is a schematic of further embodiments of a sensor patch with a circuit thereon according to still further embodiments of the present invention.

FIG. 9B is a top view of further embodiments of a sensor patch 30' that includes a tab portion 36 that is adapted to be received by a reader, for example, reader 75" illustrated in FIG. 7. As shown, the circuit 30*c'* includes a circuit layer 61 that includes at least one electrical contact 31 shown as a plurality of substantially parallel leads. During data readings/acquisitions, the sensor patch 30' is inserted into the reader port 32 of the reader 75" (FIG. 7) and the at least one electrical contact 31 is configured to provide the electrical connections between the operating circuitry on the circuit layer 61 and the external reader 75". The electrical contact(s) 31 may be covered with a protective upper layer 62 (FIG. 8A). If covered by an upper layer 62 that is a protective coating or other non-conductive insulator material, the clinician may need to form an opening into the coating or upper layer over the electrical contact(s) 31 so these contact(s) 31 may make electrical contact with the reader via sensor port 32 (FIG. 7).

FIG. 9B further illustrates the circuit layer 61 that includes the radiation sensitive operative sensor patch circuitry 30*c'*. The sensor patch circuitry 30*c'* includes a radiation sensitive device 63 that exhibits a detectable operational change when exposed to radiation and may include a memory device 67. In certain embodiments, the radiation sensitive device 63 is a miniaturized semiconductor component such as a MOSFET. Suitable MOSFETs include RADFETs available from NMRC of Cork, Ireland. In certain embodiments, the MOSFET may be sized and configured to be about 0.5-2 mm in width and length. The circuitry 30*c'* also includes at least one conductive lead or trace 64' extending from the radiation sensitive device 63 and/or the memory device 67 to the at least one electrical contact(s) 31. The traces or leads 64' may be formed, placed, or deposited onto the substrate layer 60 in any suitable manner including, but not limited to, applying conductive ink or paint or metal spray deposition on the surface thereof in a suitable metallic pattern, or using wires. As desired, an upper layer 62 such as described above (such as epoxy) may be formed over the circuit layer 61 (or even the entire sensor patch). Each sensor patch 30 may be from about 0.25 to about 1.5 inches long and wide and have a thin thickness of from about 1 to about 5 mm or less.

Figure 9C:
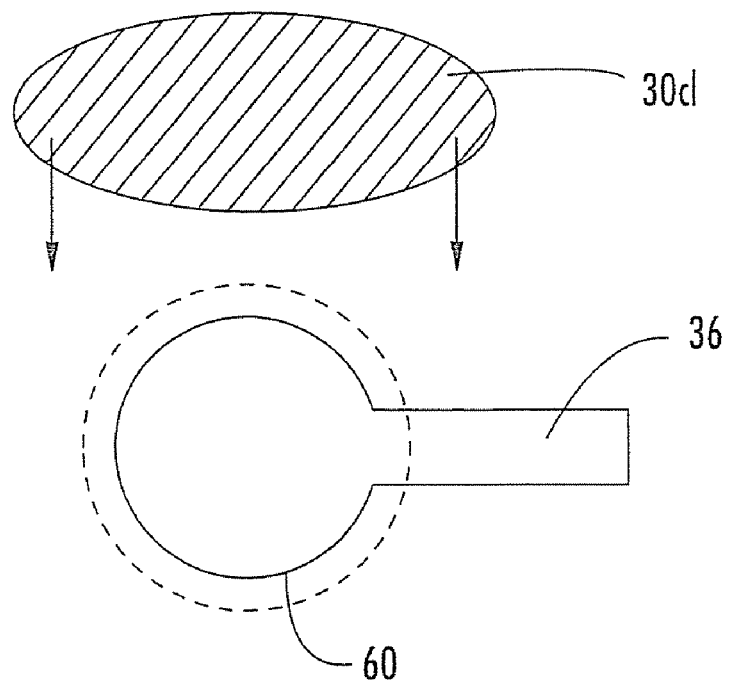
FIG. 9C is a schematic of further embodiments of a sensor patch with a circuit thereon according to some embodiments of the present invention.
Figure 9D:
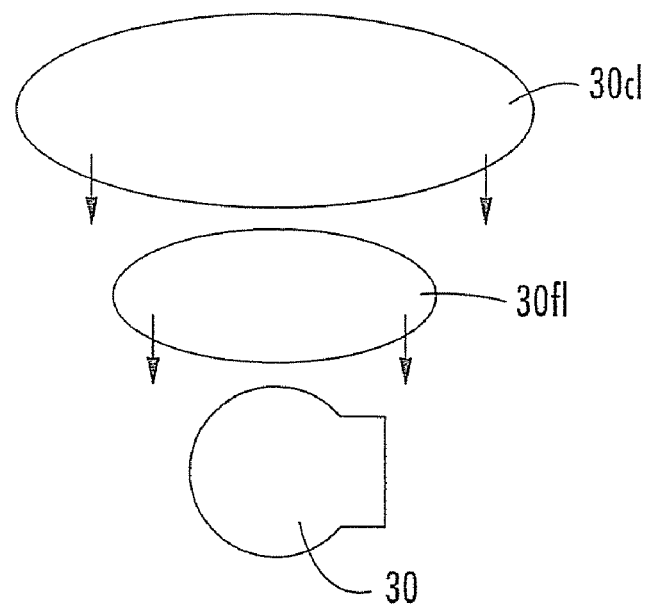
FIG. 9D is a schematic of further embodiments of a sensor patch according to further embodiments of the present invention.
Figure 9E:
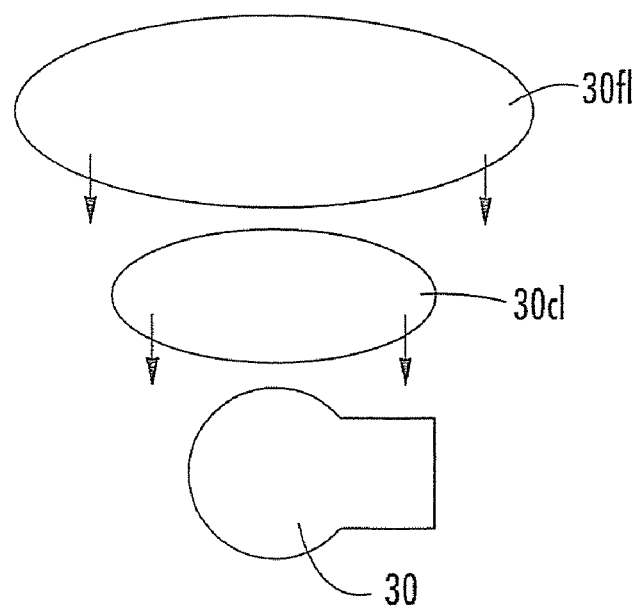
FIG. 9E is a schematic of further embodiments of a sensor patch according to still further embodiments of the present invention.

As discussed above with respect to FIG. 8A, the underside or bottom of the sensor patch 30*b* may include a releasable adhesive 30*a* so as to be able to attach to the skin of the patient. The adhesive 30*a* can be a medical grade releasable adhesive to allow the sensor patch 30 to be secured to the skin during the treatment session and then easily removed without harming the skin. The adhesive 30*a* can be applied to portions, or all, of the bottom surface of the substrate layer 60. Referring now to FIG. 9C, in certain embodiments, the underside of the sensor patch 30*b* may be free of the adhesive. As illustrated, an adhesive coverlay 30*cl* may be placed over the entire body of the sensor patch 30 to secure the sensor patch 30 to the patient. As further illustrated, the adhesive coverlay 30*cl* may be sized to extend beyond the outer perimeter of the sensor substrate 60 and leave the tab portion 36 of the sensor 30' exposed. The adhesive provided on the underside of the coverlay 30*cl* may be provided on a portion of the coverlay 30*cl*, for example, the portion of the coverlay 30*cl* contacting the patient's skin outside the perimeter of the sensor substrate 60, or on the entire underside of the coverlay 30*cl*.

Figure 10A:
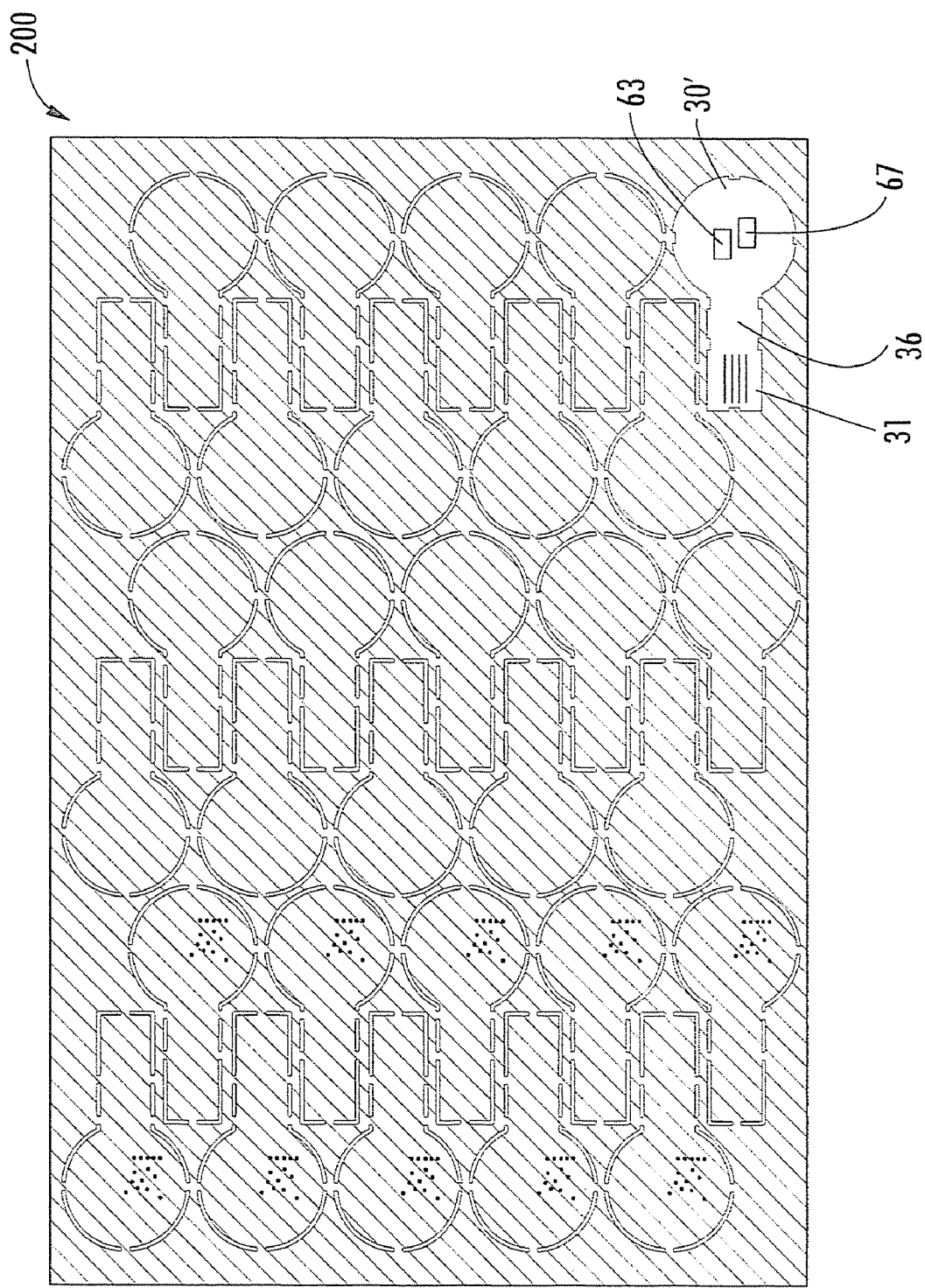
FIG. 10A is a schematic illustration of a sheet of sensors according to some embodiments of the present invention.
Figure 10B:
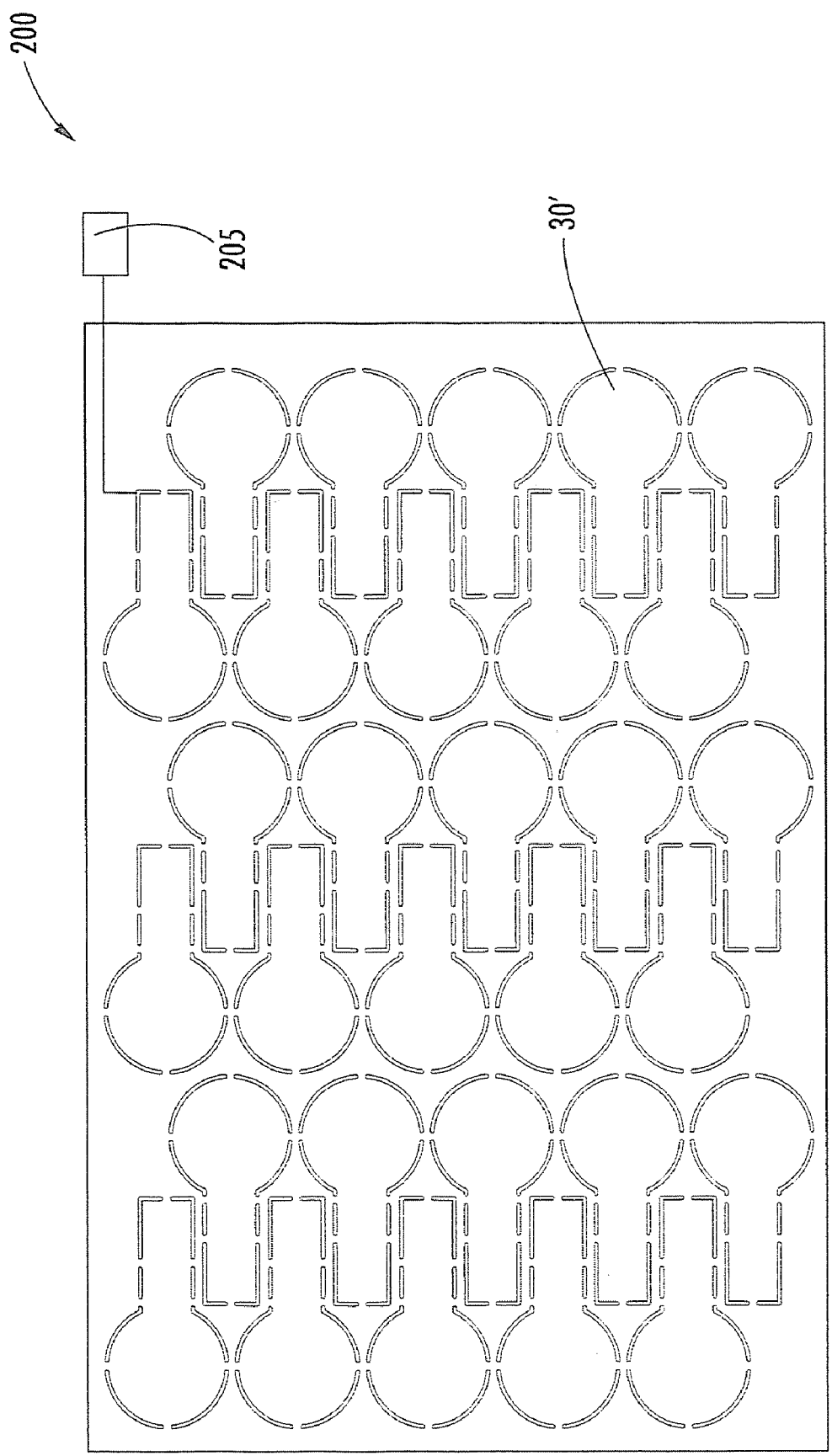
FIG. 10B is yet another schematic illustration of a sheet of sensors according to further embodiments of the present invention.

Sensor patches 30 according to embodiments of the present invention may be provided individually or in sheets containing multiple sensor patches 30. In particular, the sensor patches 30 may be fabricated in high-density sheets. As used herein, "high density" refers to multiple sensor patches provided on a unitary sheet. High density is intended to encompass very large sheets containing, for example, hundreds or thousands of sensors, as well as, for example, 3×3 regions of these very large sheets typically including 6 or more sensors per region. Providing the sensor patches 30 including memory devices 67, for example EEPROMs, on high density sheets 200 as illustrated in FIGS. 10A through 10D provide the capability of calibrating and/or pre-dosing the entire sheet of sensor patches 30 at one time. As shown in FIG. 10A, the sheets 200 may include perforations for subsequent separation of the individual sensor patches 30 from the high density sheet 200. In certain embodiments, the sheet of sensor patches 200 may include from about 30 to about 100 sensor patches 30 per sheet. In other embodiments, multiple patches 30 may be provided per square inch of the high-density sheet 200 and/or multiple patches 30, typically at least 6 patches, may be provided in a 3 by 3 inch region of the high-density sheet.

Figure 10C:
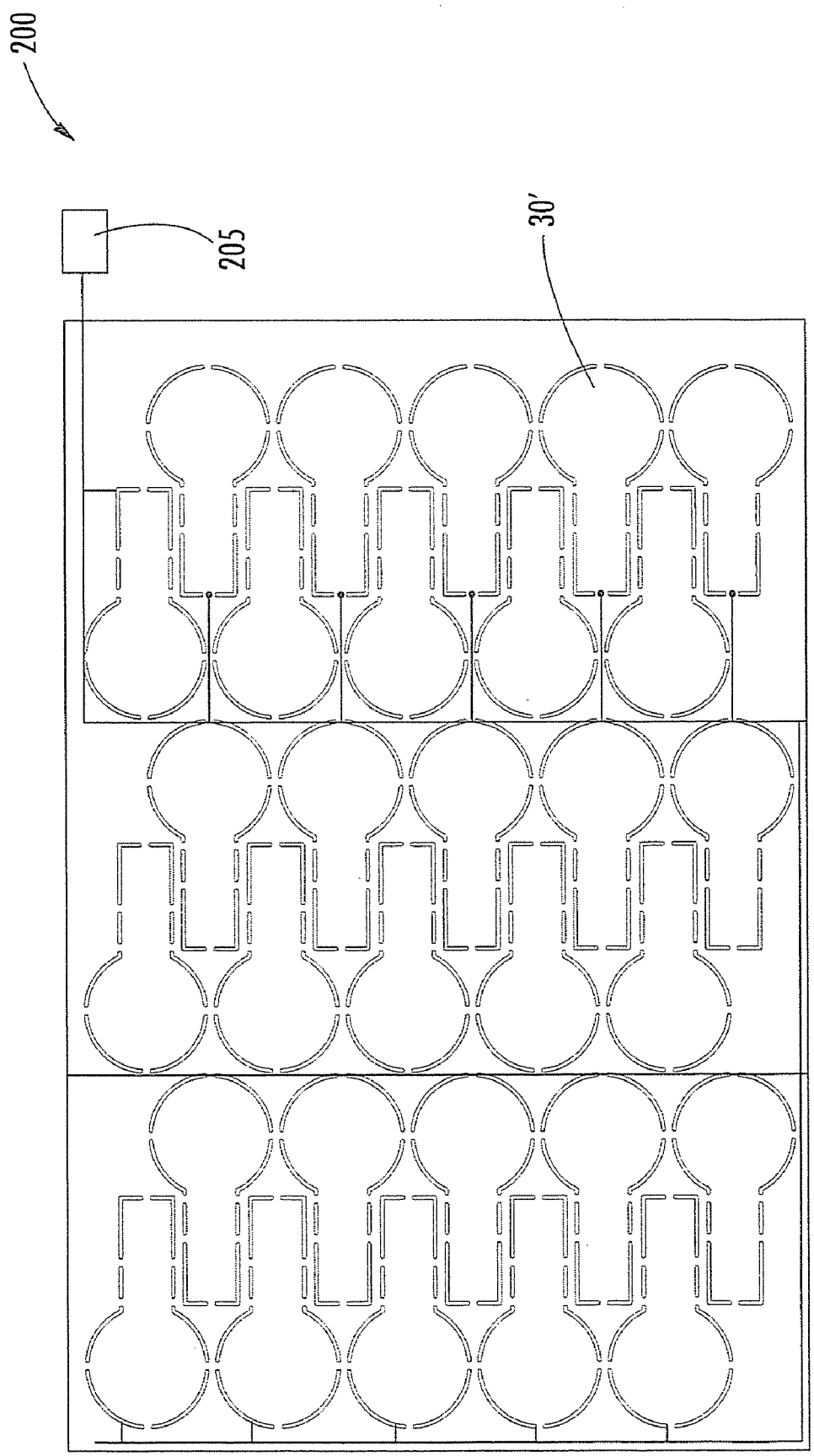
FIG. 10C is a further schematic illustration of a sheet of sensors according to still further embodiments of the present invention.
Figure 10D:
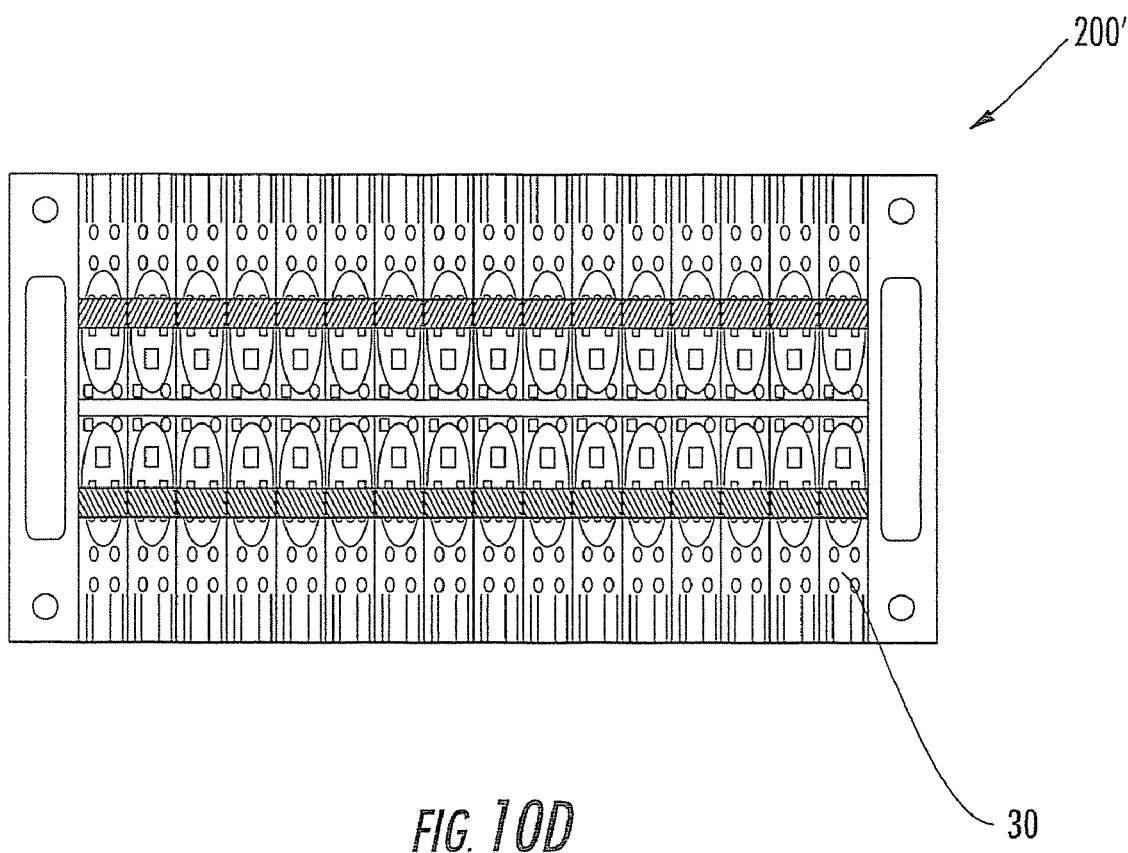
FIG. 10D is still a further schematic illustration of a sheet of sensor patches according to some embodiments of the present invention.

As further illustrated in FIG. 10D, in some embodiments of the present invention, the sensor patches 30 may be configured in an array 200' of 16×2 sensor patches. This arrangement may provide a method of processing 32 patches in a single batch. Each patch may be singularized, i.e., detached from the other sensor patches 30 in the batch, in the final processing steps. In some embodiments of the present invention, the dimensions of the array may be selected so that the sheet fits within a 6" diameter cylinder, such as a cylindrical blood irradiator chamber. The final assembly may be calibrated using a research irradiator, blood irradiator, LINAC or other radiotherapy equipment without departing from the teachings of the present invention. It will be understood that calibration techniques known to those having skill in the art may be used to calibrate the patches 30 according to some embodiments of the present invention.

The sensor patches 30 may be calibrated at the factory or OEM. Each of the sensor patches 30 or the entire sheet 200 of sensor patches 30 may be calibrated by providing a wire(s) 205 illustrated in FIG. 10B that electrically couples each of the sensor patches 30 on the sheet 200. For ease of reference, only a single electrical line to one sensor is shown on FIG. 10B. The calibration data may be provided to the sensor patches 30 through the wire(s) 205 and may be stored in the memory storage device 67 of the sensor patch 30. The ability to calibrate a plurality of sensor patches 30 simultaneously may provide more precision in the dosimetry process and, therefore, possibly more reliable results. It will be understood that the sensor patches 30 may each have a dedicated wire or the sheet can have a calibration line all connected to a common lead 206 as shown in FIG. 10C that may be used to calibrate and/or pre-dose the sensor patches 30 individually.

As discussed above, the sensor patches 30 may be pre-dosed, i.e. dosed prior to placement on the patient. Dosing a sensor patch may include, for example, setting the amount of radiation to be delivered to a patient and the particular region(s) on the patient to which the radiation should be delivered. This process is typically performed by a physicist and can be very time consuming. The possibility of accurately pre-dosing a sensor patch 30 may significantly reduce the need for a physicist to be involved in the dosimetry confirmation process. In other words, using reliable dose patches can reduce the time a physicist expends to confirm the treatment beam and path dose.

It will be understood that sensor patches 30 adapted to be received by a reader 75 are not limited to the configuration illustrated in the figures provided herein. These figures are provided for exemplary purposes only and are not meant to limit the present invention. For example, the sensor patch 30' of FIG. 9B can be configured with a geometry that allows it (entirely or partially) to be received by a reader 75". The insertable geometry may take the form of an elongated tab, one end of the tab containing the radiation sensitive circuitry as well as the memory and the other end of the tab containing the electrical contacts for insertion into the reader device (not shown).

Figure 22:
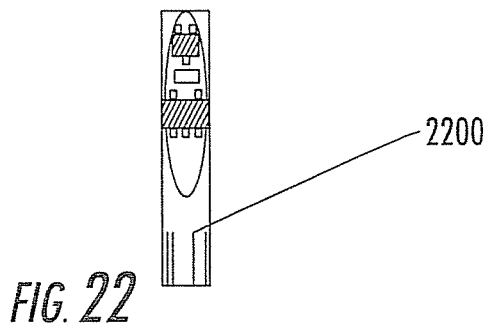
FIG. 22 is a schematic diagram of a test strip according to further embodiments of the present invention.

Some embodiments of the present invention provide a test strip 2200 as illustrated in FIG. 22. The test strip 2200 may allow the functionality and calibration of the reader 75 to be tested and verified. According to some embodiments of the present invention, the test strip 200 may consist of a sensor patch including an EEPROM and a resistor and a voltage reference instead of the MOSFET/RADFET. Thus, in the event that the reader 75 is, for example, left in the radiation treatment beam, has a mechanical failure or the like, a 4.096 V reference or a current source may be altered and, therefore, may yield incorrect dose readings. The test strip 2200 may provide an external reference that may be used to verify proper operation and calibration of the reader 75.

As stated above, the test strip 2200 may be similar to the sensor patch 30 except the RADFET may be replaced with a series combination of a voltage reference and a resistance, for example, a 1.2V shunt reference (specified at 0.1% tolerance such as an LM4051-1.2) and a 10KΩ resistor (0.1% tolerance). In some embodiments of the present invention, the gate/drain connection may have a 39KΩ, 0.1% tolerance resistor coupled to ground on the test strip 2200. The 39KΩ resistor may provide an additional 52 μA bias to the series 1.2V reference and 10 KΩ resistor.

The test strip 2200 may include a memory map, which may include, among other things, the defaults from the base load (at the ZTC process), i.e. the pre-radiation data. Table 7 of FIG. 31 contains a listing of functional specifications of test strips according to some embodiments of the present invention. It will be understood that the functional specifications listed in FIG. 31 are provided for exemplary purposes only and that embodiments of the present invention are not limited to this configuration.

The reader 75 may interrogate the test strip memory and request that a doctor technician perform a "zeroing operation" discussed further below. The test strip 2200 may be zeroed and the resulting digital to analog conversion (DACB) value may be compared to the DACB value determined at the factory. The result may indicate, for example, "Reader OK" if the DACB value is within a set of limits provided or "Reader needs Cal" if the DACB value is outside the set of limits. It will be understood that the limits may be determined on a per-reader basis during factory calibration.

Figure 11:
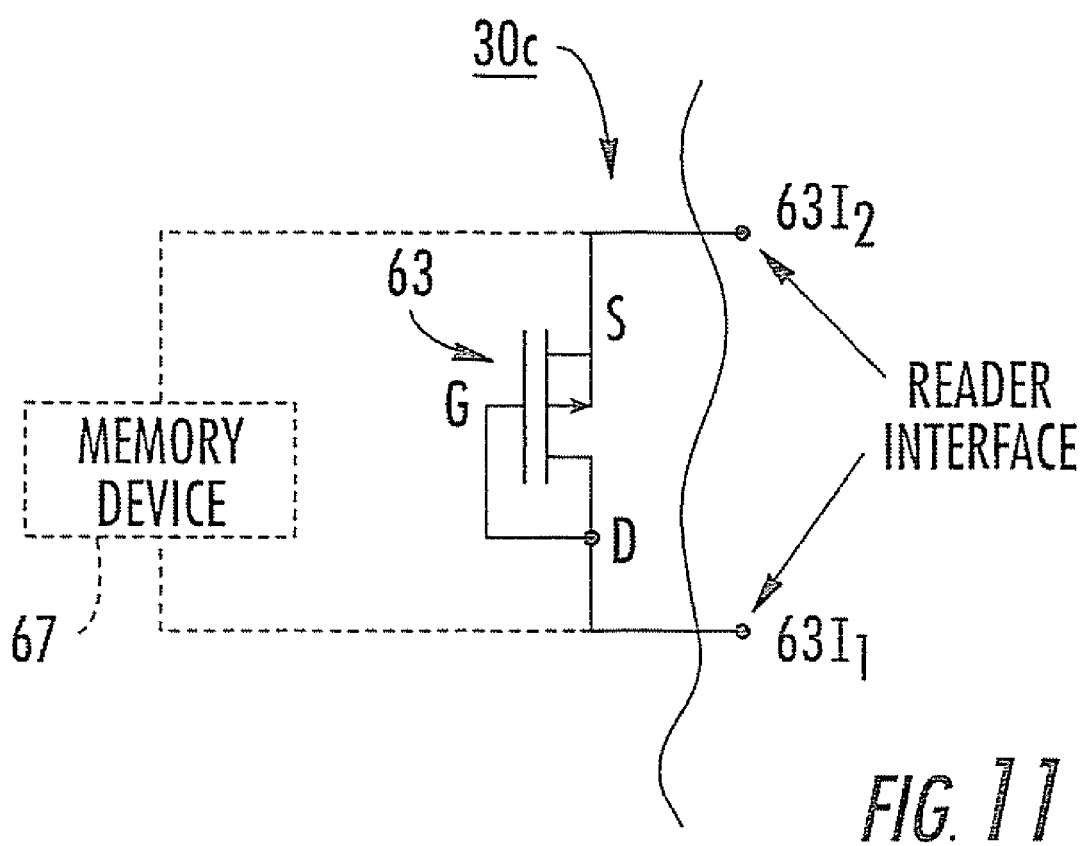
FIG. 11 is a schematic of a circuit diagram of a MOSFET sensor with a reader interface and an optional memory according to some embodiments of the present invention.
Figure 12A:
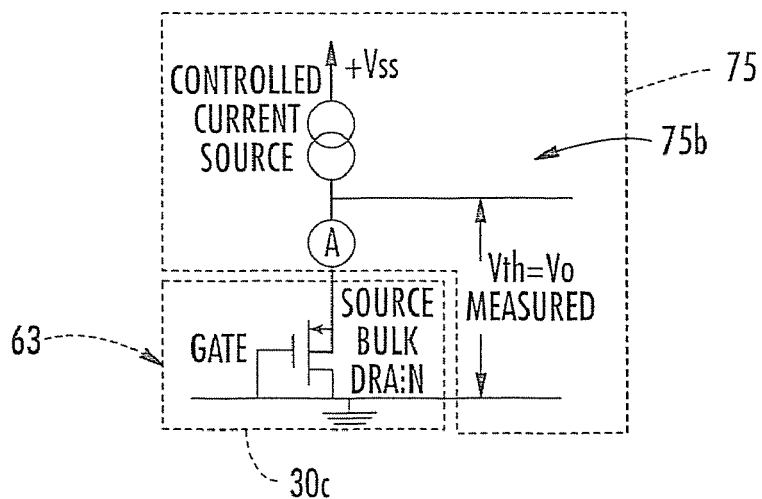
FIG. 12A is a schematic of a threshold voltage reader circuit according to further embodiments of the present invention.

In certain embodiments of the present invention, the test strip 2200 may be configured to prevent modification by the reader 75. In some embodiments of the present invention, the reader may be configured to indicate "Reader OK" when the test strip 2200 is inserted and a predetermined reference voltage, such as about 4.096 V, is within a predetermined range. The reader may be further configured to indicate "Reader needs Cal" if the reference voltage is outside of the predetermined range. In some embodiments of the present invention, the predetermined range may be from about 4.075 to about 4.116V. The tolerance on the limits may be about +/−0.005V As shown in FIG. 11, in certain embodiments, the patch radiation sensitive device 63 is a RADFET. The RADFET can be biased with a gate/drain short so that it acts as a two-terminal device. FIG. 11 illustrates a portion of the circuit 30c with a RADFET 63 and two associated reader 75 interface or contact points 63I$_1$, 63I$_2$. FIG. 12A illustrates a reader 75 (upper broken line box) and the circuit 30c (lower broken line box) with the RADFET 63 configured with a gate to drain short. As shown, the reader 75 can include a RADFET bias circuit 75b that includes a controlled current source to allow a voltage reading to be obtained corresponding to the threshold voltage of the RADFET.

Figure 12B:
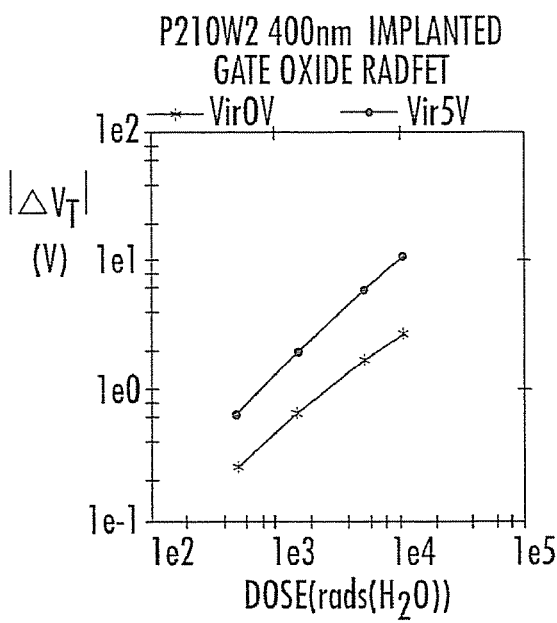
FIG. 12B is a graph of the change in the threshold voltage value versus radiation dose according to still further embodiments of the present invention.

As shown by the graph in FIG. 12B, changes in surface state charge density induced by ionizing radiation causes a shift in threshold voltage in the RADFET. FIG. 12B illustrates a radiation response of a standard P210W2 400 nm implanted gate oxide RADFET with lines for 0V (the -0- marked line) and 5V (the line with the -*- markings) irradiation bias responses. To obtain the amount of threshold voltage ("Vth") shift, the Vth value (zero dose) can be subtracted from the post-irradiation value and the calibration curve used to determine radiation dose. The calibration curve can be pre-loaded into the controller of the reader or a computer to provide the dose data. In certain embodiments, when obtaining the readings, the clinician may wear grounding straps to reduce static sensitivity of the circuitry. In certain embodiments, such as where contact points are exposed, ESD protection may be integrated into the sensor patch 30 itself.

As shown in FIG. 12A, the Vth change can be measured by determining the change in applied gate voltage necessary to induce a set current flow. As noted above, the RADFET characterization data can be obtained prior to exposure to radiation (zero dose). Thus, the starting threshold voltage of the sensor patch 30 will be known from a priori information (or can be obtained by the clinician prior to placing on the patient or after on the patient but before radiation exposure) and can be placed in the reader 75 or computer associated or in communication therewith.

Figure 13:
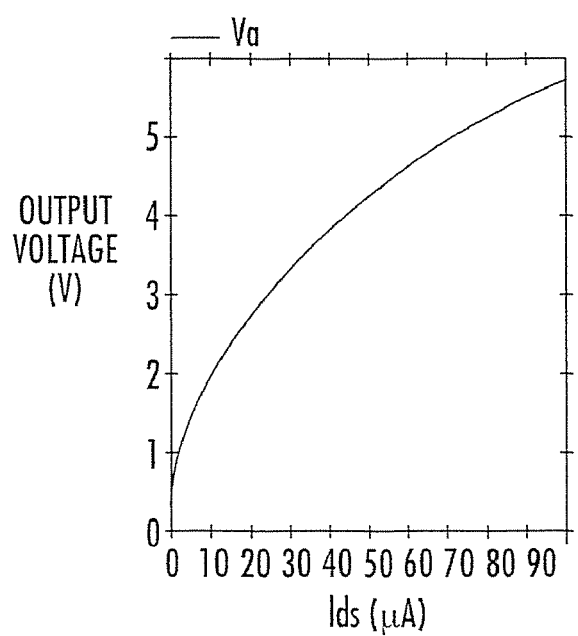
FIG. 13 is a graph of the threshold voltage dependence on Ids using the voltage ($V_0$) of the reader illustrated in FIG. 12A.

FIG. 13 illustrates the threshold voltage relationship between output voltage (voltage) and current Ids (the electrical current, drain-to source, in microamps) as measured using the output voltage of the reader circuit shown in FIG. 12A. In operation, the reader circuit is configured to contact the sensor to provide a constant current source to the circuit so as to be able measure Vth at a substantially constant or fixed bias condition.

In some embodiments of the present invention, the zero temperature coefficient of the MOSFET/RADFET 63 (FIG. 11) may be obtained. The zero temperature coefficient of a MOSFET refers to a specific bias current level at which the threshold voltage of the MOSFET does not change significantly with temperature variation in the range of temperatures likely to be encountered according to some embodiments of the present invention. Although the zero temperature bias current typically varies from one MOSFET to another, it is a parameter that may be measured before the administration of radiation therapy to the patient and stored, for example, in the memory device 67, along with the pre-radiation threshold voltage of the MOSFET measured when the MOSFET is biased with the zero temperature bias current. After recording and storing these parameters, the patch 30 may be exposed to radiation and inserted into the reader 75 or wirelessly coupled to the reader 75. The MOSFET may be biased with the stored zero temperature bias current (which the reader 75 may obtains from the memory device 67) and the post-radiation threshold voltage of the MOSFET may be measured. The change in the threshold voltage, i.e., the difference between the pre-radiation threshold voltage and the post-radiation threshold voltage, may be used by the reader 75 to calculate the radiation dose. It will be understood that in these embodiments of the present invention the MOSFET is not operated in a biased configuration or otherwise powered during the radiation treatment session.

The memory device 67 on the patch 30 may include a memory map identifying memory locations and contents thereof. In some embodiments of the present invention, the memory map may resemble a spreadsheet. The memory map may include one or more fields containing data, such as serial numbers, calibration factors, dose records, time stamps, biasing parameters, factory calibration information and the like. The reader 75 may access data stored in the memory map using, for example, a standard I2C protocol as discussed further below. Details with respect to memory maps will be understood by those having skill in the art and will not be discussed further herein.

In some embodiments of the present invention, the dose may be calculated using Equation 1 set out below:

$$\text{Dose} = k_{energy} * k_{rate} * k_{SSD} * k_{fieldsize} * k_{temp} * k_{wedge} * k_{fade} * [a(v_{shift})^3 + b(v_{shift})^2 + c(v_{shift}) + d]$$ (Equation 1)

Figure 23:
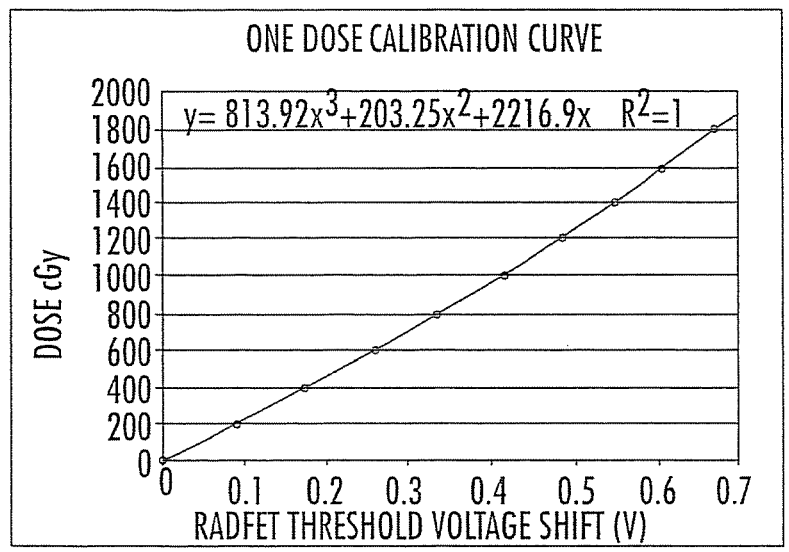
FIG. 23 is a calibration curve illustrating a dose response of an exemplary MOSFET/RADFET according to still further embodiments of the present invention.

$V_{shift}$ is the voltage difference (as seen by the 24-bit A/D converter) between the pre-radiation and post-radiation threshold voltage when measured at the zero temperature coefficient current ($I_{BiasZTC}$) discussed below. $k_{energy}$ (Energy), $k_{rate}$ (Dose Rate), $k_{SSD}$, $k_{fieldsize}$ (Field Size), $k_{temp}$ (Temperature), $k_{wedge}$ (Wedge Angle), $k_{fade}$ (Fade Time) (See FIG. 25) and/or other correction factors (collectively the "k-factors") may be stored in memory locations of the memory map stored in the electronic memory 67. In some embodiments of the present invention, if a coefficient is required, the reader can prompt the user for the coefficient during the zeroing operation. A calibration curve illustrating a dose response of an exemplary MOSFET/RADFET according to some embodiments of the present invention is provided in FIG. 23. It will be understood that the calibration curve provided in FIG. 23 is provided for exemplary purposes only and that embodiments of the present invention are not limited by this example.

Figures 24, 25, 26:
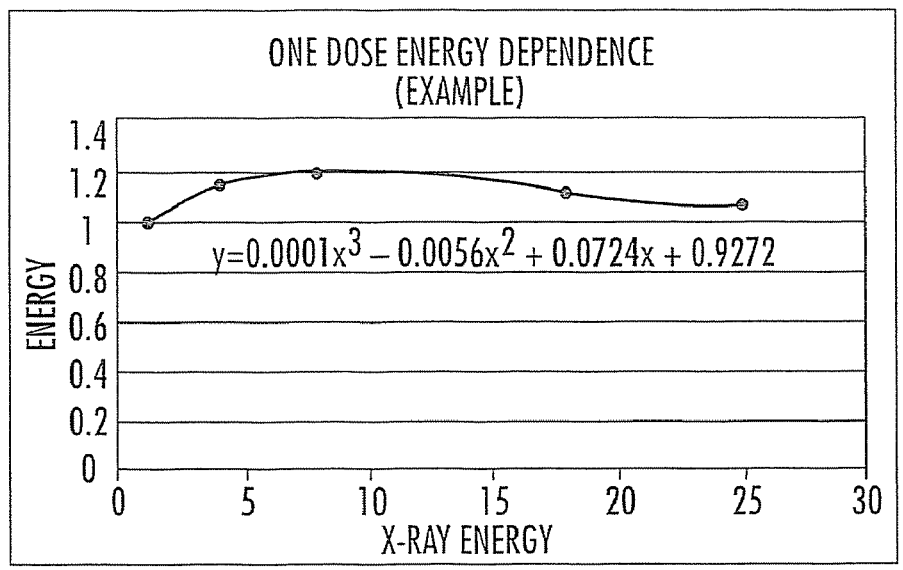
FIG. 24 is a graph illustrating an exemplary correction factor for energy dependence according to some embodiments of the present invention.
FIG. 25 is a table illustrating exemplary "k-factors" that may be applied to a dose equation according to further embodiments of the present invention.
FIG. 26 is a table illustrating an order of storing temperature correction coefficients according to still further embodiments of the present invention.

As necessary, correction factors may be applied for energy, dose rate, field size, temperature, wedge factors, fading or other user-defined corrections. The reader 75 can be configured to provide automatic prompts to a user or an equipment operational station to obtain the desired patient-specific and/or equipment inputs (i.e., user input calibration factors). Coefficients for the correction factors may be stored in the electronic memory 67 of the patch 30. User correction factors may also be stored in the reader 75 non-volatile memory and may be copied into the electronic memory 67 of the patch 30 as a record if the correction factors are used in the dose calculation. A graph set out in FIG. 24 illustrates and an exemplary correction factor for energy dependence. It will be understood that the graph provided in FIG. 24 is provided for exemplary purposes only and that embodiments of the present invention are not limited by this example.

Referring to FIG. 24, the correction factors are curve-fitted to a 3rd-order polynomial and the coefficients may be stored in the memory cell locations of the memory map in the electronic memory 67 of the patch 30. In some embodiments of the present invention, the default values may be 0, 0, 0, 1 for a, b, c, and d, respectively. Table 2 of FIG. 25 sets out exemplary "k-factors", discussed above, that may be applied to the dose equation set out in Equation 1 above.

In particular, temperature correction factor coefficients may be stored in the memory locations of the memory map stored in the electronic memory 67 of the patch 30. In some embodiments of the present invention, the temperature correction factor coefficients may be stored in a floating point format. The coefficients may be stored in the order illustrated in Table 3 of FIG. 26 illustrating temperature correction coefficient locations.

The standard temperature may be normalized to about 20° C. The correction factors may be curve-fitted to a 3rd-order polynomial and the coefficients may be stored in the memory map of the patch 30. The default values may be, for example, set to 0, 0, 0, 1 for a, b, c, and d, respectively. The input to the equation may be the temperature in ° C. determined by calculating the temperature (° C.). This is calculated from the difference in a diode reference voltage and a diode voltage measured during the post-radiation process. The difference may be multiplied by the diode temperature coefficient stored in the memory 67 and added to 27° C. plus 1/10th of $T_{Offset}$ discussed below.

For example, the patch temperature may be determined according to Equations 2 and 3 set out below:

$$V_{Diode}=2.048-(V_{ADC\_Diode}-800000 \text{ h})*4.096/224 \quad \text{(Equation 2)}$$

$$\text{Temperature}=27+10*(T_{Offset})+(V_{Diode}\text{-Diode Voltage Reference})/\text{Temp Coeff. of the Diode} \quad \text{(Equation 3)}$$

Figures 27, 28, 29:
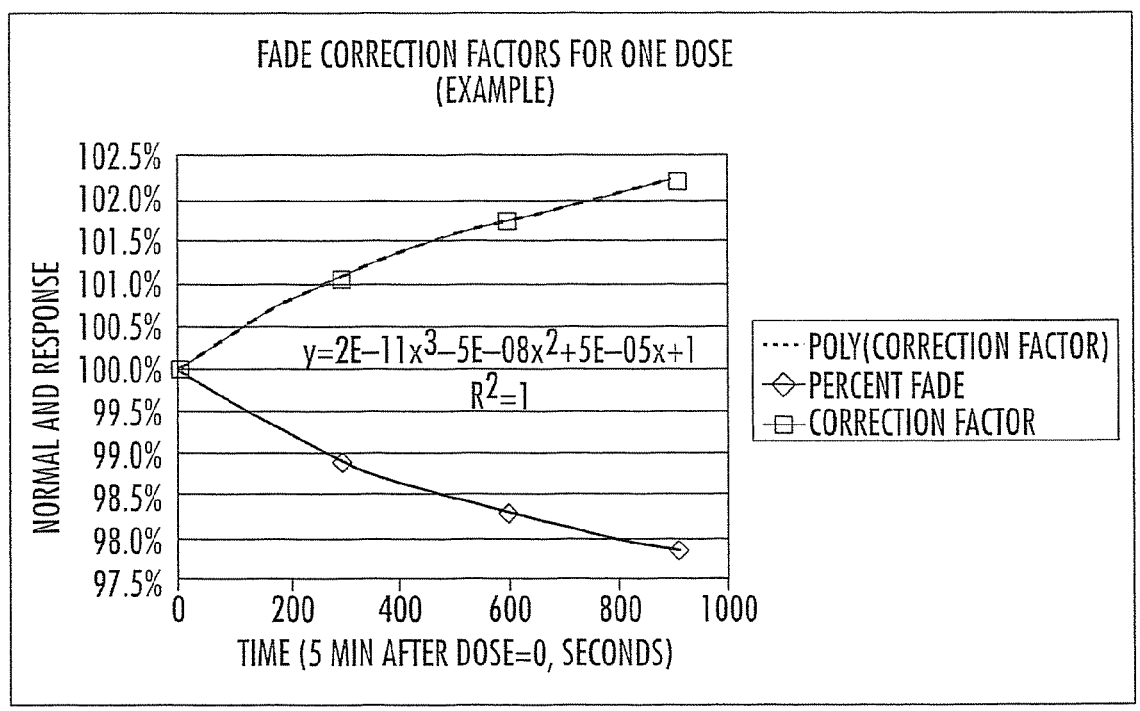
FIG. 27 is a table illustrating an order of storing fade correction coefficient according to some embodiments of the present invention.
FIG. 28 is a graph illustrating an exemplary response for fade in the RADFET voltage following a dose application according to further embodiments of the present invention.
FIG. 29 is a table including V/I relationships of readers according to still further embodiments of the present invention.

Furthermore, fade correction factor coefficients, i.e., coefficients of the correction factors for fading of the RADFET voltage, may be stored in the memory locations of the memory map stored in the electronic memory 67 of the patch 30. In some embodiments of the present invention, the fade correction factor coefficients may be stored in a floating point format. The coefficients may be stored in the order illustrated in Table 4 of FIG. 27 illustrating fade correction coefficient locations.

The standard time may be normalized to about 300 seconds (5 minutes). The correction factors may be curve-fitted to a 3rd-order polynomial and the coefficients may be stored in the respective locations in the patch memory 67. The default values may be set to 0, 0, 0, 1 for a, b, c, and d, respectively. The input to the dose equation (Equation 1) is the difference in time (seconds) between the Dose-End timestamp and the Reading Time versus the 300 second normalized time. For example, if the reading takes place 5 minutes and 30 seconds after the dose end time, the input to the dose equation (Equation 1) would be 30 seconds. If the reading takes place 4 minutes after the dose end time, then the input to the equation would be −60 seconds.

In some embodiments of the present invention, the user may be prompted to input, such as via a touch sensor or a keypad, to indicate the end of the dose treatment. If there are multiple fields of radiation involved, the user may be instructed to press the timestamp button during the last treatment field. The time difference may be calculated (in seconds) between the dose end time and the reading time and may be used to correct for fade. If the prompt for dose time is not configured (in the reader) then the Zero-reading time plus 300 seconds may be used as the dose end time. A graph set out in FIG. 28 illustrates an exemplary response for fade in the RADFET voltage following a dose application.

The cells of the memory map may further include a standardized hex-coded D/A Converter value that may be used to bias the RADFET 63 to the factory-determined zero temperature bias current (ZTC). The value of the ZTC current may be determined at the factory and may be stored in the memory device 67 during the calibration process for each individual sensor. The value that may be stored in the memory device 67 is the D/A value and would be written if the particular reader reference voltages, D/A (assume 16-bit), resistor values, offset voltages and bias currents are ideal. For example, if the factory determined ZTC current is:

$$i_{Bias\_ZTC}=10.00 \text{ }\mu A \quad \text{(Equation 4)}$$

The value of the ZTC current stored in the memory device 67 ($I_{BiasZTC}$) during the calibration process for each individual sensor may be calculated using Equation 5 set out below.

$$I_{BiasZTC}=((V_{4.096}-i_{Bias\_ZTC}*R_{Bias})/V_{4.096})*2^{16} \quad \text{(Equation 5)}$$

In some embodiments of the present invention, the parameters used in this calculation may be: $V_{4.096}$=4.096 V, $V_{2.048}$=2.048 V and $R_{Bias}$=10.00 KΩ. Inserting these values into Equation 5, $I_{BiasZTC}$ may be 79 $C0_H$.

The actual DAC value that may be used for a particular reader 75 depends on the reader calibration coefficients. The actual DAC value may be adjusted so that the effects of the non-ideal, such as 4.096 and 2.048 VDC references, 10.00KΩ resistor, op-amp input offset voltage and/or bias current of each particular reader 75 may be corrected. In some embodiments of the present invention, the reader calibration coefficients for the $I_{BiasZTC}$ current are "$I_{Bias\_Offset}$" and "$I_{Bias\_Gain}$" as may be stored in a memory location of the reader 75 and may be determined during factory calibration. The actual value written to a particular reader DAC may be calculated using Equation 6 set out below:

$$Ibias\text{-}ztc_{reader(x)}=I_{BiasZTC}*I_{Bias\_Gain}+I_{Bias\_Offset} \quad \text{(Equation 6)}$$

Table 5 of FIG. 29 includes exemplary V/I relationships of readers determined during calibration according to some embodiments of the present invention. It will be understood that the V/I relationships set out in Table 5 are provided for exemplary purposes only and embodiments of the present invention are not limited to this configuration.

In some embodiments of the present invention, the bias current accuracy for any individual reader 75 may be specified at about +/−100 nA. The trans-conductance of the RADFET may be specified at about 1/100KΩ max at the ZTC bias current. If the bias current changes between the "pre-radiation" and "post-radiation" dose readings due to, for example, switching readers, there may be a potential voltage error of about 100 nA*100KΩ=10 mV. Since the initial sensitivity of the RADFET may be specified at about 0.25 mV/cGy, this represents a potential 40 cGy error. The specified error for the system may be about +/−1 cGy for a 20 cGy dose. The repeatability of the bias current (between "pre" and "post" dose measurements) on an individual reader 75 may be specified at about +/−1 nA so that the error due to a "trans-conductance effect" may be limited to about 1 nA*100KΩ=100 µV.

The reader 75 may initially "zero" an un-dosed sensor patch 30 by adjusting the output of a digital to analog converter (DAC) so that the analog to digital (A/D) converter input is near zero. The DAC is the standardized bias current setting that may be used for the A/D readings for the pre-radiation and post-radiation threshold voltage measurements. The "zeroed" value may be stored in the electronic memory 67 and the patch status register may be updated to indicate that the patch has been "zeroed". The zeroing operation may limit the range of the RADFET bias current source. After the patch has been dosed and reinserted, the reader 75 may reset the DAC-B channel to a previous level using data stored in the memory location of the electronic memory 67 so that the voltage measured by the A/D converter may represent the shift in voltage due to radiation. The scaling may be arranged in hardware so that the voltage generated by the DAC-B is approximately ⅓ of the threshold voltage at the RADFET. The A/D conversion result and the standardized bias current (DAC or DAC-A) may be stored in cells of the electronic memory 67.

The Digital-to-Analog Converter (DAC) may provide two functions. The first is to establish the bias current in the RADFET based on a factory-derived bias current setting. This current may be established so that there is a minimum influence of temperature on the RADFET threshold voltage. The second DAC, OFFSET DAC, may provide a means to offset the RADFET initial threshold voltage in the "zeroing" procedure. In other words, prior to dosing, the patch may be zeroed by adjusting the OFFSET DAC so that the output of the summing amplifier is about 2.048V+/−100 mV when the patch RADFET is connected. The summing amplifier subtracts the voltage from the OFFSET DAC from the RADFET and applies the difference to the A/D Converter. This DAC setting may be stored in electronic memory 67 of the patch 30 and reused after dose is applied to bias the RADFET. The difference in the pre-dose and post-dose RADFET threshold voltages measured by the A/D Converter may be used to calculate the measured dose.

The memory map may also include a memory cell including $T_{offset}$, which may be, for example, a byte representing the temperature at which the diode voltage of the RADFET may be measured. In some embodiments of the present invention, the offset may be based on a nominal temperature of about 27.0° C. Accordingly, if, for example, the actual temperature during the RADFET diode measurement (during the ZTC process) is 27.0° C., then the offset will be 00 h.

In some embodiments of the present invention, the diode voltage may be measured (at the $I_{Bias\_Diode}$ current) during ZTC processing and the voltage may be converted to hexadecimal notation using Equation 7 set out below.

$$V_{Diode@Temp} = 800000\ h + (2.048 - V_{Diode(measured)}) * 2^{24} / 4.096 \quad \text{(Equation 7)}$$

This value may be stored in memory locations of the memory map in the electronic memory 67.

As noted above, the MOSFET bias parameters, along with customized calibration coefficients, are stored in the EEPROM memory provided on each patch. The patch memory also includes a patch identifier or serial number, and instructions on how the reader interfaces with the patch. Provision of these instructions allows the reader to work with multiple generations of patches without necessitating upgrades to the reader. The patch memory also stores the detected and calculated radiation dosages, the date and time of the treatment, and a clinician-entered patient identifier and/or record number. After use, the patch can be placed in the patient file or medical record to form a part of the archived patient treatment history, or may be discarded.

FIGS. 14A and 14B illustrate alternate embodiments of MOSFET based circuits 30c. Each circuit 30c employs a RADFET pair 63p (FIG. 14A), 63p' (FIG. 14B) as the radiation sensitive device 63. The configuration on the left of each of these figures illustrates the irradiation configuration and the configuration on the right illustrates the read dose configuration. In the embodiment shown in FIG. 14A, the RADFET pair 63p are differentially biased during irradiation to create different voltage offsets. Each of the RADFETs in the pair 63p₁, 63p₂ can be differentially biased during radiation to generate different voltage offsets when exposed to radiation. Using a pair of RADFETS can reduce the influence of temperature in the detected voltage shift value. In particular embodiments, the RADFET pair can be matched (such as taken from the same part of the substrate during fabrication) to reduce drift effects (Vth drift). In certain embodiments, the voltage reading can be obtained with a zero bias state, and/or without requiring wires during radiation, and/or without requiring a floating gate structure.

In the embodiment shown in FIG. 14B, one of the RADFETs 63p₁' in the pair 63p is selectively implanted with dopant ions to shift the threshold voltage (Vth) of that RADFET with respect to the other RADFET 63p₂'. The ion implantation can be carried out in various manners as known to those of skill in the art, such as by masking one of the FETs with photoresist to inhibit ions from entering into the gate region. As is well known, using the proper implant species and/or dopant material can increase the FET sensitivity to radiation effects. In certain embodiments of the present invention, a MOSFET (RADFET) pair is used to effectively provide "differential biasing" without the need to apply an external voltage and without the need for a floating gate structure. That is, the MOSFETs can be configured to be individually unbiased and readings of the two MOSFETs (one at a different threshold voltage value) generates the differential biasing. In particular embodiments, this radiation sensitive MOSFET pair configuration that does not require floating gate structures and/or external voltage can be used in implantable as well as skin mounted sensors, such as in implantable sensors used as described in U.S. Pat. No. 6,402,689 to Scarantino et al.

Figure 15C:
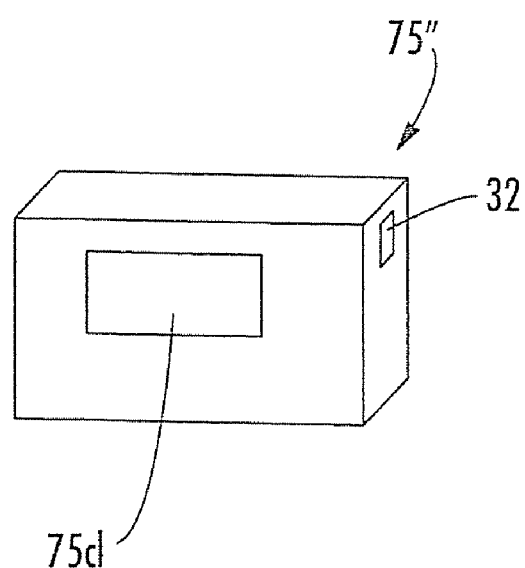
FIG. 15C is a block diagram illustrating a reader device according to further embodiments of the present invention.

FIG. 15A illustrates embodiments of a radiation dose evaluation system 15 according to embodiments of the present invention. As shown, the system 15 includes a reader 75 and a set of radiation sensor patches 130'. The reader 75 may include, for example, the reader 75' of FIG. 15B or the reader 75" of FIG. 15C. The sensor patches 30 can be arranged as a strip of patches 30 held in a single-patient sized package 130p. As before, the package 130p may also include bar coded radiation calibration characterizing data labels 132 for the sensor patches 30 and/or a memory 167 in each or selected memory patches 30. The reader 75' as shown in FIG. 15B can include the probe 75p, an optical wand 75w and a display screen 75d. The reader 75" as shown in FIG. 15C can include a sensor port 32 and a display screen 75d. The reader 75 can also include a RADFET bias circuit 75b. In certain embodiments, the reader 75 is a portable flat pocket or palm size reader that a clinician can carry relatively non-obtrusively in his/her pocket or a similar sized casing.

As shown by the dotted line boxes in FIG. 15A, the reader 75 may hold a power source 78 and plurality of operational software modules including: an optical bar code reader module 76, a zero-dose threshold voltage data module 77, a radiation dose conversion module (based on a predetermined voltage threshold to radiation dose response curve) 79, and a threshold voltage post radiation data module 80.

In operation, the reader 75 can be configured to supply a bias current to the RADFET by attaching to the sensor patch 30 and electrically contacting the conductive probe region 30p or the electrical contacts 31. The reader 75 can measure the voltage shift response of the RADFET on the sensor patch 30 and calculate radiation dose based on the shift and the dose conversion algorithm. The reader 75 can display the results to the clinician (such as on an integrated LCD screen 75d incorporated into the body of the reader) and may be configured to download or upload the data to another device (such as a computer or computer network) for electronic record generation or storage.

The reader may include an electronic memory map identifying memory locations and contents thereof. In some embodiments of the present invention, the memory map may resemble a spreadsheet. The memory map may include one or more fields containing data, such as serial numbers, revision number, reader calibration data, A/D gain correction, A/D offset correction, D/A gain correction, D/A offset correction, hospital ID and the like. In some embodiments of the present invention, the reader memory may be large enough to store 250 dose records of about 64 bytes each. The dose record may include items listed in Table 6 of FIG. 30. It will be understood that the dose record of FIG. 30 is provided for exemplary purposes only and embodiments of the present invention should not be limited to this configuration. Details with respect to memory maps will be understood by those having skill in the art and will not be discussed further herein.

The dose amount can be calculated for each sensor patch 30 used. In particular embodiments, the system can be configured to generate an average or weighted average of the dose amount determined over a plurality of the patches. In certain embodiments, where there is a large variation in values (or if it departs from a statistical norm or predicted value) the system can be configured to discard that sensor value or to alert the clinician of potential data corruption. Of course, much smaller values are predicted in sensitive areas away from the targeted zone and the system can be configured to evaluate whether the sensor is in a primary location or in a secondary zone as regards the radiation path.

It is noted that features described with respect to one embodiment of the sensor, reader and/or system may be incorporated into other embodiments and the description and illustrations of such features are not be construed as limited to the particular embodiment for which it was described.

As will be appreciated by one of skill in the art, the present invention may be embodied as a method, data or signal processing system, or computer program product. Accordingly, the present invention may take the form of an entirely hardware embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as LABVIEW, Java®, Smalltalk, Python, or C++. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Figure 16:
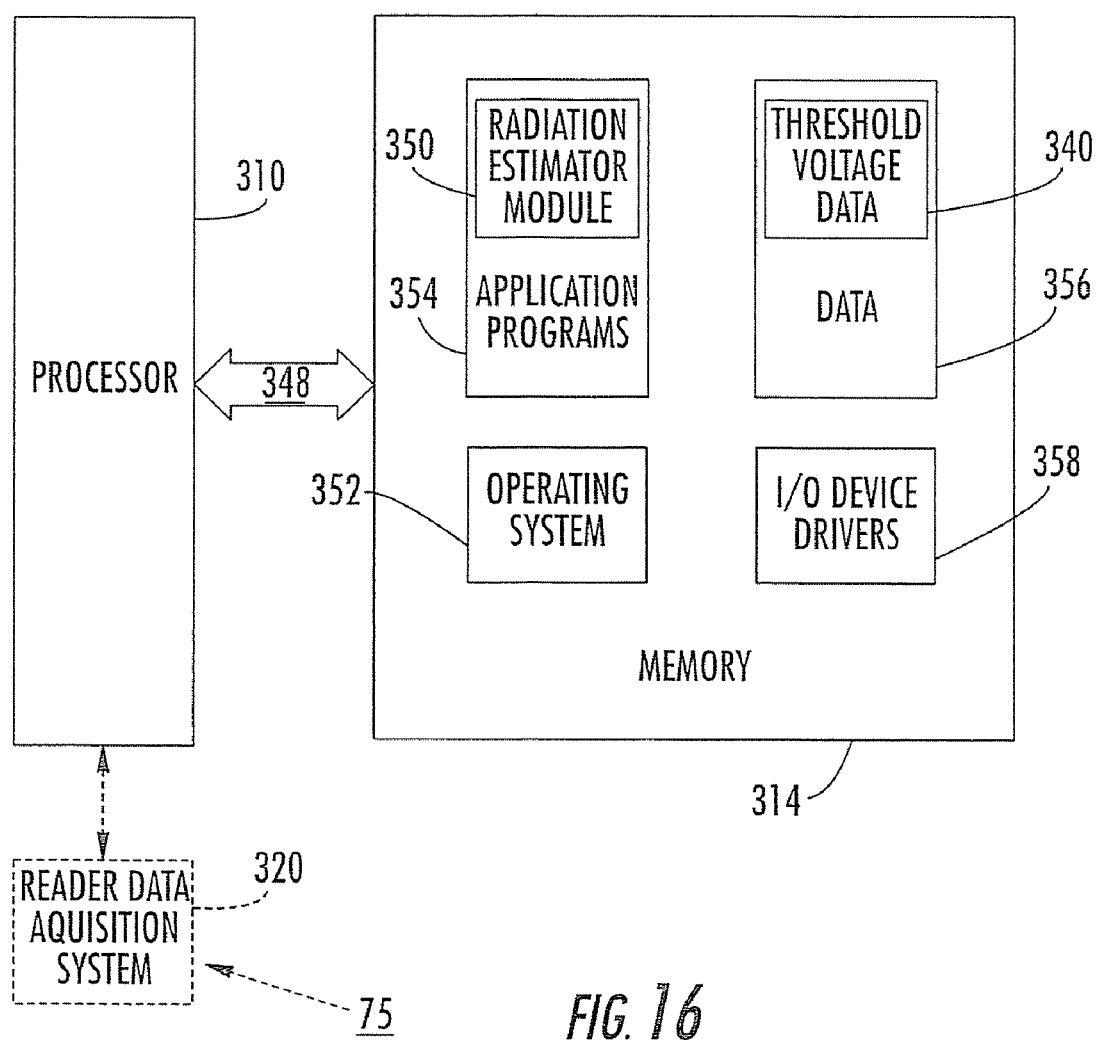
FIG. 16 is a block diagram of a computer program having a radiation estimation module according to still further embodiments of the present invention.

FIG. 16 is a block diagram of exemplary embodiments of data processing systems that illustrate systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system. The memory 314 can include, but is not limited to, the following types of devices: cache, ROM, PROM, EPROM, EEPROM, flash memory, SRAM, and DRAM.

As shown in FIG. 16, the memory 314 may include several categories of software and data used in the data processing system 305: the operating system 352; the application programs 354; the input/output (I/O) device drivers 358; a radiation estimator module 350; and the data 356. The data 356 may include threshold voltage data 340 (zero dose and post irradiation dose levels) which may be obtained from a reader data acquisition system 320. As will be appreciated by those of skill in the art, the operating system 352 may be any operating system suitable for use with a data processing system, such as OS/2, AIX, OS/390 or System390 from International Business Machines Corporation, Armonk, N.Y., Windows CE, Windows NT, Windows95, Windows98, Windows2000 or Windows XP from Microsoft Corporation, Redmond, Wash., Unix or Linux or FreeBSD, Palm OS from Palm, Inc., Mac OS from Apple Computer, or proprietary operating systems. The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and preferably include at least one application that supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the radiation estimator module 350 being an application program in FIG. 16, as will be appreciated by those of skill in the art, other configurations may also be utilized while still benefiting from the teachings of the present invention.

For example, the radiation estimation module 350 may also be incorporated into the operating system 352, the I/O device drivers 358 or other such logical division of the data processing system. Thus, the present invention should not be construed as limited to the configuration of FIG. 16, which is intended to encompass any configuration capable of carrying out the operations described herein.

In certain embodiments, the radiation estimation module 350 includes computer program code for estimating radiation dose based on the measured threshold voltage shift. The I/O data port can be used to transfer information between the data processing system and the reader data acquisition system 320 or another computer system or a network (e.g., the Internet) or to other devices controlled by the processor. These components may be conventional components such as those used in many conventional data processing systems that may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configurations illustrated in the figures but is intended to encompass any configuration capable of carrying out the operations described herein.

The flowcharts and block diagrams of certain of the figures herein illustrate the architecture, functionality, and operation of possible implementations of radiation detection means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Figure 17:
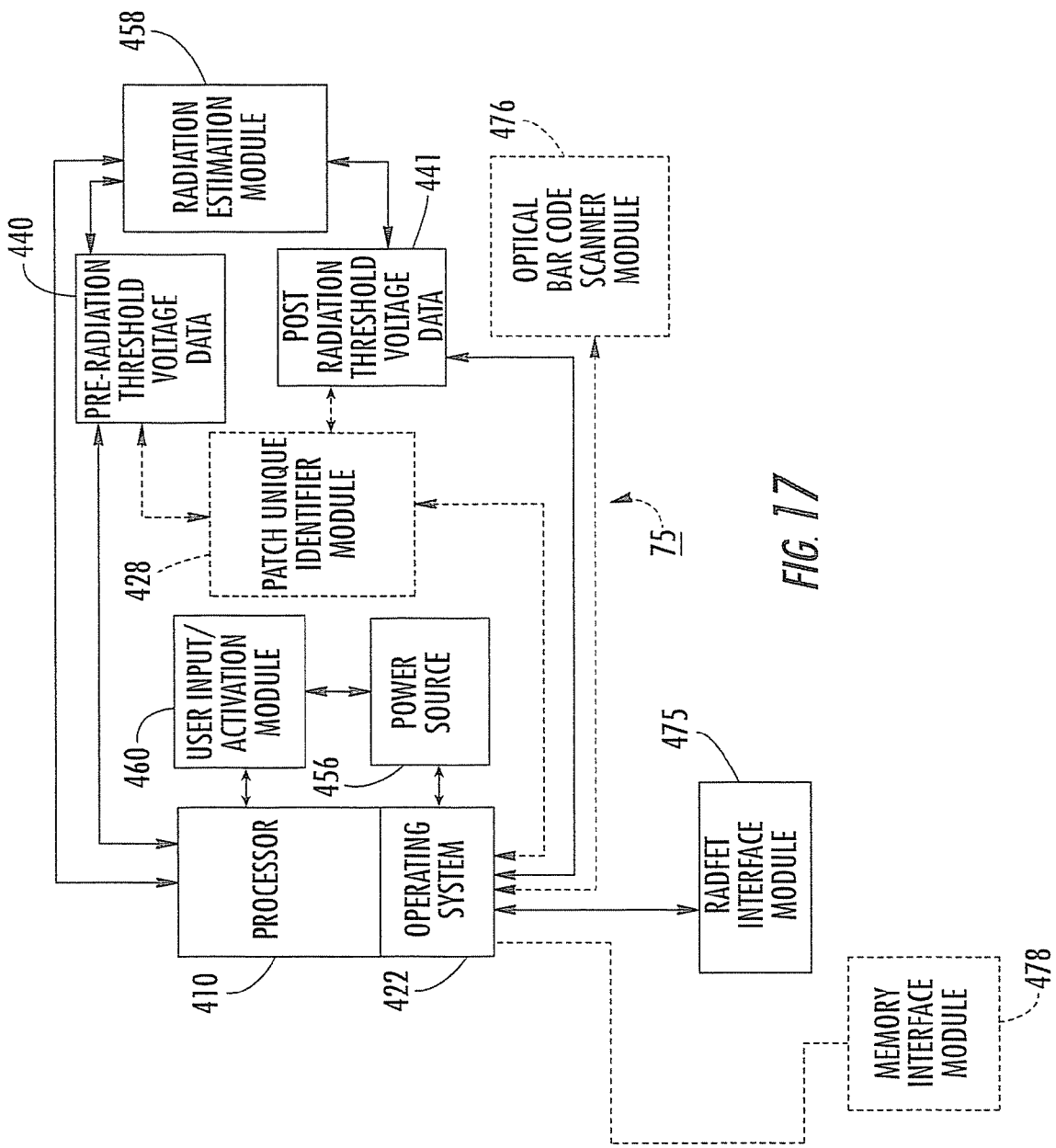
FIG. 17 is a block diagram of a point-contact reader data acquisition system some according to embodiments of the present invention.

FIG. 17 is a block diagram illustration of one embodiment of a reader 75 according to the present invention. As shown, the reader 75 includes an operating system 422, a processor 410, a power source 456, and a user activation/input module 460. The reader 75 can also include a RADFET interface module 475 and a sensor patch memory interface module 478. The reader 75 may communicate with the sensor patch memory using, for example, a standard I2C protocol and in some embodiments may use a clock as a data line. As discussed above, in certain embodiments, the sensor patch 30 may be configured to communicate wirelessly with the reader 75. In these embodiments, the interface module 475 may be configured to receive wireless signals from the sensor patch 30. The reader 75 may optionally include a sensor patch identifier module 428 to track which sensor patch 30 has a particular radiation dose result. The identifier module 428 may allow the user to input via an input keypad associated with the reader, an alphanumeric identifier (F1, B1, etc.) for a particular sensor patch prior to obtaining the reading, or a bar code identifier or other automated identifier means can be used (such as scanning a bar code label on the sensor and the like).

The reader 75 also includes pre-radiation (zero dose) threshold voltage data 440, post radiation threshold voltage data 441, and a radiation estimation module 458. The pre-radiation threshold voltage data 440 and the post radiation threshold data 441 may be obtained when the MOSFET is biased with the zero temperature bias current discussed above. The zero temperature bias current may be obtained before the administration of the radiation therapy, stored in the sensor patch memory 67 (FIG. 11) and obtained by the reader using the sensor patch memory interface module 478. The radiation estimation module 458 may also be configured to extrapolate to arrive at the radiation dose delivered to the tumor site. In some embodiments of the present invention, the radiation estimation module 458 may be further configured to prompt a doctor or technician for predetermined data needed to calculate or estimate the radiation dose. The predetermined data may include conversion factors and/or correction factors associated with different versions of the sensor patches. As shown, the reader 75 may also include an optical bar code scanner module 476 to allow the reader to input the characterizing zero dose threshold voltage values by optically reading same. Similarly, calibration data can be entered via the bar the bar code scanner 476 or memory 67 from the patches 30. Alternatively, the clinician can enter the desired data in situ as desired.

Tables 8 and 9 of FIGS. 32A, 32B and 33 contain a listing the functional specification of readers and sensor patches, respectively, according to some embodiments of the present invention. It will be understood that the functional specifications listed in FIGS. 32A, 32B and 33 are provided for exemplary purposes only and that embodiments of the present invention are not limited to this configuration.

Although primarily described for oncologic therapies, the devices can be used to monitor other radiation exposures, particularly exposures during medical procedures, such as fluoroscopy, brachytherapy, and the like.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A computer program product held in a reader for evaluating a radiation dose delivered to a patient during a therapy session, the computer program product comprising:
  a non-transitory computer readable storage medium having computer readable program code embodied in the medium, the computer-readable program code comprising:
  computer readable program code configured to communicate with an electronic memory of at least one single use dosimeter patch to obtain threshold data corresponding to a dose amount of radiation exposure that the at least one sensor patch is exposed to in use;
  computer readable program code configured to prompt a user to provide predetermined data associate with the dose amount, patient data and/or clinic data; and
  computer readable program code configured to measure a zero temperature coefficient of a MOSFET prior to administration of radiation during a therapeutic procedure.

2. The computer program product of claim 1 further comprising:
  computer readable program code An ex threshold voltage value of the MOSFET;

computer readable program code configured to bias the MOSFET using the stored zero temperature coefficient after the therapeutic procedure;

computer readable program code configured to measure the post-radiation threshold voltage value of the MOSFET device; and computer readable program code configured to automatically calculate the radiation dose based on the pre-radiation voltage value and the post-radiation voltage value of the MOSFET.

3. The computer program product of claim 2 further comprising computer readable program code configured to automatically reduce the value of the post-radiation threshold voltage by the pre-radiation threshold voltage value and automatically compare a result to a dose curve to automatically determine the radiation dose.

4. The computer program product of claim 2 wherein the computer readable program code configured to prompt a user further comprises computer readable program code configured to automatically prompt a user for predetermined data to automatically determine the radiation dose using the predetermined data.

5. The computer program product of claim 4 wherein the predetermined data comprises a correction factor related to the at least one sensor patch.

6. A portable medical dose reader device comprising:

a portable housing; and a circuit integrated with the portable housing, the circuit being configured to communicate with an electronic memory of at least one single use dosimeter patch that can be releasably secured to be in intimate contact with skin of the patient to obtain voltage threshold data corresponding to a dose amount of radiation exposure that the at least one sensor patch is exposed to in use and to prompt a user to input predetermined data associated with the dose amount, patient data and/or clinic data;

wherein the circuit is further configured to measure a zero temperature coefficient of the MOSFET prior to administration of radiation during a therapeutic procedure.

7. The reader of claim 6 wherein the reader is configured to make electrical contact with the at least one single use dosimeter patch to communicate with the electronic memory to obtain the threshold data corresponding to the dose amount of radiation exposure the at least one sensor patch is exposed to during the administering of therapeutic radiation.

8. The reader of claim 7 wherein the circuit is further configured to wirelessly communicate with the electronic memory of the at least one patch to obtain the threshold data corresponding to the dose amount of radiation exposure the at least one sensor patch is exposed to during the administering of therapeutic radiation.

9. The reader of claim 6 wherein the reader is further configured to automatically prompt the user of the reader for predetermined data before determining the radiation dose; then automatically determine the radiation dose using the predetermined data.

10. The reader of claim 9 wherein the predetermined data comprises a correction factor related to the at least one sensor patch.

11. The reader of claim 6 wherein the electronic memory further comprises detected and/or calculated radiation doses, date and/or time stamps, and/or a clinician entered patient identifier and/or record number.

12. The reader of claim 6, wherein the at least one single-use dosimeter sensor patch is self-contained during irradiation.

* * * * *